US009833500B2

(12) United States Patent
Gurney et al.

(10) Patent No.: US 9,833,500 B2
(45) Date of Patent: Dec. 5, 2017

(54) IMMUNOTHERAPY WITH BINDING AGENTS

(71) Applicant: OncoMed Pharmaceuticals, Inc., Redwood City, CA (US)

(72) Inventors: Austin L. Gurney, San Francisco, CA (US); Fumiko Takada Axelrod, Palo Alto, CA (US)

(73) Assignee: OncoMed Pharmaceuticals, Inc., Redwood City, CA (US)

( * ) Notice: Subject to any disclaimer, the term of this patent is extended or adjusted under 35 U.S.C. 154(b) by 31 days.

(21) Appl. No.: 15/088,888

(22) Filed: Apr. 1, 2016

(65) Prior Publication Data

US 2016/0346368 A1 Dec. 1, 2016

Related U.S. Application Data

(62) Division of application No. 14/096,510, filed on Dec. 4, 2013, now Pat. No. 9,327,014.

(60) Provisional application No. 61/733,177, filed on Dec. 4, 2012, provisional application No. 61/789,268, filed on Mar. 15, 2013.

(51) Int. Cl.
| | |
|---|---|
| *A61K 38/17* | (2006.01) |
| *C07K 14/705* | (2006.01) |
| *A61K 39/00* | (2006.01) |
| *A61K 38/19* | (2006.01) |
| *A61K 45/06* | (2006.01) |

(52) U.S. Cl.
CPC ........ *A61K 39/0005* (2013.01); *A61K 38/177* (2013.01); *A61K 38/1774* (2013.01); *A61K 38/19* (2013.01); *A61K 45/06* (2013.01); *C07K 14/705* (2013.01)

(58) Field of Classification Search
None
See application file for complete search history.

(56) References Cited

U.S. PATENT DOCUMENTS

| | | | |
|---|---|---|---|
| 4,588,585 | A | 5/1986 | Mark et al. |
| 5,731,168 | A | 3/1998 | Carter et al. |
| 6,413,746 | B1 | 7/2002 | Field |
| 6,660,501 | B2 | 12/2003 | Field |
| 9,327,014 | B2 | 5/2016 | Gurney et al. |
| 2005/0276799 | A1 | 12/2005 | Hinton et al. |
| 2007/0037165 | A1 | 2/2007 | Venter et al. |
| 2007/0122403 | A1 | 5/2007 | Dall'Acqua et al. |
| 2007/0148164 | A1 | 6/2007 | Farrington et al. |
| 2008/0064049 | A1 | 3/2008 | Clarke et al. |
| 2008/0177048 | A1 | 7/2008 | Gagnon |
| 2008/0178305 | A1 | 7/2008 | Clarke et al. |
| 2008/0187954 | A1 | 8/2008 | Kallmeier et al. |
| 2008/0312425 | A1 | 12/2008 | Bonnerjea et al. |
| 2009/0187005 | A1 | 7/2009 | Gagnon |
| 2009/0258013 | A1 | 10/2009 | Clark et al. |
| 2011/0123532 | A1 | 5/2011 | Gurney et al. |
| 2012/0219540 | A1 | 8/2012 | Gao et al. |
| 2014/0186380 | A1 | 7/2014 | Gurney et al. |

FOREIGN PATENT DOCUMENTS

| | | |
|---|---|---|
| WO | WO 03/000928 A2 | 1/2003 |
| WO | WO 2004/009823 A1 | 1/2004 |
| WO | WO 2008/042236 A2 | 4/2008 |
| WO | WO 2014/089169 A2 | 6/2014 |

OTHER PUBLICATIONS

Extended European Search Report for EP Application No. 13861068.8, European Patent Office, Munich, Germany, dated Jul. 12, 2016, 5 pages (corrected version of the Extended European Search Report dated May 10, 2016 cited as NPL38).

Koike, S., et al., "The poliovirus receptor protein is produced both as membrane-bound and secreted forms," *The EMBO Journal* 9(10):3217-3224, Oxford University Press, England (1990).

Koike, S., et al., "A second gene for the African green monkey poliovirus receptor that has no putative N-glycosylation site in the functional N-terminal immunoglobulin-like domain," *Journal of Virology* 66(12):7059-7066, American Society for Microbiology, United States (1992).

Brennan, M., et al., "Preparation of Bispecific Antibodies by Chemical Recombination of Monoclonal Immunoglobulin G1 Fragments," *Science* 229(1408): 81-83, American Association for the Advancement of Science, United States (1985).

Carlsten, M., et al., "DNAX Accessory Molecule-1 Mediated Recognition of Freshly Isolated Ovarian Carcinoma by Resting Natural Killer Cells," *Cancer Research* 67(3): 1317-1325, American Association for Cancer Research, United States (2007).

Castriconi, R., et al., "Natural Killer Cell-Mediated Killing of Freshly Isolated Neuroblastoma Cells: Critical Role of DNAX Accessory Molecule-1-Poliovirus Receptor Interaction," *Cancer Research* 64: 9180-9184, American Association for Cancer Research, United States (2004).

El-Sherbiny, Y.M., et al., "The Requirement for DNAM-1, NKG2D, and NKp46 in the Natural Killer Cell-Mediated Killing of Myeloma Cells," *Cancer Research* 67(18): 8444-8449, American Association for Cancer Research, United States (2007).

Gill, D.S. and Damle, N.K., "Biopharmaceutical drug discovery using novel protein scaffolds," *Current Opinion in Biotechnology* 17:653-658, Elsevier Ltd., England (2006).

Gruber, M., et al., "Efficient Tumor Cell Lysis Mediated by a Bispecific Single Chain Antibody Expressed in *Escherichia coli*," *Journal of Immunology* 152(11): 5368-5374, The American Association of Immunologists, United States (1994).

Hosse, R.J., et al., "A new generation of protein display scaffolds for molecular recognition," *Protein Science* 15: 14-27, The Protein Society, United States (2006).

(Continued)

*Primary Examiner* — Julie Wu
(74) *Attorney, Agent, or Firm* — Sterne, Kessler, Goldstein & Fox P.L.L.C.

(57) ABSTRACT

Binding agents that modulate the immune response are disclosed. The binding agents may include soluble receptors, polypeptides, and/or antibodies. Also disclosed are methods of using the binding agents for the treatment of diseases such as cancer.

18 Claims, 10 Drawing Sheets

(56) References Cited

OTHER PUBLICATIONS

Kostelny, S.A., et al., "Formation of a Bispecific Antibody by the use of Leucine Zippers," *The Journal of Immunology* 148: 1547-1553, The American Association of Immunologists, United States (1992).

Luckow, V.A. and Summers, M.D., "Trends in the Development of Baculovirus Expression Vectors," *Bio/Technology* 6:47-55, Nature Publishing Group, England (1988).

Mark, D.F., et al., "Site-specific mutagenesis of the human fibroblast interferon gene," *Proc. Nat. Acad. Sci. USA* 81:5662-5666, National Academy of Sciences, United States (1984).

Masson, D., et al., "Overexpression of the CD155 gene in human colorectal carcinoma," *Gut* 49:236-240, British Medical Association, London (2001).

Milstein, C. and Cuello, A.C., "Hybrid hybridomas and their use in immunohistochemistry," *Nature* 305:537-540, Macmillan Journals Ltd, United States (1983).

Nygren, P.-A., "Alternative binding proteins: Affibody binding proteins developed from a small three-helix bundle scaffold," *The FEBS Journal* 275:2668-2676, John Wildey & Sons, Inc., United States (2008).

Pende, D., et al., "Analysis of the receptor-ligand interactions in the natural killer-mediated lysis of freshly isolated myeloid or lymphoblastic leukemias: evidence for the involvement of the Poliovirus receptor (CD155) and Nectin-2 (CD112)," *Blood* 105:2066-2073, The American Society of Hematology, United States (2005).

Shalaby, M.R., et al., "Development of Humanized Bispecific Antibodies Reactive with Cytotoxic Lymphocytes and Tumor Cells Overexpressing the HER2 Protooncogene," *The Journal of Experimental Medicine* 175:217-225, The Rockefeller University Press, United States (1992).

Skerra, A., "Alternative non-antibody scaffolds for molecular recognition," *Current Opinion in Biotechnology* 18:295-304, Elsevier Ltd, England (2007).

Skerra, A., "Alternative binding proteins: Anticalins-harnessing the structural plasticity of the lipocalin ligand pocket to engineer novel binding activities," *The FEBS Journal* 275:2677-2683, John Wiley & Sons, Inc., United States (2008).

Suresh, M.R., et al., "Bispecific Monoclonal Antibodies from Hybrid Hybridomas," *Methods in Enzymology* 121:210-228, Academic Press, Inc., United States (1986).

Tahara-Hanaoka, S., et al., "Tumor rejection by the poliovirus receptor family ligands of the DNAM-1 (CD226) receptor," *Blood* 107: 1491-1496, The American Society of Hematology, United States (2006).

Traunecker, A., et al., "Bispecific single chain molecules (Janusins) target cytotoxic lymphocytes on HIV infected cells," *The EMBO Journal* 10(12):3655-3659, Oxford University Press, England (1991).

Tutt, A., et al., "Trispecific F(ab')$_3$ Derivatives That Use Cooperative Signaling Via the TCR/CD3 Complex and CD2 to Activate and Redirect Resting Cytotoxic T Cells," *The Journal of Immunology* 147(1):60-69, The American Association of Immunologists, United States (1991).

Wong, C.W., et al., "The Role of Immunoglobulin Superfamily Cell Adhesion Molecules in Cancer Metastasis," *International Journal of Cell Biology* 2012:1-9, Hindawi Publishing Corporation, United States (Jan. 2012).

Liu, J., et al., "Crystal Structure of Cell Adhesion Molecule Nectin-2/CD112 and Its Binding to Immune Receptor DNAM-1/CD226" *The Journal of Immunology* 188: 5511-5520, The American Association of Immunologists, Inc., United States (epub Apr. 2012).

Stengel, K.F., et at, "Structure of TIGIT immunoreceptor bound to poliovirus receptor reveals a cell-cell adhesion and signaling mechanism that requires cis-trans receptor clustering," *PNAS* 109(14); 5399-5404, National Academy of Scienees, United States (Apr. 2012).

Yu, X., et al., "The surface protein TIGIT suppresses T cell activation by promoting the generation of mature immunoregulatory dendritic cells," *Nature Immunology* 10(1): 48-57, Nature America, Inc., United States (epub 2008).

International Search Report and Written Opinion in International Application No. PCT/US13/73038, U.S. Patent and Trademark Office, dated May 20, 2014, 29 pages.

GenBank Accession No. P15151.2, accessed at https://www.ncbi.nlm.nih.gov/protein/P15151, accessed on Jun. 22, 2015, 12 pages.

GenBank Accession. No. Q15223.3, accessed at https://www.ncbi.nlm.nih.gov/protein/Q15223, accessed on Jun. 22, 2015, 13 pages.

GenBank Accession No. Q92692.1, accessed at https://www.ncbi.nlm.nih.gov/protein/Q92692, accessed on Jun. 22, 2015, 10 pages.

GenBank Accession No. Q9NQS3.1, accessed at https://www.ncbi.nlm.nih.gov/protein/Q9NQS3, accessed on Jun. 22, 2015, 8 pages.

GenBank Accession No. Q96NY.8.1, accessed at https://www.ncbi.nlm.nih.gov/protein/Q96NY8, accessed on Jun. 22, 2015, 11 pages.

GenBank Accession No. Q15762.2, accessed at https://www.ncbi.nlm.nih.gov/protein/Q15762, accessed on Jun. 22, 2015, 6 pages.

GenBank Accession No. P40200.2, accessed at https://www.ncbi.nlm.nih.gov/protein/P40200, accessed on Jun. 23, 2015, 6 pages.

GenBank Accession No. Q495A1.1, accessed at https://www.ncbi.nlm.nih.gov/protein/Q495A1, accessed on Jun. 23, 2015, 8 pages.

International Report on Patentability and Written Opinion in International Patent Application No. PCT/US2013/073038, The International Bureau of WIPO, Switzerland, dated Jun. 9, 2015, 15 pages.

Rentero, I. and Heinis, C., "Screening of large molecule diversities by phage display," *Chimia* 65(11):843-845, Schweizerische Chemische Gesellschaft, Switzerland (2011).

Office Action, Non-Final Rejection dated Aug. 5, 2015, in U.S. Appl. No. 14/096,510, Gurney, A.L., et al., filed Dec. 4, 2013.

Extended European Search Report for EP Application No. 13861068.8, European Patent Office, Munich, Germany, dated May 10, 2016, 9 pages.

Kindberg, E., et al., "Ala67Thr Mutation in the Poliovirus Receptor CD155 is a Potential Risk Factor for Vaccine and Wild-Type Paralytic Poliomyelitis," *Journal of Medical Virology* 81(5):933-936, Wiley-Liss, Inc., United States (2009).

Merrill, M.K., et al., "Poliovirus receptor CD155-targeted oncolysis of glioma," *Neuro-Oncology* 6(3):208-217, The Society for Neuro-Oncology, England (2004).

Pavio, N., et al., "Expression of Mutated Poliovirus Receptors in Human Neuroblastoma Cells Persistently Infected with Poliovirus," *Virology* 274(2):331-342, Academic Press, United States (2000).

Sözen, M.A., et al., "Mutation and association analysis of the PVR and PVRL2 genes in patients with non-syndromic cleft lip and palate," *Genetics and Molecular Biology* 32(3);466-469, Sociedade Brasileira de Genética, Brazil (2009).

FIG. 1

Alignment of Human and Mouse N-Terminal Ig Domain Region
of PVR Family Receptors

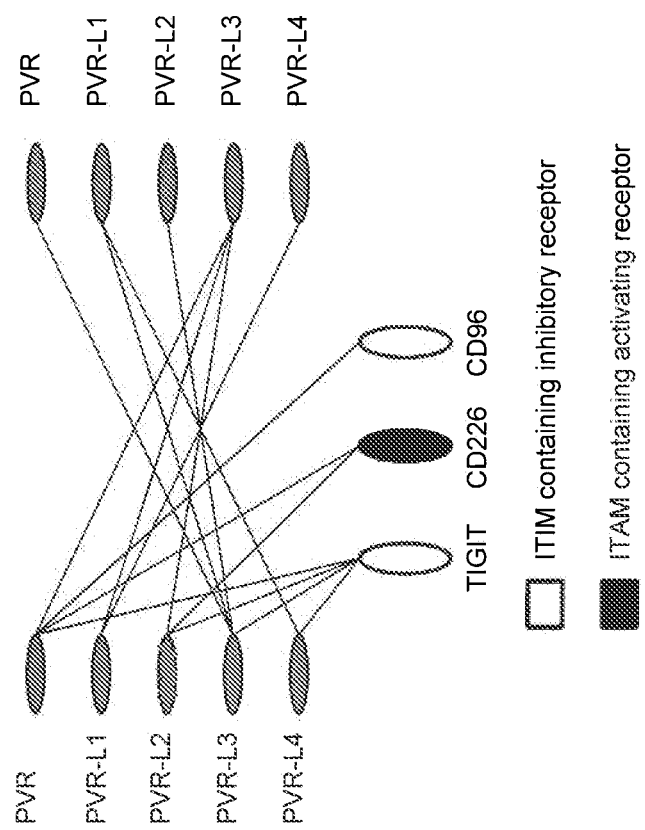

Figure 4A

PVR (SEQ ID NO:17)

28
DVVVQAPTQVPGFLGDSVTLPCYLQVPNMEVTHVSQLTWARHGESGSMAVFHQ
                                                         65  67     72-74

81 82 84 85
TQGPSYSESKRLEFVAARLGAELRNASLRMFGLRVEDEGNYTCLFVTFPQ

GSRSVDIWLRVLA

Figure 4B

PVRL-2 (SEQ ID NO:23)

33
DVRVQVLPEVRGQLGGTVELPCHLLPPVPGLYISLVTWQRPDAPANHQ
                                                        69 71     79 80

81        88 89 91 92
NVAAFHPKMGPSFPSPKPGSERLSFVSAKQSTGQDTEAELQDATLALHGL

TVEDEGNYTCEFATFPKGSVRGMTWLRVIA

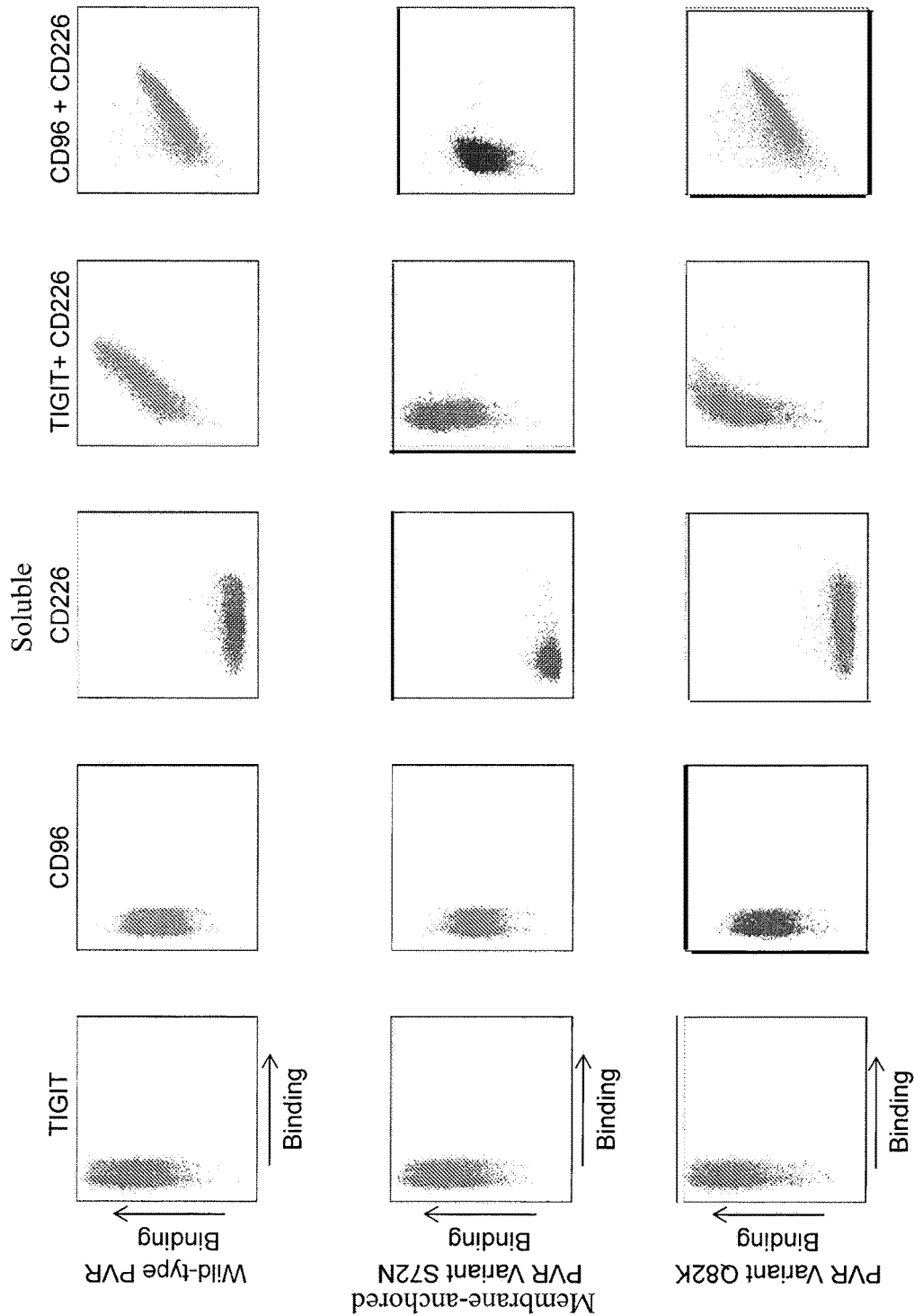

IMMUNOTHERAPY WITH BINDING AGENTS

CROSS-REFERENCE TO RELATED APPLICATIONS

This application is a divisional of U.S. application Ser. No. 14/096,510, filed Dec. 4, 2013, which claims priority benefit of U.S. Provisional Application No. 61/733,177, filed Dec. 4, 2012 and U.S. Provisional Application No. 61/789,268, filed Mar. 15, 2013 each of which is hereby incorporated by reference herein in its entirety.

REFERENCE TO SEQUENCE LISTING SUBMITTED ELECTRONICALLY

The content of the electronically submitted sequence listing (Name: 2293_0990003_SEQLISTING.ascii.TXT; Size: 118,146 bytes; and Date of Creation: Mar. 28, 2016) filed herewith is incorporated herein by reference in its entirety.

FIELD OF THE INVENTION

This invention generally relates to agents that modulate the immune response, such as soluble receptors, antibodies, and small molecules, as well as to methods of using the agents for the treatment of diseases such as cancer.

BACKGROUND OF THE INVENTION

The basis for immunotherapy is the manipulation of the immune system, including both innate immune responses and adaptive immune responses. The aim of immunotherapy is to treat diseases by controlling the immune response to a "foreign agent", for example a pathogen or a tumor cell. This may include methods to induce or enhance specific immune responses or to inhibit or reduce specific immune responses. The immune system is a highly complex system made up of a great number of cell types, including, T-cells, B-cells, natural killer cells, antigen-presenting cells, dendritic cells, monocytes, and macrophages. These cells possess complex and subtle systems for controlling their interactions, including utilizing numerous receptors and soluble factors for the process. The cells utilize both activating and inhibitory mechanisms to keep responses in check and not allow negative consequences of an uncontrolled immune response (e.g., autoimmune diseases).

The concept of cancer immunosurveillance is based on the theory that the immune system can recognize tumor cells, mount an immune response, and suppress the development and/or progression of a tumor. However, it is clear that many cancerous cells have developed mechanisms to evade the immune system allowing the uninhibited growth of tumors. Cancer immunotherapy focuses on the development of agents that can activate and/or boost the immune system to achieve a more effective response to killing tumor cells and inhibiting tumor growth.

BRIEF SUMMARY OF THE INVENTION

The present invention provides binding agents, such as soluble receptors, polypeptides, antibodies, and small molecules that modulate the immune response. The invention also provides compositions, such as pharmaceutical compositions, comprising the binding agents. The invention further provides methods of administering the binding agents to a subject in need thereof.

In one aspect, the invention provides a binding agent that specifically binds the extracellular domain of human TIGIT. As used herein, a "binding agent" includes but is not limited to, a soluble receptor, a polypeptide, an antibody, a small molecule, and combinations thereof. In some embodiments, the binding agent comprises a soluble receptor. In some embodiments, the binding agent comprises a soluble receptor comprising a poliovirus receptor (PVR) variant. In some embodiments, the binding agent is a soluble receptor comprising a poliovirus receptor (PVR) variant. In some embodiments, the binding agent comprises a soluble receptor comprising a PVR variant, wherein the PVR variant comprises one or more amino acid substitutions as compared to wild-type PVR. In some embodiments, the binding agent comprises a soluble receptor comprising a PVR variant which specifically binds the extracellular domain of human TIGIT and does not bind or binds weakly to the extracellular domain of human CD226. In some embodiments, the binding agent comprises a soluble receptor comprising a PVR variant which specifically binds the extracellular domain of human TIGIT and also binds the extracellular domain of human CD96. In some embodiments, the binding agent comprises a soluble receptor comprising a PVR variant that specifically binds the extracellular domain of human TIGIT and the extracellular domain of human CD96, but does not bind or binds weakly to the extracellular domain of human CD226. In some embodiments, the binding agent comprises a soluble receptor comprising a PVR variant that specifically binds the extracellular domain of human TIGIT and has reduced binding to the extracellular domain of human CD226 as compared to wild-type PVR. In some embodiments, the binding agent comprises a soluble receptor comprising a PVR variant which specifically binds the extracellular domain of human TIGIT and the extracellular domain of human CD96, but has reduced binding to the extracellular domain of human CD226 as compared to wild type PVR.

In some embodiments, the PVR variant comprises one or more immunoglobulin (Ig)-like domains of human PVR. In some embodiments, the PVR variant comprises an N-terminal IgV domain of human PVR. In some embodiments, the PVR variant comprises an N-terminal IgV domain of human PVR, wherein the IgV domain comprises one or more amino acid substitutions as compared to wild-type PVR. In some embodiments, the PVR variant consists essentially of an N-terminal IgV domain of human PVR, wherein the IgV domain comprises one or more amino acid substitutions as compared to wild-type PVR. The amino acid sequence of human PVR is known in the art and is included herein as SEQ ID NO:1. In some embodiments, the PVR variant comprises substitutions in one or more amino acids corresponding to amino acids 40-143 of wild-type PVR. In some embodiments, the PVR variant comprises substitutions in one or more amino acids corresponding to amino acids 60-90 and/or amino acids 125-133 of wild-type PVR. In some embodiments, the PVR variant comprises substitutions in one or more amino acids corresponding to amino acids 465, 67, 72, 73, 74, 81, 82, 84, and 85 of wild-type PVR. In some embodiments, the PVR variant comprises an amino acid substitution corresponding to amino acid 72 of wild-type PVR. In some embodiments, the PVR variant comprises an amino acid substitution corresponding to amino acid 82 of wild-type PVR. In some embodiments, the PVR variant comprises amino acid substitutions corresponding to amino acid 72 and amino acid 82 of wild-type PVR. In some embodiments, the PVR variant comprises an amino acid sequence selected from the group consisting of SEQ ID NO:18, SEQ ID NO:19, SEQ ID NO:20, and SEQ ID NO:21.

In another aspect, the invention provides a polypeptide comprising one or more Ig-like domains of human PVR, wherein the one or more Ig-like domains comprise substitutions in one or more amino acids as compared to wild-type PVR. In some embodiments, the polypeptide specifically binds the extracellular domain of human TIGIT and does not bind or binds weakly to the extracellular domain of human CD226. In some embodiments, the polypeptide comprises an N-terminal IgV domain of human PVR. In some embodiments, the polypeptide comprises an IgV domain of PVR that comprises an N-terminal IgV domain of human PVR, wherein the IgV domain comprises one or more amino acid substitutions as compared to wild-type PVR. In some embodiments, the polypeptide comprises an IgV domain of PVR that consists essentially of an N-terminal IgV domain of human PVR, wherein the IgV domain comprises one or more amino acid substitutions as compared to wild-type PVR. In some embodiments, a polypeptide comprises a PVR variant, wherein the PVR variant comprises one or more amino acid substitutions as compared to wild-type PVR. In some embodiments, polypeptide comprises a PVR variant that specifically binds the extracellular domain of human TIGIT and does not bind or binds weakly to the extracellular domain of human CD226. In some embodiments, the polypeptide also binds the extracellular domain of human CD96. In some embodiments, the polypeptide comprises a PVR variant, wherein the PVR variant comprises substitutions in one or more amino acids corresponding to amino acids 40-143 of wild-type PVR. In some embodiments, the polypeptide comprises a PVR variant, wherein the PVR variant comprises substitutions in one or more amino acids corresponding to amino acids 60-90 and/or amino acids 125-133 of wild-type PVR. In some embodiments, the polypeptide comprises a PVR variant, wherein the PVR variant comprises substitutions in one or more amino acids corresponding to amino acids 465, 67, 72, 73, 74, 81, 82, 84, and 85 of wild-type PVR. In some embodiments, the polypeptide comprises a PVR variant, wherein the PVR variant comprises an amino acid substitution corresponding to amino acid 72 of wild-type PVR. In some embodiments, the polypeptide comprises a PVR variant, wherein the PVR variant comprises an amino acid substitution corresponding to amino acid 82 of wild-type PVR. In some embodiments, the polypeptide comprises a PVR variant, wherein the PVR variant comprises amino acid substitutions corresponding to amino acid 72 and amino acid 82 of wild-type PVR. In some embodiments, the polypeptide comprises an amino acid sequence selected from the group consisting of SEQ ID NO:18, SEQ ID NO:19, SEQ ID NO:20, and SEQ ID NO:21.

In another aspect, the invention provides a TIGIT-binding agent comprising one or more Ig-like domains of a variant human PVR, wherein the one or more Ig-like domains of PVR comprise one or more amino acid substitutions as compared to wild-type PVR. In another aspect, the invention provides a TIGIT-binding agent comprising one or more Ig-like domains of a variant human PVR, wherein the one or more Ig-like domains of PVR comprise one or more substitutions in amino acids corresponding to amino acids 65, 67, 72, 73, 74, 81, 82, 84, or 85 of wild-type PVR. In some embodiments, the TIGIT-binding agent comprises one or more Ig-like domains of a variant human PVRL2, wherein the one or more Ig-like domains of PVRL2 comprise one or more amino acid substitutions as compared to wild-type PVRL2. In some embodiments, the TIGIT-binding agent comprises one or more Ig-like domains of a variant human PVRL3, wherein the one or more Ig-like domains of PVRL3 comprise one or more amino acid substitutions as compared to wild-type PVRL3. In some embodiments, the TIGIT-binding agent comprises one or more Ig-like domains of a variant human PVRL4, wherein the one or more Ig-like domains of PVRL4 comprise one or more amino acid substitutions as compared to wild-type PVRL4.

In some embodiments of each of the aforementioned aspects and embodiments, as well as other aspects and embodiments described herein, the binding agent comprises a non-PVR polypeptide. In some embodiments, the PVR variant is linked to a non-PVR polypeptide. In some embodiments, the PVR variant is directly linked to a non-PVR polypeptide. In some embodiments, the PVR variant is linked to a non-PVR polypeptide with a peptide linker. In some embodiments, the non-PVR polypeptide comprises a human Fc region. In some embodiments, the non-PVR polypeptide consists essentially of a human Fc region. In some embodiments, the non-PVR polypeptide consists of a human Fc region. In some embodiments, the human Fc region is selected from the group consisting of SEQ ID NO:26, SEQ ID NO:27, SEQ ID NO:28, SEQ ID NO:29, SEQ ID NO:30, SEQ ID NO:31, SEQ ID NO:43, SEQ ID NO:44, SEQ ID NO:45, SEQ ID NO:46, SEQ ID NO:47, and SEQ ID NO:48.

In some embodiments of each of the aforementioned aspects and embodiments, as well as other aspects and embodiments described herein, the binding agent is monovalent. In some embodiments, the binding agent is bivalent. In some embodiments, the binding agent is monospecific. In some embodiments, the binding agent is bispecific.

In some embodiments of each of the aforementioned aspects and embodiments, as well as other aspects and embodiments described herein, the binding agent is a heteromultimeric agent. In some embodiments, the binding agent is a heterodimeric agent. In some embodiments, the heterodimeric agent comprises a first polypeptide that binds TIGIT and a second polypeptide that binds a second target. In some embodiments, the heterodimeric agent comprises a first polypeptide that binds TIGIT and a second polypeptide that comprises an immune response stimulating agent. In some embodiments, the heterodimeric agent comprises a first polypeptide comprising a PVR variant described herein and a second polypeptide comprising an immune response stimulating agent. In some embodiments, the immune response stimulating agent may be, but is not limited to, granulocyte-macrophage colony stimulating factor (GM-CSF), macrophage colony stimulating factor (M-CSF), granulocyte colony stimulating factor (G-CSF), interleukin 3 (IL-3), interleukin 12 (IL-12), interleukin 1 (IL-1), interleukin 2 (IL-2), interleukin 15 (IL-15), CD80, CD86, anti-CD3 antibody, anti-CTLA-4 antibody, and/or anti-CD28 antibody. In some embodiments, the heterodimeric agent comprises two polypeptides, wherein each polypeptide comprises a human IgG2 CH3 domain, and wherein the amino acids at positions corresponding to positions 249 and 288 of SEQ ID NO:40 of the first IgG2 CH3 domain are replaced with glutamate or aspartate, and wherein the amino acids at positions corresponding to positions 236 and 278 of SEQ ID NO:40 of the second IgG2 CH3 domain are replaced with lysine.

In some embodiments of each of the aforementioned aspects and embodiments, as well as other aspects and embodiments described herein, the binding agent increases cell-mediated immunity. In some embodiments, the binding agent increases T-cell activity. In some embodiments, the binding agent increases cytolytic T-cell (CTL) activity. In some embodiments, the binding agent increases natural killer (NK) cell activity. In some embodiments, the binding agent is an antagonist of TIGIT-mediated signaling. In some embodiments, the binding agent is an antagonist of CD96-mediated signaling. In some embodiments, the binding agent inhibits TIGIT signaling. In some embodiments, the binding agent inhibits CD96 signaling. In some embodiments, the binding agent inhibits TIGIT signaling and CD96 signaling. In some embodiments, the binding agent increases CD226 signaling. In some embodiments, the binding agent inhibits TIGIT signaling, inhibits CD96 signaling, but does not inhibit CD226 signaling. In some embodiments, the binding agent inhibits TIGIT signaling, inhibits CD96 signaling, and increases CD226 signaling. In some embodiments, the binding agent inhibits or blocks the interaction between PVR and TIGIT. In some embodiments, the binding agent inhibits or blocks the interaction between PVR and TIGIT and the interaction between PVR and CD96. In some embodiments, the binding agent inhibits or blocks the interaction between PVR and TIGIT, inhibits or blocks the interaction between PVR and CD96, but does not inhibit or block the interaction between PVR and CD226. In some embodiments, the binding agent inhibits or blocks the interaction between PVRL2 and TIGIT. In some embodiments, the binding agent inhibits or blocks the interaction between PVRL3 and TIGIT. In some embodiments, the binding agent inhibits or blocks the interaction between PVRL4 and TIGIT.

In another aspect, the invention provides pharmaceutical compositions comprising a soluble receptor, an antibody, a polypeptide, or a binding agent described herein and a pharmaceutically acceptable carrier. Methods of treating cancer and/or inhibiting tumor growth in a subject (e.g., a human) comprising administering to the subject an effective amount of a composition comprising the binding agents described herein are also provided.

In certain embodiments of each of the aforementioned aspects, as well as other aspects and/or embodiments described elsewhere herein, the soluble receptor, the antibody, the polypeptide, or the binding agent is isolated. In certain embodiments, the soluble receptor, the polypeptide, or the binding agent is substantially pure.

In another aspect, the invention provides polynucleotides comprising a polynucleotide that encodes a soluble receptor, an antibody, a polypeptide, or a binding agent described herein. In some embodiments, the polynucleotide is isolated. In some embodiments, the invention further provides vectors that comprise the polynucleotides, as well as cells that comprise the vectors and/or the polynucleotides. In some embodiments, the invention also provides cells comprising or producing a soluble receptor, an antibody, a polypeptide, or a binding agent described herein. In some embodiments, the cell is a monoclonal cell line. In some embodiments, the cell is a prokaryotic cell. In some embodiments, the cell is an eukaryotic cell.

In another aspect, the invention provides methods of modulating the immune response of a subject. In some embodiments, the invention provides a method of increasing an immune response in a subject comprising administering to the subject a therapeutically effective amount of a binding agent described herein. In some embodiments, the invention provides a method of activating an immune response in a subject comprising administering to the subject a therapeutically effective amount of a binding agent described herein.

In some embodiments, the immune response is to an antigenic stimulation. In some embodiments, the antigenic stimulation is a tumor or a tumor cell. In some embodiments, the antigenic stimulation is a pathogen. In some embodiments, the antigenic stimulation is a virus. In some embodiments, the antigenic stimulation is a virally-infected cell. In some embodiments, the invention provides a method of increasing the activity of immune cells. In some embodiments, the invention provides a method of increasing the activity of CD226-positive cells comprising contacting the cells with an effective amount of a binding agent described herein. In some embodiments, the CD226-positive cells are T-cells, NK cells, monocytes, macrophages, and/or B-cells. In some embodiments, the invention provides a method of increasing the activity of NK cells in a subject comprising administering to the subject a therapeutically effective amount of a binding agent described herein. In some embodiments, the invention provides a method of increasing the activity of T-cells in a subject comprising administering to the subject a therapeutically effective amount of a binding agent described herein. In some embodiments, the invention provides a method of increasing the activation of T-cells and/or NK cells in a subject comprising administering to the subject a therapeutically effective amount of a binding agent described herein. In some embodiments, the invention provides a method of increasing the T-cell response in a subject comprising administering to the subject a therapeutically effective amount of a binding agent described herein. In some embodiments, the invention provides a method of increasing the activity of CTLs in a subject comprising administering to the subject a therapeutically effective amount of a binding agent described herein. In some embodiments, the invention provides a method of increasing an immune response in a subject comprising administering to the subject a therapeutically effective amount of a soluble receptor comprising a PVR variant, wherein the soluble receptor (i) inhibits the interaction between TIGIT and PVR and (ii) inhibits the interaction between CD96 and PVR. In some embodiments, the invention provides a method of increasing an immune response in a subject comprising administering to the subject a therapeutically effective amount of a soluble receptor comprising a PVR variant, wherein the soluble receptor (i) inhibits the interaction between TIGIT and PVR, (ii) inhibits the interaction between CD96 and PVR, and (iii) does not inhibit the interaction between CD226 and PVR.

In another aspect, the invention provides methods of inhibiting tumor growth in a subject comprising administering to the subject a therapeutically effective amount of a binding agent described herein. In some embodiments, the invention provides a method of inhibiting tumor growth comprising contacting cells with an effective amount of a soluble receptor comprising a PVR variant. In some embodiments, the invention provides a method of inhibiting tumor growth comprising contacting cells with an effective amount of a soluble receptor comprising a PVR variant, wherein the soluble receptor (i) inhibits the interaction between TIGIT and PVR, (ii) inhibits the interaction between CD96 and PVR, and (iii) does not inhibit the interaction between CD226 and PVR. In some embodiments, the invention provides a method of inhibiting tumor growth in a subject comprising administering to the subject a therapeutically effective amount of a binding agent described herein. In some embodiments, the invention provides a method of inhibiting tumor growth in a subject comprising administering to the subject a therapeutically effective amount of a binding agent described herein, wherein the binding agent specifically binds the extracellular domain of human TIGIT and inhibits TIGIT signaling and does not inhibit CD226 signaling. In some embodiments, the invention provides a method of inhibiting tumor growth in a human subject comprising determining if the tumor has an elevated expression level of PVR as compared to a reference sample or a pre-determined level of PVR, and administering to the subject a therapeutically effective amount of a binding agent described herein.

In another aspect, the invention provides methods of treating cancer in a subject comprising administering to the subject a therapeutically effective amount of a binding agent described herein.

In some embodiments of each of the aforementioned aspects and embodiments, as well as other aspects and embodiments described herein, the methods comprise administering to the subject an immune response stimulating agent. In some embodiments, the immune response stimulating agent is selected from a group consisting of, but not limited to, GM-CSF, M-CSF, G-CSF, IL-3, IL-12, IL-15, IL-1, IL-2, CD80, CD86, anti-CD3 antibodies, anti-CTLA-4 antibodies, and anti-CD28 antibodies.

In another aspect, the invention provides methods of selecting a human subject for treatment with a binding agent described herein comprising, determining if the subject has a tumor that has an elevated expression level of PVR as compared to a reference sample or a pre-determined level of PVR, wherein if the tumor has an elevated expression level of PVR the subject is selected for treatment.

Where aspects or embodiments of the invention are described in terms of a Markush group or other grouping of alternatives, the present invention encompasses not only the entire group listed as a whole, but also each member of the group individually and all possible subgroups of the main group, and also the main group absent one or more of the group members. The present invention also envisages the explicit exclusion of one or more of any of the group members in the claimed invention.

BRIEF DESCRIPTION OF THE FIGURES

Figure 1:
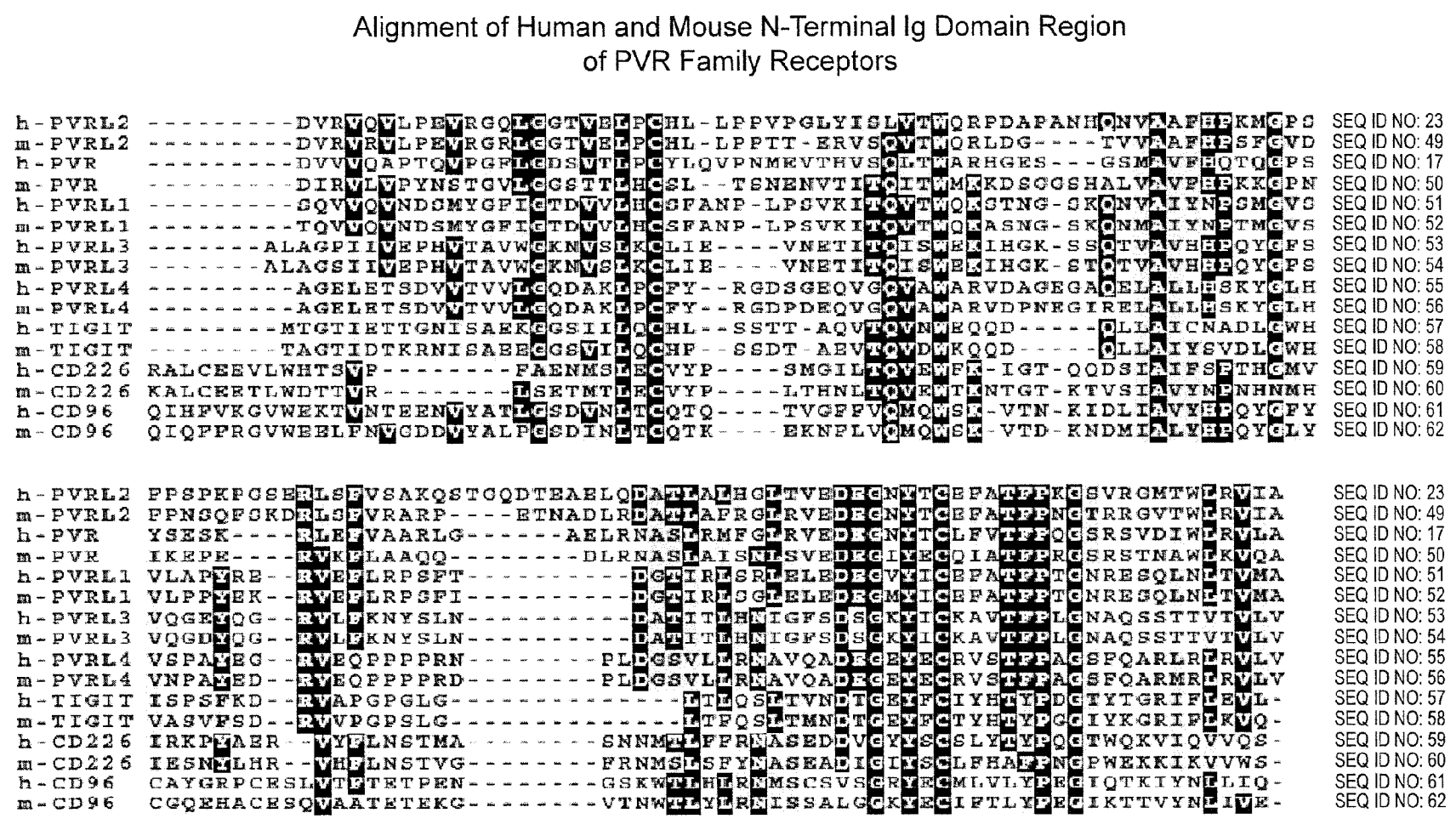

FIG. 1. Alignment of the N-terminal Ig domains of members of the PVR family.

FIGS. 3A, 3B, and 3C. FACS analysis of binding interactions between PVR family members. (3A) HEK-293T cells were transiently transfected with a cDNA expression vector encoding PVR-CD4TM-GFP, PVRL1-CD4TM-GFP, PVRL2-CD4TM-GFP, PVRL3-CD4TM-GFP, or PVRL4-CD4TM-GFP and then subsequently mixed with soluble CD226-Fc, TIGIT-Fc, or CD96-Fc fusion proteins. (3B) HEK-293T cells were transiently transfected with a cDNA expression vector encoding PVR-CD4TM-GFP, PVRL1-CD4TM-GFP, PVRL2-CD4TM-GFP, PVRL3-CD4TM-GFP, or PVRL4-CD4TM-GFP and then subsequently mixed with soluble PVR-Fc, PVRL1-Fc, PVRL2-Fc, PVRL3-Fc, or PVRL4-Fc fusion proteins. Specific binding is indicated by the presence of signal within the dark circle overlay on each FACS plot. (3C) A schematic representation of the observed binding interactions between the different members of the PVR family.

FIGS. 4A and 4B. Sequence of the N-terminal IgV domain of human PVR (SEQ ID NO:17) and human PVRL2 (SEQ ID NO:23) showing specific amino acid residues (in bold) selected for potential alteration in a library of PVR variants (4A) and PVRL2 variants (4B).

FIG. 5. FACS analysis of binding interactions between PVR variants and TIGIT, CD96, and CD226. HEK-293T cells were transiently transfected with a cDNA expression vector encoding PVR-CD4TM-GFP, PVR S72N variant-CD4TM-GFP, or PVR Q82K variant-CD4TM-GFP and then subsequently mixed with soluble TIGIT-Fc, CD96-Fc, CD226-Fc fusion proteins, a combination of TIGIT-Fc and CD226-Fc fusion proteins, or a combination of CD96-Fc and CD226-Fc fusion proteins.

DETAILED DESCRIPTION OF THE INVENTION

Figure 2:
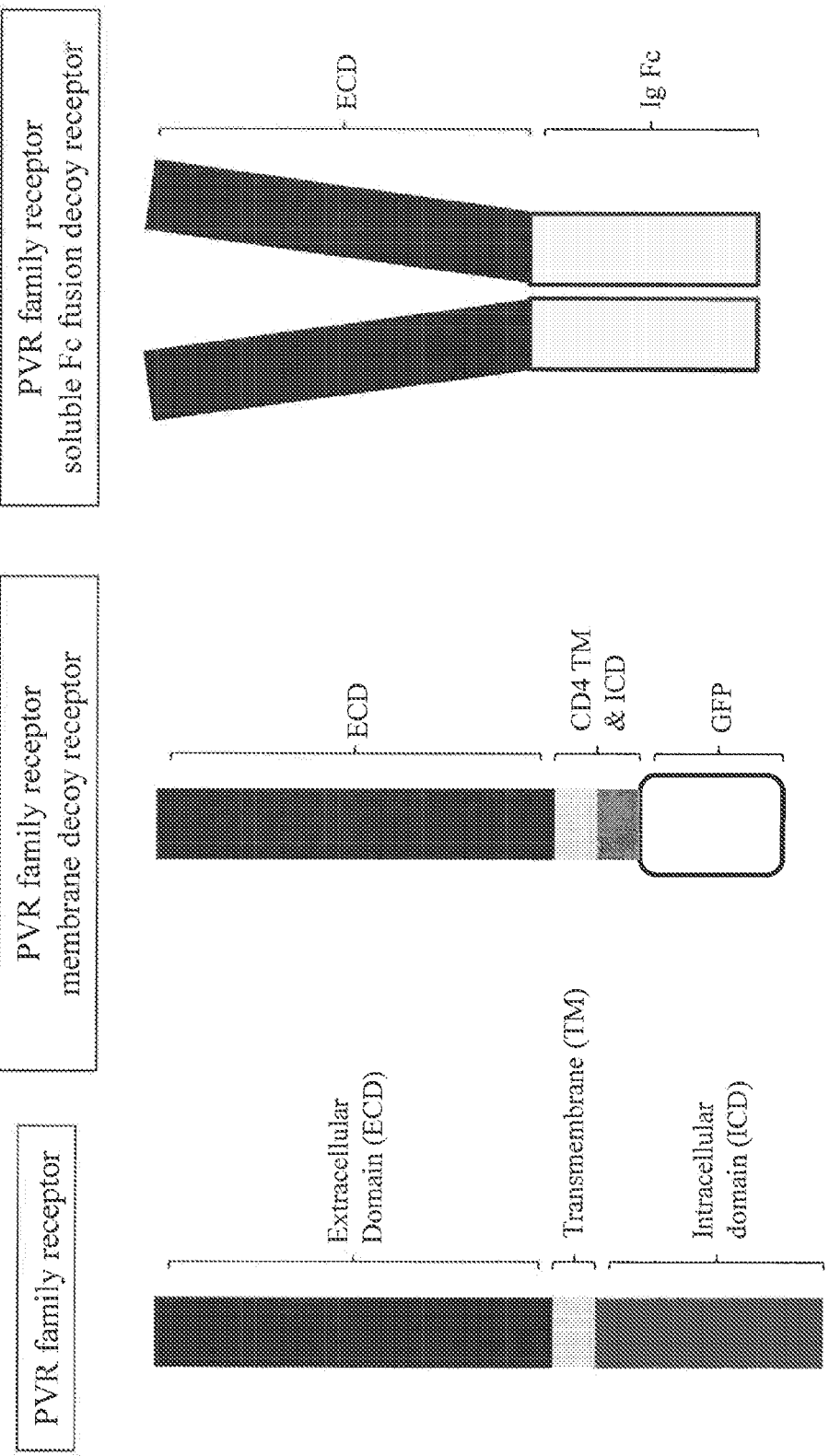
FIG. 2. Diagram of PVR family member, membrane-bound decoy receptor, and soluble receptor.

The present invention provides novel agents, including, but not limited to, polypeptides, soluble receptors, and antibodies that modulate the immune response. The agents include agonists and antagonists of receptors that are members of the immunoglobulin superfamily involved in cell interactions and immune response signaling. Related polypeptides and polynucleotides, compositions comprising the agents, and methods of making the agents are also provided. Methods of screening for agents that modulate the immune response are provided. Methods of using the novel agents, such as methods of activating an immune response, methods of stimulating an immune response, methods of promoting an immune response, methods of increasing an immune response, methods of activating natural killer (NK) cells and/or T-cells, methods of increasing the activity of NK cells and/or T-cells, methods of promoting the activity of NK cells and/or T-cells, methods of inhibiting tumor growth, and/or methods of treating cancer are further provided.

I. Definitions

To facilitate an understanding of the present invention, a number of terms and phrases are defined below.

The terms "agonist" and "agonistic" as used herein refer to or describe an agent that is capable of, directly or indirectly, substantially inducing, activating, promoting, increasing, or enhancing the biological activity of a target and/or a pathway. The term "agonist" is used herein to include any agent that partially or fully induces, activates, promotes, increases, or enhances the activity of a protein. Suitable agonists specifically include, but are not limited to, agonist antibodies or fragments thereof, soluble receptors, other fusion proteins, polypeptides, and small molecules.

The terms "antagonist" and "antagonistic" as used herein refer to or describe an agent that is capable of, directly or indirectly, partially or fully blocking, inhibiting, reducing, or neutralizing a biological activity of a target and/or pathway. The term "antagonist" is used herein to include any agent that partially or fully blocks, inhibits, reduces, or neutralizes the activity of a protein. Suitable antagonist agents specifically include, but are not limited to, antagonist antibodies or fragments thereof, soluble receptors, other fusion proteins, polypeptides, and small molecules.

The terms "modulation" and "modulate" as used herein refer to a change or an alteration in a biological activity. Modulation includes, but is not limited to, stimulating or inhibiting an activity. Modulation may be an increase or a decrease in activity, a change in binding characteristics, or any other change in the biological, functional, or immunological properties associated with the activity of a protein, a pathway, a system, or other biological targets of interest.

As used herein, the term "soluble receptor" refers to an extracellular fragment of a receptor protein preceding the first transmembrane domain of the receptor that can be secreted from a cell in soluble form. The term "soluble receptor" encompasses a molecule comprising the entire extracellular domain, or a fragment of the extracellular domain.

As used herein, the term "linker" or "linker region" refers to a linker inserted between a first polypeptide (e.g., a PVR component) and a second polypeptide (e.g., a Fc region). In some embodiments, the linker is a peptide linker. Linkers should not adversely affect the expression, secretion, or bioactivity of the polypeptides. Preferably, linkers are not antigenic and do not elicit an immune response.

The terms "selectively binds" or "specifically binds" mean that a binding agent reacts or associates more frequently, more rapidly, with greater duration, with greater affinity, or with some combination of the above to the epitope, protein, or target molecule than with alternative substances, including related and unrelated proteins. In certain embodiments "specifically binds" means, for instance, that a binding agent binds a protein or target with a $K_D$ of about 0.1 mM or less, but more usually less than about 1 µM. In certain embodiments, "specifically binds" means that a binding agent binds a target with a $K_D$ of at least about 0.1 µM or less, at least about 0.01 µM or less, or at least about 1 nM or less. Because of the sequence identity between homologous proteins in different species, specific binding can include a binding agent that recognizes a protein or target in more than one species. Likewise, because of homology within certain regions of polypeptide sequences of different proteins, specific binding can include a binding agent that recognizes more than one protein or target. It is understood that, in certain embodiments, a binding agent that specifically binds a first target may or may not specifically bind a second target. As such, "specific binding" does not necessarily require (although it can include) exclusive binding, i.e. binding to a single target. Thus, a binding agent may, in certain embodiments, specifically bind more than one target. In certain embodiments, multiple targets may be bound by the same antigen-binding site on the binding agent. For example, an antibody may, in certain instances, comprise two identical antigen-binding sites, each of which specifically binds the same epitope on two or more proteins. In certain alternative embodiments, an antibody may be bispecific and comprise at least two antigen-binding sites with differing specificities. By way of non-limiting example, a bispecific antibody may comprise one antigen-binding site that recognizes an epitope on one protein and further comprise a second, different antigen-binding site that recognizes a different epitope on a second protein. Generally, but not necessarily, reference to binding means specific binding.

The terms "polypeptide" and "peptide" and "protein" are used interchangeably herein and refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids), as well as other modifications known in the art. It is understood that, because the polypeptides of this invention may be based upon antibodies or other members of the immunoglobulin superfamily, in certain embodiments, the polypeptides can occur as single chains or as associated chains.

The terms "polynucleotide" and "nucleic acid" and "nucleic acid molecule" are used interchangeably herein and refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity may be measured using sequence comparison software or algorithms or by visual inspection. Various algorithms and software that may be used to obtain alignments of amino acid or nucleotide sequences are well-known in the art. These include, but are not limited to, BLAST, ALIGN, Megalign, BestFit, GCG Wisconsin Package, and variants thereof. In some embodiments, two nucleic acids or polypeptides of the invention are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. In some embodiments, identity exists over a region of the sequences that is at least about 10, at least about 20, at least about 40-60 residues, at least about 60-80 residues in length or any integral value there between. In some embodiments, identity exists over a longer region than 60-80 residues, such as at least about 80-100 residues, and in some embodiments the sequences are substantially identical over the full length of the sequences being compared, such as the coding region of a nucleotide sequence.

A "conservative amino acid substitution" is one in which one amino acid residue is replaced with another amino acid residue having a similar side chain Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. Generally, conservative substitutions in the sequences of the polypeptides, soluble receptors, and/or antibodies of the invention do not abrogate the binding of the polypeptide, soluble receptor, or antibody containing the amino acid sequence, to the target binding site. Methods of identifying nucleotide and amino acid conservative substitutions which do not eliminate binding are well-known in the art.

The term "vector" as used herein means a construct, which is capable of delivering, and usually expressing, one or more gene(s) or sequence(s) of interest in a host cell. Examples of vectors include, but are not limited to, viral vectors, naked DNA or RNA expression vectors, plasmid, cosmid, or phage vectors, DNA or RNA expression vectors associated with cationic condensing agents, and DNA or RNA expression vectors encapsulated in liposomes.

A polypeptide, soluble receptor, antibody, polynucleotide, vector, cell, or composition which is "isolated" is a polypeptide, soluble receptor, antibody, polynucleotide, vector, cell, or composition which is in a form not found in nature. Isolated polypeptides, soluble receptors, antibodies, polynucleotides, vectors, cells, or compositions include those which have been purified to a degree that they are no longer in a form in which they are found in nature. In some embodiments, a polypeptide, soluble receptor, antibody, polynucleotide, vector, cell, or composition which is isolated is substantially pure.

The term "substantially pure" as used herein refers to material which is at least 50% pure (i.e., free from contaminants), at least 90% pure, at least 95% pure, at least 98% pure, or at least 99% pure.

The term "immune response" as used herein includes responses from both the innate immune system and the adaptive immune system. It includes both T-cell and B-cell responses (e.g., cell-mediated and/or humoral immune responses), as well as responses from other cells of the immune system such as natural killer (NK) cells, monocytes, macrophages, etc.

The terms "cancer" and "cancerous" as used herein refer to or describe the physiological condition in mammals in which a population of cells are characterized by unregulated cell growth. Examples of cancer include, but are not limited to, carcinoma, blastoma, sarcoma, and hematologic cancers such as lymphoma and leukemia.

The terms "tumor" and "neoplasm" as used herein refer to any mass of tissue that results from excessive cell growth or proliferation, either benign (noncancerous) or malignant (cancerous) including pre-cancerous lesions.

The term "metastasis" as used herein refers to the process by which a cancer spreads or transfers from the site of origin to other regions of the body with the development of a similar cancerous lesion at the new location. A "metastatic" or "metastasizing" cell is one that loses adhesive contacts with neighboring cells and migrates via the bloodstream or lymph from the primary site of disease to invade neighboring body structures.

The terms "cancer stem cell" and "CSC" and "tumor stem cell" and "tumor initiating cell" are used interchangeably herein and refer to cells from a cancer or tumor that: (1) have extensive proliferative capacity; 2) are capable of asymmetric cell division to generate one or more types of differentiated cell progeny wherein the differentiated cells have reduced proliferative or developmental potential; and (3) are capable of symmetric cell divisions for self-renewal or self-maintenance. These properties confer on the cancer stem cells the ability to form or establish a tumor or cancer upon serial transplantation into an appropriate host (e.g., a mouse) compared to the majority of tumor cells that fail to form tumors. Cancer stem cells undergo self-renewal versus differentiation in a chaotic manner to form tumors with abnormal cell types that can change over time as mutations occur.

The terms "cancer cell" and "tumor cell" refer to the total population of cells derived from a cancer or tumor or pre-cancerous lesion, including both non-tumorigenic cells, which comprise the bulk of the cancer cell population, and tumorigenic stem cells (cancer stem cells). As used herein, the terms "cancer cell" or "tumor cell" will be modified by the term "non-tumorigenic" when referring solely to those cells lacking the capacity to renew and differentiate to distinguish those tumor cells from cancer stem cells.

The term "tumorigenic" as used herein refers to the functional features of a cancer stem cell including the properties of self-renewal (giving rise to additional tumorigenic cancer stem cells) and proliferation to generate all other tumor cells (giving rise to differentiated and thus non-tumorigenic tumor cells).

The term "tumorigenicity" as used herein refers to the ability of a random sample of cells from the tumor to form palpable tumors upon serial transplantation into appropriate hosts (e.g., mice).

The term "subject" refers to any animal (e.g., a mammal), including, but not limited to, humans, non-human primates, canines, felines, rodents, and the like, which is to be the recipient of a particular treatment. Typically, the terms "subject" and "patient" are used interchangeably herein in reference to a human subject.

The term "pharmaceutically acceptable" refers to a substance approved or approvable by a regulatory agency of the Federal or a state government or listed in the U.S. Pharmacopeia or other generally recognized pharmacopeia for use in animals, including humans.

The terms "pharmaceutically acceptable excipient, carrier or adjuvant" or "acceptable pharmaceutical carrier" refer to an excipient, carrier or adjuvant that can be administered to a subject, together with at least one binding agent (e.g., an antibody) of the present disclosure, and which does not destroy the pharmacological activity thereof and is nontoxic when administered in doses sufficient to deliver a therapeutic effect.

The terms "effective amount" or "therapeutically effective amount" or "therapeutic effect" refer to an amount of a binding agent, a soluble receptor, an antibody, polypeptide, polynucleotide, small organic molecule, or other drug effective to "treat" a disease or disorder in a subject such as, a mammal. In the case of cancer or a tumor, the therapeutically effective amount of an agent (e.g., soluble receptor or antibody) has a therapeutic effect and as such can boost the immune response, boost the anti-tumor response, increase cytolytic activity of immune cells, increase killing of tumor cells by immune cells, reduce the number of tumor cells; decrease tumorigenicity, tumorigenic frequency or tumorigenic capacity; reduce the number or frequency of cancer stem cells; reduce the tumor size; reduce the cancer cell population; inhibit or stop cancer cell infiltration into peripheral organs including, for example, the spread of cancer into soft tissue and bone; inhibit and stop tumor or cancer cell metastasis; inhibit and stop tumor or cancer cell growth; relieve to some extent one or more of the symptoms associated with the cancer; reduce morbidity and mortality; improve quality of life; or a combination of such effects.

The terms "treating" or "treatment" or "to treat" or "alleviating" or "to alleviate" refer to both (1) therapeutic measures that cure, slow down, lessen symptoms of, and/or halt progression of a diagnosed pathologic condition or disorder and (2) prophylactic or preventative measures that prevent or slow the development of a targeted pathologic condition or disorder. Thus those in need of treatment include those already with the disorder; those prone to have the disorder; and those in whom the disorder is to be prevented. In the case of cancer or a tumor, a subject is successfully "treated" according to the methods of the present invention if the patient shows one or more of the following: an increased immune response, an increased anti-tumor response, increased cytolytic activity of immune cells, increased killing of tumor cells by immune cells, a reduction in the number of or complete absence of cancer cells; a reduction in the tumor size; inhibition of or an absence of cancer cell infiltration into peripheral organs including the spread of cancer cells into soft tissue and bone; inhibition of or an absence of tumor or cancer cell metastasis; inhibition or an absence of cancer growth; relief of one or more symptoms associated with the specific cancer; reduced morbidity and mortality; improvement in quality of life; reduction in tumorigenicity; reduction in the number or frequency of cancer stem cells; or some combination of effects.

As used in the present disclosure and claims, the singular forms "a", "an" and "the" include plural forms unless the context clearly dictates otherwise.

It is understood that wherever embodiments are described herein with the language "comprising" otherwise analogous embodiments described in terms of "consisting of" and/or "consisting essentially of" are also provided. It is also understood that wherever embodiments are described herein with the language "consisting essentially of" otherwise analogous embodiments described in terms of "consisting of" are also provided.

As used herein, reference to "about" or "approximately" a value or parameter includes (and describes) embodiments that are directed to that value or parameter. For example, description referring to "about X" includes description of "X".

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

II. Binding Agents

The present invention provides agents that bind members of the immunoglobulin superfamily, particularly the PVR family. The PVR family includes, but is not limited to, poliovirus receptor (PVR), poliovirus receptor-related protein 1 (PVRL1), poliovirus receptor-related protein 2 (PVRL2), poliovirus receptor-related protein 3 (PVRL3), poliovirus receptor-related protein 4 (PVRL4), T cell immunoreceptor with Ig and ITIM domains (TIGIT), CD226, and CD96. These proteins are all generally related in both structure and function. The receptors are type I transmembrane proteins, which typically consist of an extracellular domain (ECD) containing one or more immunoglobulin (Ig)-like domains, a single transmembrane domain, and a cytoplasmic tail. The receptors mediate interactions through their N-terminal Ig-like domains, which commonly bind other Ig-like domains on an opposing cell surface (homophilic interaction), and also interact with integrins and carbohydrates (heterophilic interaction) (Wong et al., 2012, Int. J. Cell Biol.; epub).

Human poliovirus receptor (PVR) is a 70 kD protein that contains three extracellular Ig-like domains, a transmembrane domain, and a cytoplasmic tail. The Ig-like domains include an N-terminal V-type domain followed by two C2-type domains. PVR is primarily found on endothelial cells, monocytes, epithelial cells, and central nervous system cells. PVR in involved in cell-cell and cell-matrix interactions with CD226, CD96, PVRL3, and vitronectin. PVR is also known as CD155, nectin-like 5, and NECL-5.

Human poliovirus receptor-related proteins 1-4 (PVRL1-4) all have a structure similar to PVR, i.e., three Ig-like domains including an N-terminal V-type domain followed by two C2-type domains, a transmembrane domain, and a cytoplasmic tail. PVRL1 is broadly expressed on endothelial cells, epithelial cells, neuronal cells, megakaryocytes, and CD34-positive stem cells. PVRL1 functions as a receptor for herpes simplex viruses (HSV-1 and HSV-2) and is involved in the formation of cell junctions. PVRL1 is also known as CD111, nectin-1, HVEC, HLGR, and PRR1. Similar to PVRL1, PVRL2 is broadly expressed on endothelial cells, epithelial cells, neuronal cells, megakaryocytes, and CD34-positive stem cells and functions as a receptor for HSV. In addition, it is involved in the formation of cell junctions and interacts with CD226 and other PVR family members. PVRL2 is also known as CD112, nectin-2, I-WEB and PRR2. PVRL3 and PVRL4 appear to be only weakly expressed on most normal cells, however, similar to PVRL1 and PVRL2, PVRL3 and PVRL4 are involved in the formation of cell junctions. In addition, PVRL4 has been identified as a receptor of the measles virus. PVRL3 is also known as CD113 and nectin-3, while PVRL4 is also known as nectin-4, LNIR, and PRR4.

CD226 is a ~65 kD glycoprotein that contains two Ig-like domains including two C2-type domains, followed by a transmembrane domain, and a cytoplasmic tail containing an immunoreceptor tyrosine-based activation motif (ITAM). CD226 has been observed on the surface of natural killer (NK) cells, monocytes, macrophages, T-cells, megakaryocytes, and a subset of B-cells. CD226 binds PVR and PVRL2, and appears to be involved in activation of NK cells and T-cells. This receptor is also known as DNAM-1, PTA-1, and TLiSA1.

TIGIT is a 26 kD protein that contains one Ig-like V-type domain, followed by a transmembrane domain, and a cytoplasmic tail containing two immunoreceptor tyrosine-based inhibition motifs (ITIM). TIGIT has been observed on the surface of NK cells and most activated T-cells, but is low or negative on naive lymphocytes. TIGIT binds PVR, PVRL2, PVRL3, and PVRL4, and appears to have an inhibitory function on both T-cells and NK cells. This receptor is also known as VSIG9, Vstm3, and WUCAM.

CD96 is a 160 kD protein that contains three Ig-like domains including two V-type domains and one C2-type domain, followed by a transmembrane domain, and a cytoplasmic tail containing an ITIM motif. CD96 has been shown to be expressed on the surface of NK cells and T-cells. CD96 binds to PVR and it is believed that the predominant function of CD96 is to mediate adhesion of NK cells to other cells expressing PVR. However, the presence of an ITIM suggests that CD96 may also have an inhibitory function. This receptor is also known as tactile.

The full-length amino acid (aa) sequences of human PVR, PVRL1-4, TIGIT, CD226, and CD96 are known in the art and are provided herein as SEQ ID NO:1 (PVR), SEQ ID NO:2 (PVRL1), SEQ ID NO:3 (PVRL2), SEQ ID NO:4 (PVRL3), SEQ ID NO:5 (PVRL4), SEQ ID NO:6 (TIGIT), SEQ ID NO:7 (CD96), and SEQ ID NO:8 (CD226). As used herein, reference to amino acid positions corresponding to a "wild-type protein" refer to the numbering of full-length amino acid sequences including the signal sequence.

In certain embodiments, the binding agent is a polypeptide. In some embodiments, the binding agent comprises a soluble receptor. In certain embodiments, the binding agent is a soluble receptor. In certain embodiments, the binding agent is a bispecific agent. In certain embodiments, the binding agent (e.g., a soluble receptor or a polypeptide) comprises a PVR variant. As used herein, a "variant" protein comprises substitutions, deletions, and/or additions in one or more amino acids corresponding to amino acids of the wild-type protein. In some embodiments, the PVR variant comprises one or more Ig-like domains of human PVR. In certain embodiments, the PVR variant comprises an N-terminal IgV domain of human PVR, wherein the PVR variant comprises one or more amino acid substitutions as compared to wild-type PVR. In certain embodiments, the PVR variant consists essentially of an N-terminal IgV domain of human PVR, wherein the PVR variant comprises one or more amino acid substitutions as compared to wild-type PVR. In some embodiments, the PVR variant comprises an N-terminal IgV domain and one IgC2 domain of human PVR, wherein the PVR variant comprises one or more amino acid substitutions as compared to wild-type PVR. In some embodiments, the PVR variant comprises an N-terminal IgV domain and both IgC2 domains of human PVR, wherein the PVR variant comprises one or more amino acid substitutions as compared to wild-type PVR. In some embodiments, the PVR variant comprises substitutions in one or more amino acids corresponding to amino acids 40-143 of wild-type PVR. In some embodiments, the PVR variant comprises substitutions in one or more amino acids corresponding to amino acids 60-90 of wild-type PVR. In some embodiments, the PVR variant comprises substitutions in one or more amino acids corresponding to amino acids 125-133 of wild-type PVR. In some embodiments, the PVR variant comprises substitutions in one or more amino acids corresponding to amino acids 60-90 and 125-133 of wild-type PVR. In some embodiments, the PVR variant comprises substitutions in one or more amino acids corresponding to amino acids 65, 67, 72, 73, 74, 81, 82, 84, and 85 of wild-type PVR. In some embodiments, the PVR variant comprises a substitution in an amino acid corresponding to amino acid 72 of wild-type PVR. In some embodiments, the PVR variant comprises a substitution in an amino acid corresponding to amino acid 82 of wild-type PVR. In some embodiments, the PVR variant comprises substitutions in one or more amino acids corresponding to amino acids 72 and 82 of wild-type PVR. In some embodiments, the PVR variant comprises an amino acid sequence selected from the group consisting of: SEQ ID NO:18, SEQ ID NO:19, SEQ ID NO:20, and SEQ ID NO:21.

In certain embodiments, the binding agent (e.g., a soluble receptor or a polypeptide) comprises a PVRL1 variant. In some embodiments, the PVRL1 variant comprises one or more Ig-like domains of human PVRL1. In certain embodiments, the PVRL1 variant comprises an N-terminal IgV domain of human PVRL1, wherein the PVRL1 variant comprises one or more amino acid substitutions as compared to wild-type PVRL1. In certain embodiments, the PVRL1 variant consists essentially of an N-terminal IgV domain of human PVRL1, wherein the PVRL1 variant comprises one or more amino acid substitutions as compared to wild-type PVRL1. In some embodiments, the PVRL1 variant comprises an N-terminal IgV domain and one IgC2 domain of human PVRL1, wherein the PVRL1 variant comprises one or more amino acid substitutions as compared to wild-type PVRL1. In some embodiments, the PVRL1 variant comprises an N-terminal IgV domain and both IgC2 domains of human PVRL1, wherein the PVRL1 variant comprises one or more amino acid substitutions as compared to wild-type PVRL1. In some embodiments, the PVRL1 variant comprises substitutions in one or more amino acids corresponding to amino acids 41-144 of wild-type PVRL1. In some embodiments, the PVRL1 variant comprises substitutions in one or more amino acids corresponding to amino acids 61-93 of wild-type PVRL1. In some embodiments, the PVRL1 variant comprises substitutions in one or more amino acids corresponding to amino acids 126-134 of wild-type PVRL1. In some embodiments, the PVRL1 variant comprises substitutions in one or more amino acids corresponding to amino acids 61-93 and 126-134 of wild-type PVRL1.

In certain embodiments, the binding agent (e.g., a soluble receptor or a polypeptide) comprises a PVRL2 variant. In some embodiments, the PVRL2 variant comprises one or more Ig-like domains of human PVRL2. In certain embodiments, the PVRL2 variant comprises an N-terminal IgV domain of human PVRL2, wherein the PVRL2 variant comprises one or more amino acid substitutions as compared to wild-type PVRL2. In certain embodiments, the PVRL2 variant consists essentially of an N-terminal IgV domain of human PVRL2, wherein the PVRL2 variant comprises one or more amino acid substitutions as compared to wild-type PVRL2. In some embodiments, the PVRL2 variant comprises an N-terminal IgV domain and one IgC2 domain of human PVRL2, wherein the PVRL2 variant comprises one or more amino acid substitutions as compared to wild-type PVRL2. In some embodiments, the PVRL2 variant comprises an N-terminal IgV domain and both IgC2 domains of human PVRL2, wherein the PVRL2 variant comprises one or more amino acid substitutions as compared to wild-type PVRL2. In some embodiments, the PVRL2 variant comprises substitutions in one or more amino acids corresponding to amino acids 45-160 of wild-type PVRL2. In some embodiments, the PVRL2 variant comprises substitutions in one or more amino acids corresponding to amino acids 64-97 of wild-type PVRL2. In some embodiments, the PVRL2 variant comprises substitutions in one or more amino acids corresponding to amino acids 142-150 of wild-type PVRL2. In some embodiments, the PVRL2 variant comprises substitutions in one or more amino acids corresponding to amino acids 64-97 and 142-150 of wild-type PVRL2.

In certain embodiments, the binding agent (e.g., a soluble receptor or a polypeptide) comprises a PVRL3 variant. In some embodiments, the PVRL3 variant comprises one or more Ig-like domains of human PVRL3. In certain embodiments, the PVRL3 variant comprises an N-terminal IgV domain of human PVRL3, wherein the PVRL3 variant comprises one or more amino acid substitutions as compared to wild-type PVRL3. In certain embodiments, the PVRL3 variant consists essentially of an N-terminal IgV domain of human PVRL3, wherein the PVRL3 variant comprises one or more amino acid substitutions as compared to wild-type PVRL3. In some embodiments, the PVRL3 variant comprises an N-terminal IgV domain and one IgC2 domain of human PVRL3, wherein the PVRL3 variant comprises one or more amino acid substitutions as compared to wild-type PVRL3. In some embodiments, the PVRL3 variant comprises an N-terminal IgV domain and both IgC2 domains of human PVRL3, wherein the PVRL3 variant comprises one or more amino acid substitutions as compared to wild-type PVRL3. In some embodiments, the PVRL3 variant comprises substitutions in one or more amino acids corresponding to amino acids 68-168 of wild-type PVRL3. In some embodiments, the PVRL3 variant comprises substitutions in one or more amino acids corresponding to amino acids 86-117 of wild-type PVRL3. In some embodiments, the PVRL3 variant comprises substitutions in one or more amino acids corresponding to amino acids 150-158 of wild-type PVRL3. In some embodiments, the PVRL3 variant comprises substitutions in one or more amino acids corresponding to amino acids 86-117 and 150-158 of wild-type PVRL3.

In certain embodiments, the binding agent (e.g., a soluble receptor or a polypeptide) comprises a PVRL4 variant. In some embodiments, the PVRL4 variant comprises one or more Ig-like domains of human PVRL4. In certain embodiments, the PVRL4 variant comprises an N-terminal IgV domain of human PVRL4, wherein the PVRL4 variant comprises one or more amino acid substitutions as compared to wild-type PVRL4. In certain embodiments, the PVRL4 variant consists essentially of an N-terminal IgV domain of human PVRL4, wherein the PVRL4 variant comprises one or more amino acid substitutions as compared to wild-type PVRL4. In some embodiments, the PVRL4 variant comprises an N-terminal IgV domain and one IgC2 domain of human PVRL4, wherein the PVRL4 variant comprises one or more amino acid substitutions as compared to wild-type PVRL4. In some embodiments, the PVRL4 variant comprises an N-terminal IgV domain and both IgC2 domains of human PVRL4, wherein the PVRL4 variant comprises one or more amino acid substitutions as compared to wild-type PVRL4. In some embodiments, the PVRL4 variant comprises substitutions in one or more amino acids corresponding to amino acids 42-147 of wild-type PVRL4. In some embodiments, the PVRL4 variant comprises substitutions in one or more amino acids corresponding to amino acids 62-94 of wild-type PVRL4. In some embodiments, the PVRL4 variant comprises substitutions in one or more amino acids corresponding to amino acids 129-137 of wild-type PVRL4. In some embodiments, the PVRL4 variant comprises substitutions in one or more amino acids corresponding to amino acids 62-94 and 129-137 of wild-type PVRL4.

The extracellular domains (ECD) for PVR, PVRL1, PVRL2, PVRL3, PVRL4, TIGIT, CD96, and CD226 are provided as SEQ ID NOs:9-16 (without predicted signal sequences). Those of skill in the art may differ in their understanding of the exact amino acids corresponding to the various ECD domains. Thus, the N-terminus and/or C-terminus of the ECDs described herein may extend or be shortened by 1, 2, 3, 4, 5, 6, 7, 8, 9, 10 or more amino acids. This is also true for the individual Ig-type domains within the ECDs.

Human TIGIT and human CD96 are inhibitory receptors which mediate their activity via their ITIMs and are believed to have the ability to inhibit immune responses. In contrast, human CD226 is an activation receptor which mediates its activity via an ITAM and is believed to have the ability to activate immune responses. TIGIT, CD96 and CD226 are all expressed on NK cells and T-cells. All three receptors have been shown to bind PVR, with TIGIT having the highest affinity for PVR as compared to CD96 and CD226. In many situations, it appears that the inhibitory effects of TIGIT are dominant and an immune response to antigenic stimulation (e.g., a tumor, a virus, an infection) is reduced or suppressed. Without being bound by theory, it is proposed that through the manipulation of the inhibitory receptors TIGIT and/or CD96, that a strong immune response could be activated and/or increased. For example, a strong immune response could be achieved using binding agents that specifically interact with TIGIT, but do not activate signaling (i.e., "blocking agents"), wherein the agents do not bind and/or affect the activation of CD226, allowing for an increase in the activity of, for example, NK cells and/or T-cells. The immune response could be strengthened if the binding agents specifically interact with both TIGIT and CD96, without activating any inhibitory signaling from these molecules. This would allow CD226 signaling to be dominant, resulting in a strong or stronger immune response.

Thus, in some embodiments, the binding agent (e.g., a soluble receptor) interferes with the interaction between PVR and TIGIT. In some embodiments, the binding agent interferes with the interaction between PVR and TIGIT and the interaction between PVR and CD96. In some embodiments, the binding agent interferes with the interaction between PVR and CD96. In some embodiments, the binding agent interferes with the interaction between PVR and TIGIT, but does not interfere with the interaction between PVR and CD226. In some embodiments, the binding agent interferes with the interaction between PVR and TIGIT and the interaction between PVR and CD96, but does not interfere with the interaction between PVR and CD226. In some embodiments, the binding agent interferes with the interaction between PVR and CD96, but does not interfere with the interaction between PVR and CD226. In some embodiments, the binding agent comprises a soluble receptor comprising a PVR variant, wherein the binding agent interferes with the interaction between PVR and TIGIT, the interaction between PVR and CD96, and does not interfere with the interaction between PVR and CD226. In some embodiments, the binding agent comprises a soluble receptor comprising a PVRL2 variant, wherein the binding agent interferes with the interaction between PVRL2 and TIGIT and does not interfere with the interaction between PVRL2 and CD226.

In some embodiments, the binding agent (e.g., a soluble receptor) specifically binds the extracellular domain of human TIGIT. In some embodiments, the binding agent specifically binds the extracellular domain of human CD96. In some embodiments, the binding agent specifically binds the extracellular domain of human TIGIT and binds the extracellular domain of CD96. In some embodiments, the binding agent specifically binds the extracellular domain of human TIGIT and does not bind (or binds weakly to) the extracellular domain of human CD226. In some embodiments, the binding agent specifically binds the extracellular domain of human CD96 and does not bind (or binds weakly to) the extracellular domain of CD226. In some embodiments, the binding agent specifically binds the extracellular domain of human TIGIT and binds the extracellular domain of CD96, and does not bind (or binds weakly to) the extracellular domain of human CD226. In some embodiments, the binding agent comprises a soluble receptor comprising a PVR variant, wherein the binding agent specifically binds TIGIT and CD96, and does not bind (or binds weakly to) CD226. In some embodiments, the binding agent comprises a soluble receptor comprising a PVRL2 variant, wherein the binding agent specifically binds TIGIT and does not bind (or binds weakly to) CD226.

In some embodiments, the binding agent (e.g., a soluble receptor) specifically binds the extracellular domain of human TIGIT and inhibits or interferes with the interaction (e.g., binding) between PVR and TIGIT. In some embodiments, the binding agent specifically binds the extracellular domain of human TIGIT and the extracellular domain of human CD96 and inhibits or interferes with the interaction (e.g., binding) between PVR and TIGIT and the interaction (e.g., binding) between PVR and CD96. In some embodiments, the binding agent specifically binds the extracellular domain of human TIGIT and inhibits or interferes with the interaction (e.g., binding) between PVR and TIGIT, but does not bind (or binds weakly to) the extracellular domain of human CD226 and does not inhibit or interfere with the interaction (e.g., binding) between PVR and CD226. In some embodiments, the binding agent specifically binds the extracellular domain of human TIGIT and the extracellular domain of human CD96 and inhibits or interferes with the interaction (e.g., binding) between PVR and TIGIT and the interaction (e.g., binding) between PVR and CD96, but does not bind (or binds weakly to) the extracellular domain of human CD226 and does not inhibit or interfere with the interaction (e.g., binding) between PVR and CD226. In some embodiments, the binding agent comprises a soluble receptor comprising a PVR variant, wherein the soluble receptor comprising a PVR variant specifically binds the extracellular domain of human TIGIT and the extracellular domain of human CD96 and inhibits or interferes with the interaction (e.g., binding) between PVR and TIGIT and the interaction (e.g., binding) between PVR and CD96, but does not bind (or binds weakly to) the extracellular domain of human CD226 and does not inhibit or interfere with the interaction (e.g., binding) between PVR and CD226. In some embodiments, the binding agent comprises a soluble receptor comprising a PVRL2 variant, wherein the soluble receptor comprising a PVRL2 variant specifically binds the extracellular domain of human TIGIT and inhibits or interferes with the interaction (e.g., binding) between PVRL2 and TIGIT and the interaction (e.g., binding) between PVR and TIGIT, but does not bind (or binds weakly to) the extracellular domain of human CD226 and does not inhibit or interfere with the interaction (e.g., binding) between PVR and CD226.

In some embodiments, the binding agent (e.g., a soluble receptor) comprises a PVR variant that specifically binds the extracellular domain of human TIGIT, but does not bind (or binds weakly to) the extracellular domain of human CD226. In some embodiments, the binding agent (e.g., a soluble receptor) comprises a PVR variant that specifically binds the extracellular domain of human TIGIT and specifically binds the extracellular domain of human CD96, but does not bind (or binds weakly to) the extracellular domain of human CD226. In some embodiments, the PVR variant is a PVR variant described herein. In some embodiments, the PVR variant comprises a sequence selected from the group consisting of SEQ ID NO:18, SEQ ID NO:19, SEQ ID NO:20, and SEQ ID NO:21.

In some embodiments, the binding agent (e.g., a soluble receptor or a polypeptide) comprises a PVRL2 variant that specifically binds the extracellular domain of human TIGIT, but does not bind (or binds weakly to) the extracellular domain of human CD226. In some embodiments, the PVRL2 variant is a PVRL2 variant described herein. In some embodiments, the PVRL2 variant comprises SEQ ID NO:38.

In some embodiments, the binding agent specifically binds the extracellular domain of human TIGIT and inhibits or interferes with the interaction (e.g., binding) between PVRL2 and TIGIT. In some embodiments, the binding agent specifically binds the extracellular domain of human TIGIT and inhibits or interferes with the interaction (e.g., binding) between PVRL2 and TIGIT, but does not bind (or binds weakly to) the extracellular domain of human CD226 and does not inhibit or interfere with the interaction (e.g., binding) between PVRL2 and CD226.

In some embodiments, the binding agent (e.g., a soluble receptor) comprises a PVRL3 variant that specifically binds the extracellular domain of human TIGIT. In some embodiments, the binding agent (e.g., a soluble receptor) comprises a PVRL4 variant that specifically binds the extracellular domain of human TIGIT.

In some embodiments, the binding agent specifically binds the extracellular domain of human TIGIT and inhibits or interferes with the interaction (e.g., binding) between PVRL3 and TIGIT. In some embodiments, the binding agent specifically binds the extracellular domain of human TIGIT and inhibits or interferes with the interaction (e.g., binding) between PVRL4 and TIGIT.

In some embodiments, the binding agent is a TIGIT-binding agent comprising one or more Ig-like domains of a variant human PVR. In some embodiments, the binding agent is a CD96-binding agent comprising one or more Ig-like domains of a variant human PVR. In some embodiments, the binding agent is a TIGIT and CD96-binding agent comprising one or more Ig-like domains of a variant human PVR. In some embodiments, the TIGIT-binding agent comprises a variant human PVR and does not bind (or binds weakly to) CD226.

In some embodiments, the binding agent (e.g., a soluble receptor) is a fusion protein. As used herein, a "fusion protein" is a hybrid protein expressed by a nucleic acid molecule comprising nucleotide sequences of at least two genes. In certain embodiments, the binding agent, such as a soluble receptor or a polypeptide, further comprises a non-PVR polypeptide. In some embodiments, soluble receptors may include a PVR family member ECD or fragment thereof (e.g., Ig-like domain) linked to non-PVR polypeptides including, but not limited to, a human Fc region, protein tags (e.g., myc, FLAG, GST), other endogenous proteins or protein fragments, or any other useful protein sequences including any linker region between an ECD and a second polypeptide. In certain embodiments, the non-PVR polypeptide comprises a human Fc region. In certain embodiments, the non-PVR polypeptide consists essentially of a human Fc region. In certain embodiments, the non-PVR polypeptide consists of a human Fc region. The Fc region can be obtained from any of the classes of immunoglobulin, IgG, IgA, IgM, IgD and IgE. In some embodiments, the Fc region is a human IgG1 Fc region. In some embodiments, the Fc region is a human IgG2 Fc region. In some embodiments, the Fc region is a wild-type Fc region. In some embodiments, the Fc region is a wild-type Fc region containing natural amino acid variations. In some embodiments, the Fc region is a mutated or modified Fc region. In some embodiments, the Fc region is truncated at the N-terminal end by 1, 2, 3, 4, 5, 6, 7, 8, 9, 10, or more amino acids, (e.g., in the hinge domain). In some embodiments, the Fc region is truncated at the C-terminal end by one or more amino acids, (e.g., missing the C-terminal lysine). In some embodiments, an amino acid in the hinge domain is changed to hinder undesirable disulfide bond formation. In some embodiments, a cysteine is replaced with a different amino acid to hinder undesirable disulfide bond formation. In some embodiments, a cysteine is replaced with a serine to hinder undesirable disulfide bond formation. In some embodiments, the Fc region is modified to promote formation of heteromultimers or heterodimeric molecules. In certain embodiments, the non-PVR polypeptide comprises SEQ ID NO:26, SEQ ID NO:27, SEQ ID NO:28, SEQ ID NO:29, SEQ ID NO:30, SEQ ID NO:31, SEQ ID NO:43, SEQ ID NO:44, SEQ ID NO:45, SEQ ID NO:46, SEQ ID NO:47, or SEQ ID NO:48. In certain embodiments, the non-PVR polypeptide consists essentially of SEQ ID NO:26, SEQ ID NO:27, SEQ ID NO:28, SEQ ID NO:29, SEQ ID NO:30, SEQ ID NO:31, SEQ ID NO:43, SEQ ID NO:44, SEQ ID NO:45, SEQ ID NO:46, SEQ ID NO:47, or SEQ ID NO:48.

In certain embodiments, the binding agent (e.g., a soluble receptor) is a fusion protein comprising at least a fragment of a PVR variant ECD (or PVRL1-4 variant ECDs) and a Fc region. In some embodiments, the C-terminus of the PVR variant ECD (or fragment thereof) is linked to the N-terminus of the immunoglobulin Fc region. In some embodiments, the PVR variant ECD (or fragment thereof) is directly linked to the Fc region (i.e. without an intervening peptide linker). In some embodiments, the PVR variant ECD (or fragment thereof) is linked to the Fc region via a peptide linker.

As used herein, the term "linker" refers to a linker inserted between a first polypeptide (e.g., a PVR variant ECD or a fragment thereof) and a second polypeptide (e.g., a Fc region). In some embodiments, the linker is a peptide linker. Linkers should not adversely affect the expression, secretion, or bioactivity of the fusion protein. Linkers should not be antigenic and should not elicit an immune response. Suitable linkers are known to those of skill in the art and often include mixtures of glycine and serine residues and often include amino acids that are sterically unhindered. Other amino acids that can be incorporated into useful linkers include threonine and alanine residues. Linkers can range in length, for example from 1-50 amino acids in length, 1-22 amino acids in length, 1-10 amino acids in length, 1-5 amino acids in length, or 1-3 amino acids in length. Linkers may include, but are not limited to, SerGly, GGSG, GSGS, GGGS, S(GGS)n where n is 1-7, GRA, poly(Gly), poly(Ala), ESGGGGVT (SEQ ID NO:33), LESGGGGVT (SEQ ID NO:34), GRAQVT (SEQ ID NO:35), WRAQVT (SEQ ID NO:36), and ARGRAQVT (SEQ ID NO:37). As used herein, a linker is an intervening peptide sequence that does not include amino acid residues from either the C-terminus of the first polypeptide (e.g., a PVR variant ECD or portion thereof) or the N-terminus of the second polypeptide (e.g., a Fc region).

In some embodiments, the binding agent is a fusion protein comprising a first polypeptide comprising SEQ ID NO:18, SEQ ID NO:19, SEQ ID NO:20, SEQ ID NO:21, or SEQ ID NO:38, and a second polypeptide comprising SEQ ID NO:26, SEQ ID NO:27, SEQ ID NO:28, SEQ ID NO:29, SEQ ID NO:30, SEQ ID NO:31, SEQ ID NO:43, SEQ ID NO:44, SEQ ID NO:45, SEQ ID NO:46, SEQ ID NO:47, or SEQ ID NO:48. In some embodiments, the binding agent is a fusion protein comprising a first polypeptide comprising SEQ ID NO:18, SEQ ID NO:19, SEQ ID NO:20, SEQ ID NO:21, or SEQ ID NO:38, and a second polypeptide comprising SEQ ID NO:26, SEQ ID NO:27, or SEQ ID NO:28. In some embodiments, the binding agent is a fusion protein comprising a first polypeptide comprising SEQ ID NO:18, SEQ ID NO:19, SEQ ID NO:20, SEQ ID NO:21, or SEQ ID NO:38, and a second polypeptide comprising SEQ ID NO:29, SEQ ID NO:43, or SEQ ID NO:44. In some embodiments, the binding agent is a fusion protein comprising a first polypeptide comprising SEQ ID NO:18, SEQ ID NO:19, SEQ ID NO:20, SEQ ID NO:21, or SEQ ID NO:38, and a second polypeptide comprising SEQ ID NO:30. In some embodiments, the binding agent is a fusion protein comprising a first polypeptide comprising SEQ ID NO:18, SEQ ID NO:19, SEQ ID NO:20, SEQ ID NO:21, or SEQ ID NO:38, and a second polypeptide comprising SEQ ID NO:31. In some embodiments, the binding agent is a fusion protein comprising a first polypeptide comprising SEQ ID NO:18, SEQ ID NO:19, SEQ ID NO:20, SEQ ID NO:21, or SEQ ID NO:38, and a second polypeptide comprising SEQ ID NO:45 or SEQ ID NO:46. In some embodiments, the binding agent is a fusion protein comprising a first polypeptide comprising SEQ ID NO:18, SEQ ID NO:19, SEQ ID NO:20, SEQ ID NO:21, or SEQ ID NO:38, and a second polypeptide comprising SEQ ID NO:47 or SEQ ID NO:48. In some embodiments, the binding agent is a fusion protein comprising a first polypeptide comprising SEQ ID NO:18 and a second polypeptide comprising SEQ ID NO:26, SEQ ID NO:27, SEQ ID NO:28, SEQ ID NO:29, SEQ ID NO:30, SEQ ID NO:31, SEQ ID NO:43, SEQ ID NO:44, SEQ ID NO:45, SEQ ID NO:46, SEQ ID NO:47, or SEQ ID NO:48. In some embodiments, the binding agent is a fusion protein comprising a first polypeptide comprising SEQ ID NO:19 and a second polypeptide comprising SEQ ID NO:26, SEQ ID NO:27, SEQ ID NO:28, SEQ ID NO:29, SEQ ID NO:30, SEQ ID NO:31, SEQ ID NO:43, SEQ ID NO:44, SEQ ID NO:45, SEQ ID NO:46, SEQ ID NO:47, or SEQ ID NO:48. In some embodiments, the binding agent is a fusion protein comprising a first polypeptide comprising SEQ ID NO:20 and a second polypeptide comprising SEQ ID NO:26, SEQ ID NO:27, SEQ ID NO:28, SEQ ID NO:29, SEQ ID NO:30, SEQ ID NO:31, SEQ ID NO:43, SEQ ID NO:44, SEQ ID NO:45, SEQ ID NO:46, SEQ ID NO:47, or SEQ ID NO:48. In some embodiments, the binding agent is a fusion protein comprising a first polypeptide comprising SEQ ID NO:21 and a second polypeptide comprising SEQ ID NO:26, SEQ ID NO:27, SEQ ID NO:28, SEQ ID NO:29, SEQ ID NO:30, SEQ ID NO:31, SEQ ID NO:43, SEQ ID NO:44, SEQ ID NO:45, SEQ ID NO:46, SEQ ID NO:47, or SEQ ID NO:48.

In some embodiments, the binding agent comprises a first polypeptide comprising SEQ ID NO:18, SEQ ID NO:19, SEQ ID NO:20, SEQ ID NO:21, or SEQ ID NO:38, and a second polypeptide comprising SEQ ID NO:26, SEQ ID NO:27, SEQ ID NO:28, SEQ ID NO:29, SEQ ID NO:30, SEQ ID NO:31, SEQ ID NO:43, SEQ ID NO:44, SEQ ID NO:45, SEQ ID NO:46, SEQ ID NO:47, or SEQ ID NO:48, wherein the first polypeptide is directly linked to the second polypeptide. In some embodiments, the binding agent comprises a first polypeptide comprising SEQ ID NO:18, SEQ ID NO:19, SEQ ID NO:20, or SEQ ID NO:21, and a second polypeptide comprising SEQ ID NO:30 or SEQ ID NO:31, wherein the first polypeptide is directly linked to the second polypeptide.

In some embodiments, the binding agent comprises a first polypeptide comprising SEQ ID NO:18, SEQ ID NO:19, SEQ ID NO:20, SEQ ID NO:21, or SEQ ID NO:38, and a second polypeptide comprising SEQ ID NO:26, SEQ ID NO:27, SEQ ID NO:28, SEQ ID NO:29, SEQ ID NO:30, SEQ ID NO:31, SEQ ID NO:43, SEQ ID NO:44, SEQ ID NO:45, SEQ ID NO:46, SEQ ID NO:47, or SEQ ID NO:48, wherein the first polypeptide is connected to the second polypeptide by a linker. In some embodiments, the binding agent comprises a first polypeptide comprising SEQ ID NO:18, SEQ ID NO:19, SEQ ID NO:20, or SEQ ID NO:21, and a second polypeptide comprising SEQ ID NO:30 or SEQ ID NO:31, wherein the first polypeptide is connected to the second polypeptide by a linker.

In some embodiments, the binding agent comprises a first polypeptide comprising SEQ ID NO:19 or SEQ ID NO:21 and a second polypeptide comprising SEQ ID NO:26, SEQ ID NO:27, SEQ ID NO:28, SEQ ID NO:29, SEQ ID NO:30, SEQ ID NO:31, SEQ ID NO:43, SEQ ID NO:44, SEQ ID NO:45, SEQ ID NO:46, SEQ ID NO:47, or SEQ ID NO:48, wherein the first polypeptide is directly linked to the second polypeptide. In some embodiments, the binding agent comprises a first polypeptide comprising SEQ ID NO:19 or SEQ ID NO:21 and a second polypeptide comprising SEQ ID NO:30 or SEQ ID NO:31, wherein the first polypeptide is directly linked to the second polypeptide.

In some embodiments, the binding agent comprises a first polypeptide comprising SEQ ID NO:19 or SEQ ID NO:21 and a second polypeptide comprising SEQ ID NO:26, SEQ ID NO:27, SEQ ID NO:28, SEQ ID NO:29, SEQ ID NO:30, SEQ ID NO:31, SEQ ID NO:43, SEQ ID NO:44, SEQ ID NO:45, SEQ ID NO:46, SEQ ID NO:47, or SEQ ID NO:48, wherein the first polypeptide is connected to the second polypeptide by a linker. In some embodiments, the binding agent comprises a first polypeptide comprising SEQ ID NO:19 or SEQ ID NO:21 and a second polypeptide comprising SEQ ID NO:30 or SEQ ID NO:31, wherein the first polypeptide is connected to the second polypeptide by a linker.

In some embodiments, the binding agent comprises a first polypeptide that is at least 80% identical to SEQ ID NO:17, SEQ ID NO:18, SEQ ID NO:19, SEQ ID NO:20, SEQ ID NO:21, or SEQ ID NO:38, and a second polypeptide comprising SEQ ID NO:26, SEQ ID NO:27, SEQ ID NO:28, SEQ ID NO:29, SEQ ID NO:30, SEQ ID NO:31, SEQ ID NO:43, SEQ ID NO:44, SEQ ID NO:45, SEQ ID NO:46, SEQ ID NO:47, or SEQ ID NO:48, wherein the first polypeptide is directly linked to the second polypeptide. In some embodiments, the first polypeptide is at least 85%, at least 90%, at least 95% identical to SEQ ID NO:17, SEQ ID NO:18, SEQ ID NO:19, SEQ ID NO:20, SEQ ID NO:21, or SEQ ID NO:38.

In some embodiments, the binding agent comprises a first polypeptide that is at least 80% identical to SEQ ID NO:17, SEQ ID NO:18, SEQ ID NO:19, SEQ ID NO:20, SEQ ID NO:21, or SEQ ID NO:38 and a second polypeptide comprising SEQ ID NO:26, SEQ ID NO:27, SEQ ID NO:28, SEQ ID NO:29, SEQ ID NO:30, SEQ ID NO:31, SEQ ID NO:43, SEQ ID NO:44, SEQ ID NO:45, SEQ ID NO:46, SEQ ID NO:47, or SEQ ID NO:48, wherein the first polypeptide is connected to the second polypeptide by a linker. In some embodiments, the first polypeptide is at least 85%, at least 90%, at least 95% identical to SEQ ID NO:17, SEQ ID NO:18, SEQ ID NO:19, SEQ ID NO:20, SEQ ID NO:21, or SEQ ID NO:38.

Receptor proteins generally contain a signal sequence that directs the transport of the proteins. Signal sequences (also referred to as signal peptides or leader sequences) are located at the N-terminus of nascent polypeptides. They target the polypeptide to the endoplasmic reticulum and the proteins are sorted to their destinations, for example, to the inner space of an organelle, to an interior membrane, to the cell outer membrane, or to the cell exterior via secretion. Most signal sequences are cleaved from the protein by a signal peptidase after the proteins are transported to the endoplasmic reticulum. The cleavage of the signal sequence from the polypeptide usually occurs at a specific site in the amino acid sequence and is dependent upon amino acid residues within the signal sequence. Although there is usually one specific cleavage site, more than one cleavage site may be recognized and/or used by a signal peptidase resulting in a non-homogenous N-terminus of the polypeptide. For example, the use of different cleavage sites within a signal sequence can result in a polypeptide expressed with different N-terminal amino acids. Accordingly, in some embodiments, the polypeptides as described herein may comprise a mixture of polypeptides with different N-termini. In some embodiments, the N-termini differ in length by 1, 2, 3, 4, 5, 6, 7, 8, 9, 10, or more amino acids. In some embodiments, the N-termini differ in length by 1, 2, 3, 4, or 5 amino acids. In some embodiments, the polypeptide is substantially homogeneous, i.e., the polypeptides have the same N-terminus. In some embodiments, the signal sequence of the polypeptide comprises one or more (e.g., one, two, three, four, five, six, seven, eight, nine, ten, etc.) amino acid substitutions and/or deletions. In some embodiments, the signal sequence of the polypeptide comprises amino acid substitutions and/or deletions that allow one cleavage site to be dominant, thereby resulting in a substantially homogeneous polypeptide with one N-terminus. In some embodiments, the signal sequence of the polypeptide is not a native (e.g., PVR family member) signal sequence.

Those skilled in the art will appreciate that some of the binding agents of this invention will comprise fusion proteins in which at least a portion of the Fc region has been deleted or otherwise altered so as to provide desired biochemical characteristics, such as reduced serum half-life, increased serum half-life, or increased target cell localization, when compared with a fusion protein of approximately the same immunogenicity comprising a native or unaltered Fc region. Modifications to the Fc region may include additions, deletions, or substitutions of one or more amino acids in one or more domains. The modified fusion proteins disclosed herein may comprise alterations or modifications to one or more of the two heavy chain constant domains (CH2 or CH3) or to the hinge region. In other embodiments, the entire CH2 domain may be removed (ΔCH2 constructs). In some embodiments, the omitted constant region domain is replaced by a short amino acid spacer (e.g., 10 aa residues) that provides some of the molecular flexibility typically imparted by the absent constant region domain.

In some embodiments, the modified fusion protein is engineered to link the CH3 domain directly to the hinge region or to the first polypeptide. In other embodiments, a peptide spacer is inserted between the hinge region of the first polypeptide and the modified CH2 and/or CH3 domains. For example, constructs may be expressed wherein the CH2 domain has been deleted and the remaining CH3 domain (modified or unmodified) is joined to the hinge region or first polypeptide with a 5-20 amino acid spacer. Such a spacer may be added to ensure that the regulatory elements of the constant domain remain free and accessible or that the hinge region remains flexible. However, it should be noted that amino acid spacers may, in some cases, prove to be immunogenic and elicit an unwanted immune response against the construct. Accordingly, in certain embodiments, any spacer added to the construct will be relatively non-immunogenic so as to maintain the desired biological qualities of the fusion protein.

In some embodiments, the modified fusion protein may have only a partial deletion of a constant domain or substitution of a few or even a single amino acid. For example, the mutation of a single amino acid in selected areas of the CH2 domain may be enough to substantially reduce Fc binding and thereby increase target cell localization. Similarly, it may be desirable to simply delete the part of one or more constant region domains that control a specific effector function (e.g., complement C1q binding). Such partial deletions of the constant regions may improve selected characteristics of the binding agent (e.g., serum half-life) while leaving other desirable functions associated with the subject constant region domain intact. Moreover, as alluded to above, the constant regions of the disclosed fusion proteins may be modified through the mutation or substitution of one or more amino acids that enhances the profile of the resulting construct. In this respect it may be possible to disrupt the activity provided by a conserved binding site (e.g., Fc binding) while substantially maintaining the configuration and immunogenic profile of the modified fusion protein. In certain embodiments, the modified fusion protein comprises the addition of one or more amino acids to the constant region to enhance desirable characteristics such as decreasing or increasing effector function, or provides for more cytotoxin or carbohydrate attachment sites.

It is known in the art that the constant region mediates several effector functions. For example, binding of the C1 component of complement to the Fc region of IgG or IgM antibodies (bound to antigen) activates the complement system. Activation of complement is important in the opsonization and lysis of cell pathogens. The activation of complement also stimulates the inflammatory response and can also be involved in autoimmune hypersensitivity. In addition, the Fc region can bind to a cell expressing a Fc receptor (FcR). There are a number of Fc receptors which are specific for different classes of antibody, including IgG (gamma receptors), IgE (epsilon receptors), IgA (alpha receptors) and IgM (mu receptors).

Thus, in some embodiments, the modified fusion protein provides for altered effector functions that, in turn, affect the biological profile of the administered agent. For example, in some embodiments, the deletion or inactivation (through point mutations or other means) of a constant region domain may reduce Fc receptor binding of the circulating modified agent, thereby increasing target cell localization. In other embodiments, the constant region modifications increase or reduce the serum half-life of the agent. In some embodiments, the constant region is modified to eliminate disulfide linkages or oligosaccharide attachment sites.

In certain embodiments, a modified fusion protein does not have one or more effector functions normally associated with an Fc region. In some embodiments, the agent has no ADCC activity, and/or no CDC activity. In certain embodiments, the agent does not bind to a Fc receptor and/or complement factors. In certain embodiments, the agent has no effector function.

This invention also encompasses heterodimeric molecules. Generally the heterodimeric molecule comprises two polypeptides. In some embodiments, the heterodimeric molecule is capable of binding at least two targets. The targets may be, for example, two different receptors on a single cell or two different targets on two separate cells. Thus, in some embodiments, one polypeptide of the heterodimeric molecule comprises a polypeptide described herein (e.g., binds TIGIT) and one polypeptide of the heterodimeric molecule is an antibody. In some embodiments, the heterodimeric molecule is capable of binding one target and also comprises a "non-binding" function. Thus in some embodiments, one polypeptide of the heterodimeric molecule comprises a polypeptide described herein (e.g., binds TIGIT) and one polypeptide of the heterodimeric molecule is an immune response stimulating agent. As used herein, the phrase "immune response stimulating agent" is used in the broadest sense and refers to a substance that directly or indirectly stimulates the immune system by inducing activation or increasing activity of any of the immune system's components. For example, immune response stimulating agents include cytokines, as well as various antigens including tumor antigens, and antigens derived from pathogens. In some embodiments, the immune response stimulating agent includes, but is not limited to, a colony stimulating factor (e.g., granulocyte-macrophage colony stimulating factor (GM-CSF), macrophage colony stimulating factor (M-CSF), granulocyte colony stimulating factor (G-CSF), stem cell factor (SCF)), an interleukin (e.g., IL-1, IL2, IL-3, IL-7, IL-12, IL-15, IL-18), an antibody that blocks immunosuppressive functions (e.g., an anti-CTLA4 antibody, anti-CD28 antibody, anti-CD3 antibody), a toll-like receptor (e.g., TLR4, TLR7, TLR9), or a member of the B7 family (e.g., CD80, CD86).

In some embodiments, the heterodimeric molecule can bind a first target, (e.g., TIGIT) as well as a second target, such as an effector molecule on a leukocyte (e.g., CD2, CD3, CD28, or CD80) or a Fc receptor (e.g., CD64, CD32, or CD16) so as to elicit a stronger cellular immune response.

In some embodiments, a heterodimeric molecule has enhanced potency as compared to an individual agent. It is known to those of skill in the art that any agent (e.g., a soluble receptor or a cytokine) may have unique pharmacokinetics (PK) (e.g., circulating half-life). In some embodiments, a heterodimeric molecule has the ability to synchronize the PK of two active agents and/or polypeptides wherein the two individual agents and/or polypeptides have different PK profiles. In some embodiments, a heterodimeric molecule has the ability to concentrate the actions of two agents and/or polypeptides in a common area (e.g., a tumor and/or tumor environment). In some embodiments, a heterodimeric molecule has the ability to concentrate the actions of two agents and/or polypeptides to a common target (e.g., a tumor or a tumor cell). In some embodiments, a heterodimeric molecule has the ability to target the actions of two agents and/or polypeptides to more than one biological pathway or more than one aspect of the immune response. In some embodiments, the heterodimeric molecule has decreased toxicity and/or side effects than either of the agents and/or polypeptides alone. In some embodiments, the heterodimeric molecule has decreased toxicity and/or side effects as compared to a mixture of the two individual agents and/or polypeptides. In some embodiments, the heterodimeric molecule has an increased therapeutic index. In some embodiments, the heterodimeric molecule has an increased therapeutic index as compared to a mixture of the two individual agents and/or polypeptides or the agents and/or polypeptides as single agents.

In some embodiments, the binding agent is a multidimeric molecule which comprises a first CH3 domain and a second CH3 domain, each of which is modified to promote formation of heteromultimers or heterodimers. In some embodiments, the first and second CH3 domains are modified using a knobs-into-holes technique. In some embodiments, the first and second CH3 domains comprise changes in amino acids that result in altered electrostatic interactions. In some embodiments, the first and second CH3 domains comprise changes in amino acids that result in altered hydrophobic/ hydrophilic interactions (see, for example, U.S. Patent App. Publication No. 2011/0123532).

In some embodiments, the binding agent (e.g., soluble receptor or polypeptide) is a heterodimeric molecule which comprises heavy chain constant regions selected from the group consisting of: (a) a first human IgG1 constant region, wherein the amino acids at positions corresponding to positions 253 and 292 of SEQ ID NO:39 are replaced with glutamate or aspartate, and a second human IgG1 constant region, wherein the amino acids at positions corresponding to 240 and 282 of SEQ ID NO:39 are replaced with lysine; (b) a first human IgG2 constant region, wherein the amino acids at positions corresponding to positions 249 and 288 of SEQ ID NO:40 are replaced with glutamate or aspartate, and a second human IgG2 constant region wherein the amino acids at positions corresponding to positions 236 and 278 of SEQ ID NO:40 are replaced with lysine; (c) a first human IgG3 constant region, wherein the amino acids at positions corresponding to positions 300 and 339 of SEQ ID NO:41 are replaced with glutamate or aspartate, and a second human IgG3 constant region wherein the amino acids at positions corresponding to positions 287 and 329 of SEQ ID NO:41 are replaced with lysine; and (d) a first human IgG4 constant region, wherein the amino acids at positions corresponding to positions 250 and 289 of SEQ ID NO:42 are replaced with glutamate or aspartate, and a second IgG4 constant region wherein the amino acids at positions corresponding to positions 237 and 279 of SEQ ID NO:42 are replaced with lysine.

In some embodiments, the heterodimeric protein comprises two polypeptides, wherein each polypeptide comprises a human IgG2 CH3 domain, and wherein the amino acids at positions corresponding to positions 249 and 288 of SEQ ID NO:40 of one IgG2 CH3 domain are replaced with glutamate or aspartate, and wherein the amino acids at positions corresponding to positions 236 and 278 of SEQ ID NO:40 of the other IgG2 CH3 domain are replaced with lysine.

In some embodiments, the binding agent (e.g., a soluble receptor) is a heterodimeric molecule which comprises a first human IgG1 constant region with amino acid substitutions at positions corresponding to positions 253 and 292 of SEQ ID NO:39, wherein the amino acids are replaced with glutamate or aspartate, and a second human IgG1 constant region with amino acid substitutions at positions corresponding to positions 240 and 282 of SEQ ID NO:39, wherein the amino acids are replaced with lysine. In some embodiments, the binding agent (e.g., a soluble receptor) is a fusion protein which comprises a first human IgG2 constant region with amino acid substitutions at positions corresponding to positions 249 and 288 of SEQ ID NO:40, wherein the amino acids are replaced with glutamate or aspartate, and a second human IgG2 constant region with amino acid substitutions at positions corresponding to positions 236 and 278 of SEQ ID NO:40, wherein the amino acids are replaced with lysine. In some embodiments, the binding agent (e.g., a soluble receptor) is a fusion protein which comprises a first human IgG3 constant region with amino acid substitutions at positions corresponding to positions 300 and 339 of SEQ ID NO:41, wherein the amino acids are replaced with glutamate or aspartate, and a second human IgG3 constant region with amino acid substitutions at positions corresponding to positions 287 and 329 of SEQ ID NO:41, wherein the amino acids are replaced with lysine. In some embodiments, the binding agent (e.g., a soluble receptor) is a fusion protein which comprises a first human IgG4 constant region with amino acid substitutions at positions corresponding to positions 250 and 289 of SEQ ID NO:42, wherein the amino acids are replaced with glutamate or aspartate, and a second human IgG4 constant region with amino acid substitutions at positions corresponding to positions 237 and 279 of SEQ ID NO:42, wherein the amino acids are replaced with lysine.

In some embodiments, the binding agent (e.g., a soluble receptor) is a fusion protein which comprises a first human IgG2 constant region with amino acid substitutions at positions corresponding to positions 249 and 288 of SEQ ID NO:40, wherein the amino acids are replaced with glutamate, and a second human IgG2 constant region with amino acid substitutions at positions corresponding to positions 236 and 278, wherein the amino acids are replaced with lysine. In some embodiments, the binding agent (e.g., a soluble receptor) is a fusion protein which comprises a first human IgG2 constant region with amino acid substitutions at positions corresponding to positions 249 and 288, wherein the amino acids are replaced with aspartate, and a second human IgG2 constant region with amino acid substitutions at positions corresponding to positions 236 and 278, wherein the amino acids are replaced with lysine.

In some embodiments, the binding agents described herein are monovalent. In some embodiments, the binding agent is a heterodimeric protein that is monovalent. In some embodiments, the binding agent comprises a soluble receptor that is monovalent. In some embodiments, the binding agents described herein are bivalent. In some embodiments, the binding agents described herein are monospecific. In some embodiments, the binding agents described herein are bispecific. In some embodiments, the binding agents described herein are multispecific.

The some embodiments, the binding agents are substantially homologous to the soluble receptors and/or polypeptides described herein. These binding agents can contain, for example, conservative substitution mutations, i.e. the substitution of one or more amino acids by similar amino acids. For example, conservative substitution refers to the substitution of an amino acid with another within the same general class such as, for example, one acidic amino acid with another acidic amino acid, one basic amino acid with another basic amino acid, or one neutral amino acid by another neutral amino acid. What is intended by a conservative amino acid substitution is well known in the art and described herein.

In some embodiments, the binding agents are bispecific antibodies. Bispecific antibodies are capable of specifically recognizing and binding at least two different epitopes. The different epitopes can either be within the same molecule (e.g., two epitopes on human TIGIT) or on different molecules (e.g., one epitope on TIGIT and one epitope on CD96). In some embodiments, the bispecific antibodies are monoclonal human or humanized antibodies. In some embodiments, the antibodies can specifically recognize and bind a first antigen target, (e.g., TIGIT) as well as a second antigen target, such as an effector molecule on a leukocyte (e.g., CD2, CD3, CD28, or CD80) or a Fc receptor (e.g., CD64, CD32, or CD16) so as to focus cellular defense mechanisms to the cell expressing the first antigen target. In some embodiments, the antibodies can be used to direct cytotoxic agents to cells which express a particular target antigen. These antibodies possess an antigen-binding arm and an arm which binds a cytotoxic agent or a radionuclide chelator, such as EOTUBE, DPTA, DOTA, or TETA.

Techniques for making bispecific antibodies are known by those skilled in the art, see for example, Millstein et al., 1983, Nature, 305:537-539; Brennan et al., 1985, Science, 229:81; Suresh et al., 1986, Methods in Enzymol., 121:120; Traunecker et al., 1991, EMBO J., 10:3655-3659; Shalaby et al., 1992, J. Exp. Med., 175:217-225; Kostelny et al., 1992, J. Immunol., 148:1547-1553; Gruber et al., 1994, J. Immunol., 152:5368; U.S. Pat. No. 5,731,168; and U.S. Patent Publication No. 2011/0123532). Bispecific antibodies can be intact antibodies or antibody fragments. Antibodies with more than two valencies are also contemplated. For example, trispecific antibodies can be prepared (Tutt et al., 1991, J. Immunol., 147:60).

In some embodiments, the binding agent is a bispecific antibody that specifically binds the extracellular domain of human TIGIT. In some embodiments, the bispecific antibody specifically binds the extracellular domain of TIGIT and the extracellular domain of CD96. In some embodiments, the binding agent is a bispecific antibody comprising a first antigen-binding site that specifically binds human TIGIT and a second antigen-binding site that specifically binds human CD96. In some embodiments, the binding agent is a bispecific antibody comprising a first antigen-binding site that specifically binds human TIGIT and a second antigen-binding site that specifically binds human CD96, wherein the light chains of the first and second antigen-binding sites are identical.

In some embodiments, the binding agent is a bispecific antibody that specifically binds the extracellular domain of human TIGIT and blocks signaling of TIGIT. In some embodiments, the binding agent is a bispecific antibody that specifically binds the extracellular domain of human TIGIT and binds the extracellular domain of human CD96 and blocks signaling of TIGIT and block signaling of CD96.

The binding agents (e.g., soluble receptors or polypeptides) of the present invention can be assayed for specific binding by any method known in the art. The immunoassays which can be used include, but are not limited to, competitive and non-competitive assay systems using techniques such as Biacore analysis, FACS analysis, immunofluorescence, immunocytochemistry, Western blots, radioimmunoassays, ELISA, "sandwich" immunoassays, immunoprecipitation assays, precipitation reactions, gel diffusion precipitin reactions, immunodiffusion assays, agglutination assays, complement-fixation assays, immunoradiometric assays, fluorescent immunoassays, and protein A immunoassays. Such assays are routine and well-known in the art (see, e.g., Ausubel et al., Editors, 1994-present, *Current Protocols in Molecular Biology*, John Wiley & Sons, Inc., New York, N.Y.).

For example, the specific binding of a binding agent (e.g., a soluble receptor) to a target such as TIGIT may be determined using ELISA. An ELISA assay comprises preparing antigen, coating wells of a 96 well microtiter plate with antigen, adding the binding agent conjugated to a detectable compound such as an enzymatic substrate (e.g. horseradish peroxidase or alkaline phosphatase) to the well, incubating for a period of time and detecting the presence of the binding agent bound to the antigen. In some embodiments, the binding agent is not conjugated to a detectable compound, but instead an antibody conjugated to a detectable compound that recognizes the binding agent (e.g., PE-conjugated anti-Fc antibody) is added to the well. In some embodiments, instead of coating the well with the antigen, the binding agent can be coated to the well and an antibody conjugated to a detectable compound can be added following the addition of the antigen to the coated well. One of skill in the art would be knowledgeable as to the parameters that can be modified to increase the signal detected as well as other variations of ELISAs known in the art.

In another example, the specific binding of a binding agent (e.g., a soluble receptor) to a target may be determined using FACS. A FACS screening assay may comprise generating a cDNA construct that expresses an antigen as a fusion protein (e.g., TIGIT-CD4TM), transfecting the construct into cells, expressing the antigen on the surface of the cells, mixing the binding agent with the transfected cells, and incubating for a period of time. The cells bound by the binding agent may be identified by using a secondary antibody conjugated to a detectable compound that recognizes the binding agent (e.g., PE-conjugated anti-Fc antibody) and a flow cytometer. A FACS screening assay may be used to identify a binding agent that binds more than one receptor, for example, TIGIT and CD96. A FACS screening assay may be used to show that a binding agent does not bind a receptor or binds weakly to a receptor. One of skill in the art would be knowledgeable as to the parameters that can be modified to optimize the signal detected as well as other variations of FACS that may enhance screening (e.g., screening for blocking agents).

The binding affinity of a binding agent (e.g., a soluble receptor) to a target (e.g., TIGIT) and the off-rate of a binding agent/target interaction can be determined by competitive binding assays. One example of a competitive binding assay is a radioimmunoassay comprising the incubation of labeled target (e.g., $^3$H or $^{125}$I), or fragment or variant thereof, with the binding agent of interest in the presence of increasing amounts of unlabeled target followed by the detection of the binding agent bound to the labeled target. The affinity of the binding agent for a target (e.g., TIGIT) and the binding off-rates can be determined from the data by Scatchard plot analysis. In some embodiments, Biacore kinetic analysis is used to determine the binding on and off rates of binding agents that bind a target (e.g., TIGIT). Biacore kinetic analysis comprises analyzing the binding and dissociation of binding agents from chips with immobilized target (e.g., TIGIT) on the chip surface.

In some embodiments, the binding agent (e.g., a soluble receptor) binds TIGIT with a dissociation constant ($K_D$) of about 1 µM or less, about 100 nM or less, about 40 nM or less, about 20 nM or less, about 10 nM or less, about 1 nM or less, or about 0.1 nM or less. In some embodiments, the binding agent binds TIGIT with a $K_D$ of about 1 nM or less. In some embodiments, the binding agent binds TIGIT with a $K_D$ of about 0.1 nM or less. In some embodiments, the binding agent binds human TIGIT with a $K_D$ of about 0.1 nM or less. In some embodiments, the binding agent (e.g., a soluble receptor) also binds CD96 with a $K_D$ of about 1 µM or less, about 100 nM or less, about 40 nM or less, about 20 nM or less, about 10 nM or less, about 1 nM or less, or about 0.1 nM or less. In some embodiments, the binding agent also binds CD96 with a $K_D$ of about 1 nM or less. In some embodiments, the binding agent also binds CD96 with a $K_D$ of about 0.1 nM or less. In some embodiments, the binding agent also binds CD96 with a $K_D$ of about 0.1 nM or less. In some embodiments, the binding agent binds both human TIGIT and mouse TIGIT with a $K_D$ of about 10 nM or less. In some embodiments, the binding agent binds both human TIGIT and mouse TIGIT with a $K_D$ of about 1 nM or less. In some embodiments, the binding agent binds both human TIGIT and mouse TIGIT with a $K_D$ of about 0.1 nM or less. In some embodiments, the binding agent does not bind human CD226. In some embodiments, the binding agent binds human CD226 with a high $K_D$ (weak binding).

In some embodiments, the dissociation constant of the binding agent to TIGIT is the dissociation constant determined using a TIGIT fusion protein comprising at least a portion of the TIGIT extracellular domain immobilized on a Biacore chip. In some embodiments, the dissociation constant of the binding agent to CD96 is the dissociation constant determined using a CD96 fusion protein comprising at least a portion of the CD96 extracellular domain immobilized on a Biacore chip. In some embodiments, the dissociation constant of the binding agent or lack of binding to CD226 is the dissociation constant determined using a CD226 fusion protein comprising at least a portion of the CD226 extracellular domain immobilized on a Biacore chip.

In some embodiments, the binding agent binds human TIGIT with a half maximal effective concentration ($EC_{50}$) of about 1 µM or less, about 100 nM or less, about 40 nM or less, about 20 nM or less, about 10 nM or less, about 1 nM or less, or about 0.1 nM or less. In certain embodiments, the binding agent also binds human CD96 with an $EC_{50}$ of about 40 nM or less, about 20 nM or less, about 10 nM or less, about 1 nM or less or about 0.1 nM or less.

In certain embodiments, the binding agents described herein bind TIGIT and/or CD96 and modulate an immune response. In some embodiments, a binding agent (e.g., a soluble receptor) activates and/or increases an immune response. In some embodiments, a binding agent increases, promotes, or enhances cell-mediated immunity. In some embodiments, a binding agent increases, promotes, or enhances innate cell-mediated immunity. In some embodiments, a binding agent increases, promotes, or enhances adaptive cell-mediated immunity. In some embodiments, a binding agent increases, promotes, or enhances T-cell activity. In some embodiments, a binding agent increases, promotes, or enhances cytolytic T-cell (CTL) activity. In some embodiments, a binding agent increases, promotes, or enhances NK cell activity. In some embodiments, a binding agent increases, promotes, or enhances lymphokine-activated killer cell (LAK) activity. In some embodiments, a binding agent increases, promotes, or enhances tumor cell killing. In some embodiments, a binding agent increases, promotes, or enhances the inhibition of tumor growth.

In some embodiments, the binding agents described herein bind TIGIT and inhibit TIGIT signaling. In some embodiments, a binding agent (e.g., a soluble receptor) binds TIGIT and blocks TIGIT signaling. In some embodiments, a binding agent is an antagonist of TIGIT-mediated signaling. In some embodiments, the binding agents described herein bind CD96 and inhibit CD96 signaling. In some embodiments, a binding agent (e.g., a soluble receptor) binds CD96 and blocks CD96 signaling. In some embodiments, a binding agent is an antagonist of CD96-mediated signaling. In some embodiments, the binding agents described herein bind TIGIT and CD96 and inhibit TIGIT signaling and CD96 signaling. In some embodiments, a binding agent (e.g., a soluble receptor) binds TIGIT and CD96 and blocks TIGIT signaling and blocks CD96 signaling. In some embodiments, a binding agent is an antagonist of TIGIT-mediated signaling and an antagonist of CD96-mediated signaling. In some embodiments, the binding agents described herein bind TIGIT and inhibit TIGIT signaling, but do not bind (or bind weakly to) CD226 and do not inhibit CD226 signaling. In some embodiments, the binding agents described herein bind TIGIT and CD96 and inhibit TIGIT and CD96 signaling, but do not bind (or bind weakly to) CD226 and do not inhibit CD226 signaling. In some embodiments, the binding agents described herein bind TIGIT, inhibit TIGIT signaling, and increase CD226 signaling. In some embodiments, the binding agents described herein bind TIGIT and CD96, inhibit TIGIT and CD96 signaling, and increase CD226 signaling. In some embodiments, the binding agents described herein increase CD226 signaling.

In some embodiments, a binding agent comprises a soluble receptor comprising a PVR variant described herein, wherein the PVR variant binds TIGIT and blocks TIGIT activity. In some embodiments, a binding agent comprises a soluble receptor comprising a PVR variant described herein, wherein the PVR variant binds TIGIT and blocks TIGIT activity and also binds CD96 and blocks CD96 activity. In some embodiments, a binding agent comprises a soluble receptor comprising a PVR variant described herein, wherein the PVR variant binds TIGIT and increases CD226 activity.

In certain embodiments, a binding agent described herein is an agonist (either directly or indirectly) of human CD226. In some embodiments, the binding agent is an agonist of CD226 and activates and/or increases an immune response. In some embodiments, the binding agent is an agonist of CD226 and activates and/or increases activity of NK cells and/or T-cells (e.g., cytolytic activity or cytokine production). In certain embodiments, the binding agent increases the activity by at least about 10%, at least about 20%, at least about 30%, at least about 50%, at least about 75%, at least about 90%, or about 100%.

In certain embodiments, a binding agent described herein is an antagonist (either directly or indirectly) of TIGIT and/or CD96. In some embodiments, the binding agent is an antagonist of TIGIT and/or CD96 and activates and/or increases an immune response. In some embodiments, the binding agent is an antagonist of TIGIT and/or CD96 and activates and/or increases activity of NK cells and/or T-cells (e.g., cytolytic activity or cytokine production). In certain embodiments, the binding agent the binding agent increases the activity by at least about 10%, at least about 20%, at least about 30%, at least about 50%, at least about 75%, at least about 90%, or about 100%.

In certain embodiments, a binding agent described herein increases activation of a NK cell. In certain embodiments, a binding agent (e.g., soluble receptor) increases activation of a T-cell. In certain embodiments, the activation of a NK cell and/or a T-cell by an binding agent results in an increase in the level of activation of a NK cell and/or a T-cell of at least about 10%, at least about 25%, at least about 50%, at least about 75%, at least about 90%, or at least about 95%.

In vivo and in vitro assays for determining whether a binding agent (or candidate binding agent) modulates an immune response are known in the art or are being developed. In some embodiments, a functional assay that detects T-cell activation may be used. For example, a population of T-cells can be stimulated with irradiated allogeneic cells expressing PVR, in the presence or absence of a binding agent described herein. An agent that blocks TIGIT and/or CD96 signaling will cause an increase in the T-cell activation, as measured by proliferation and cell cycle progression, IL-2 production, and/or up-regulation of CD25 and CD69. In some embodiments, a functional assay that detects NK cell activity may be used. For example, a population of target cells expressing PVR can be co-cultured with NK cells, in the presence or absence of a binding agent described herein. An agent that blocks TIGIT and/or CD96 signaling will cause an increase in the percentage of target cells killed by the NK cells.

In certain embodiments, the binding agents are capable of inhibiting tumor growth. In certain embodiments, the binding agents are capable of inhibiting tumor growth in vivo (e.g., in a xenograft mouse model, and/or in a human having cancer).

In certain embodiments, the binding agents are capable of reducing the tumorigenicity of a tumor. In certain embodiments, the binding agent is capable of reducing the tumorigenicity of a tumor in an animal model, such as a mouse xenograft model. In certain embodiments, the binding agent is capable of reducing the tumorigenicity of a tumor comprising cancer stem cells in an animal model, such as a mouse xenograft model. In certain embodiments, the number or frequency of cancer stem cells in a tumor is reduced by at least about two-fold, about three-fold, about five-fold, about ten-fold, about 50-fold, about 100-fold, or about 1000-fold. In certain embodiments, the reduction in the number or frequency of cancer stem cells is determined by limiting dilution assay using an animal model. Additional examples and guidance regarding the use of limiting dilution assays to determine a reduction in the number or frequency of cancer stem cells in a tumor can be found, e.g., in International Publication Number WO 2008/042236; U.S. Patent Publication No. 2008/0064049; and U.S. Patent Publication No. 2008/0178305.

In certain embodiments, the binding agents have one or more of the following effects: inhibit proliferation of tumor cells, inhibit tumor growth, reduce the tumorigenicity of a tumor, reduce the tumorigenicity of a tumor by reducing the frequency of cancer stem cells in the tumor, trigger cell death of tumor cells, increase cell contact-dependent growth inhibition, increase tumor cell apoptosis, reduce epithelial mesenchymal transition (EMT), or decrease survival of tumor cells. In some embodiments, the binding agents have one or more of the following effects: inhibit viral infection, inhibit chronic viral infection, reduce viral load, trigger cell death of virus-infected cells, or reduce the number or percentage of virus-infected cells.

In certain embodiments, the binding agents described herein have a circulating half-life in mice, cynomolgus monkeys, or humans of at least about 5 hours, at least about 10 hours, at least about 24 hours, at least about 3 days, at least about 1 week, or at least about 2 weeks. In certain embodiments, the binding agent is an IgG (e.g., IgG1 or IgG2) fusion protein that has a circulating half-life in mice, cynomolgus monkeys, or humans of at least about 5 hours, at least about 10 hours, at least about 24 hours, at least about 3 days, at least about 1 week, or at least about 2 weeks. Methods of increasing (or decreasing) the half-life of agents such as polypeptides and soluble receptors are known in the art. For example, known methods of increasing the circulating half-life of IgG fusion proteins include the introduction of mutations in the Fc region which increase the pH-dependent binding of the antibody to the neonatal Fc receptor (FcRn) at pH 6.0 (see, e.g., U.S. Patent Publication Nos. 2005/0276799, 2007/0148164, and 2007/0122403). Known methods of increasing the circulating half-life of soluble receptors lacking a Fc region include such techniques as PEGylation.

In some embodiments of the present invention, the binding agents are polypeptides. The polypeptides can be recombinant polypeptides, natural polypeptides, or synthetic polypeptides that bind TIGIT and/or CD96. It will be recognized in the art that some amino acid sequences of the invention can be varied without significant effect of the structure or function of the protein. Thus, the invention further includes variations of the polypeptides which show substantial binding activity to TIGIT and/or CD96. In some embodiments, amino acid sequence variations of the polypeptides include deletions, insertions, inversions, repeats, and/or other types of substitutions.

The polypeptides, analogs and variants thereof, can be further modified to contain additional chemical moieties not normally part of the polypeptide. The derivatized moieties can improve the solubility, the biological half-life, and/or absorption of the polypeptide. The moieties can also reduce or eliminate undesirable side effects of the polypeptides and variants. An overview for chemical moieties can be found in *Remington: The Science and Practice of Pharmacy*, $22^{st}$ *Edition*, 2012, Pharmaceutical Press, London.

The polypeptides described herein can be produced by any suitable method known in the art. Such methods range from direct protein synthesis methods to constructing a DNA sequence encoding polypeptide sequences and expressing those sequences in a suitable host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. See, e.g., Zoeller et al., 1984, *PNAS*, 81:5662-5066 and U.S. Pat. No. 4,588,585.

In some embodiments, a DNA sequence encoding a polypeptide of interest may be constructed by chemical synthesis using an oligonucleotide synthesizer. Oligonucleotides can be designed based on the amino acid sequence of the desired polypeptide and selecting those codons that are favored in the host cell in which the recombinant polypeptide of interest will be produced. Standard methods can be applied to synthesize a polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis, or another method), the polynucleotide sequences encoding a particular polypeptide of interest can be inserted into an expression vector and operatively linked to an expression control sequence appropriate for expression of the protein in a desired host. Proper assembly can be confirmed by nucleotide sequencing, restriction enzyme mapping, and/or expression of a biologically active polypeptide in a suitable host. As is well-known in the art, in order to obtain high expression levels of a transfected gene in a host, the gene must be operatively linked to transcriptional and translational expression control sequences that are functional in the chosen expression host.

In certain embodiments, recombinant expression vectors are used to amplify and express DNA encoding the binding agents (e.g., soluble receptors) described herein. For example, recombinant expression vectors can be replicable DNA constructs which have synthetic or cDNA-derived DNA fragments encoding a polypeptide chain of a binding agent operatively linked to suitable transcriptional and/or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences. Regulatory elements can include an operator sequence to control transcription. The ability to replicate in a host, usually conferred by an origin of replication, and a selection gene to facilitate recognition of transformants can additionally be incorporated. DNA regions are "operatively linked" when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. In some embodiments, structural elements intended for use in yeast expression systems include a leader sequence enabling extracellular secretion of translated protein by a host cell. In other embodiments, where recombinant protein is expressed without a leader or transport sequence, it can include an N-terminal methionine residue. This residue can optionally be subsequently cleaved from the expressed recombinant protein to provide a final product.

The choice of an expression control sequence and an expression vector depends upon the choice of host. A wide variety of expression host/vector combinations can be employed. Useful expression vectors for eukaryotic hosts include, for example, vectors comprising expression control sequences from SV40, bovine papilloma virus, adenovirus, and cytomegalovirus. Useful expression vectors for bacterial hosts include known bacterial plasmids, such as plasmids from *E. coli*, including pCR1, pBR322, pMB9 and their derivatives, and wider host range plasmids, such as M13 and other filamentous single-stranded DNA phages.

Suitable host cells for expression of a polypeptide (or a protein to use as a target) include prokaryotes, yeast cells, insect cells, or higher eukaryotic cells under the control of appropriate promoters. Prokaryotes include gram-negative or gram-positive organisms, for example *E. coli* or *Bacillus*. Higher eukaryotic cells include established cell lines of mammalian origin as described below. Cell-free translation systems may also be employed. Appropriate cloning and expression vectors for use with bacterial, fungal, yeast, and mammalian cellular hosts are described by Pouwels et al. (1985, *Cloning Vectors: A Laboratory Manual*, Elsevier, New York, N.Y.). Additional information regarding methods of protein production, including antibody production, can be found, e.g., in U.S. Patent Publication No. 2008/0187954; U.S. Pat. Nos. 6,413,746 and 6,660,501; and International Patent Publication No. WO 2004/009823.

Various mammalian cell culture systems are used to express recombinant polypeptides. Expression of recombinant proteins in mammalian cells can be preferred because such proteins are generally correctly folded, appropriately modified, and biologically functional. Examples of suitable mammalian host cell lines include COS-7 (monkey kidney-derived), L-929 (murine fibroblast-derived), C127 (murine mammary tumor-derived), 3T3 (murine fibroblast-derived), CHO (Chinese hamster ovary-derived), HeLa (human cervical cancer-derived), BHK (hamster kidney fibroblast-derived), and HEK-293 (human embryonic kidney-derived) cell lines and variants thereof. Mammalian expression vectors can comprise non-transcribed elements such as an origin of replication, a suitable promoter and enhancer linked to the gene to be expressed, and other 5' or 3' flanking non-transcribed sequences, and 5' or 3' non-translated sequences, such as necessary ribosome binding sites, a polyadenylation site, splice donor and acceptor sites, and transcriptional termination sequences.

Expression of recombinant proteins in insect cell culture systems (e.g., baculovirus) also offers a robust method for producing correctly folded and biologically functional proteins. Baculovirus systems for production of heterologous proteins in insect cells are well-known to those of skill in the art (see, e.g., Luckow and Summers, 1988, *Bio/Technology*, 6:47).

Thus, the present invention provides cells comprising the binding agents described herein. In some embodiments, the cells produce the binding agents described herein. In certain embodiments, the cells produce a fusion protein. In some embodiments, the cells produce a soluble receptor. In some embodiments, the cells produce an antibody. In some embodiments, the cells produce a bispecific antibody. In some embodiments, the cells produce a heterodimeric protein.

The proteins produced by a transformed host can be purified according to any suitable method. Standard methods include chromatography (e.g., ion exchange, affinity, and sizing column chromatography), centrifugation, differential solubility, or by any other standard technique for protein purification Affinity tags such as hexa-histidine, maltose binding domain, influenza coat sequence, and glutathione-S-transferase can be attached to the protein to allow easy purification by passage over an appropriate affinity column. Isolated proteins can also be physically characterized using such techniques as proteolysis, mass spectrometry (MS), nuclear magnetic resonance (NMR), high performance liquid chromatography (HPLC), and x-ray crystallography.

In some embodiments, supernatants from expression systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. In some embodiments, an anion exchange resin can be employed, for example, a matrix or substrate having pendant diethylaminoethyl (DEAE) groups. The matrices can be acrylamide, agarose, dextran, cellulose, or other types commonly employed in protein purification. In some embodiments, a cation exchange step can be employed. Suitable cation exchangers include various insoluble matrices comprising sulfopropyl or carboxymethyl groups. In some embodiments, a hydroxyapatite media can be employed, including but not limited to, ceramic hydroxyapatite (CHT). In certain embodiments, one or more reverse-phase HPLC steps employing hydrophobic RP-HPLC media, e.g., silica gel having pendant methyl or other aliphatic groups, can be employed to further purify a binding agent. Some or all of the foregoing purification steps, in various combinations, can also be employed to provide a homogeneous recombinant protein.

In some embodiments, recombinant protein produced in bacterial culture can be isolated, for example, by initial extraction from cell pellets, followed by one or more concentration, salting-out, aqueous ion exchange, or size exclusion chromatography steps. HPLC can be employed for final purification steps. Microbial cells employed in expression of a recombinant protein can be disrupted by any convenient method, including freeze-thaw cycling, sonication, mechanical disruption, or use of cell lysing agents.

Methods known in the art for purifying polypeptides also include, for example, those described in U.S. Patent Publication Nos. 2008/0312425, 2008/0177048, and 2009/0187005.

In certain embodiments, a binding agent described herein is a polypeptide that does not comprise an immunoglobulin Fc region. In certain embodiments, the polypeptide comprises a protein scaffold of a type selected from the group consisting of protein A, protein G, a lipocalin, a fibronectin domain, an ankyrin consensus repeat domain, and thioredoxin. A variety of methods for identifying and producing non-antibody polypeptides that bind with high affinity to a protein target are known in the art. See, e.g., Skerra, 2007, *Curr. Opin. Biotechnol.*, 18:295-304; Hosse et al., 2006, *Protein Science*, 15:14-27; Gill et al., 2006, *Curr. Opin. Biotechnol.*, 17:653-658; Nygren, 2008, *FEBS J.*, 275:2668-76; and Skerra, 2008, *FEBS J.*, 275:2677-83. In certain embodiments, phage display technology may be used to produce and/or identify a binding polypeptide. In certain embodiments, mammalian cell display technology may be used to produce and/or identify a binding polypeptide.

It can further be desirable to modify a polypeptide in order to increase (or decrease) its serum half-life. This can be achieved, for example, by incorporation of a salvage receptor binding epitope into the polypeptide by mutation of the appropriate region in the polypeptide or by incorporating the epitope into a peptide tag that is then fused to the polypeptide at either end or in the middle (e.g., by DNA or peptide synthesis).

Heteroconjugate molecules are also within the scope of the present invention. Heteroconjugate molecules are composed of two covalently joined polypeptides. Such molecules have, for example, been proposed to target immune cells to unwanted cells, such as tumor cells. It is also contemplated that the heteroconjugate molecules can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate.

In certain embodiments, a binding agent described herein can be used in any one of a number of conjugated (i.e. an immunoconjugate or radioconjugate) or non-conjugated forms. In certain embodiments, the binding agents can be used in a non-conjugated form to harness the subject's natural defense mechanisms including CDC and ADCC to eliminate malignant or cancer cells.

In certain embodiments, a binding agent described herein is a small molecule. The term "small molecule" generally refers to a low molecular weight organic compound which is by definition not a peptide/protein. A small molecule binding agent described herein may bind to TIGIT and/or CD96 with high affinity and interfere with or block the interaction of TIGIT and/or CD96 with PVR. In some embodiments, the small molecule interferes with or blocks the interaction of TIGIT and/or CD96 with PVR, disrupting TIGIT signaling, but does not disrupt CD226 signaling.

In some embodiments, a binding agent described herein is conjugated to a cytotoxic agent. In some embodiments, the cytotoxic agent is a chemotherapeutic agent including, but not limited to, methotrexate, adriamicin, doxorubicin, melphalan, mitomycin C, chlorambucil, daunorubicin or other intercalating agents. In some embodiments, the cytotoxic agent is an enzymatically active toxin of bacterial, fungal, plant, or animal origin, or fragments thereof, including, but not limited to, diphtheria A chain, nonbinding active fragments of diphtheria toxin, exotoxin A chain, ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. In some embodiments, the cytotoxic agent is a radioisotope to produce a radioconjugate or a radioconjugated binding agent. A variety of radionuclides are available for the production of radioconjugated binding agents including, but not limited to, $^{90}$Y, $^{125}$I, $^{131}$I, $^{123}$I, $^{111}$In, $^{131}$In, $^{105}$Rh, $^{153}$Sm, $^{67}$Cu, $^{67}$Ga, $^{166}$Ho, $^{177}$Lu, $^{186}$Re, $^{188}$Re, and $^{212}$Bi. Conjugates of a binding agent and one or more small molecule toxins, such as a calicheamicin, maytansinoids, a trichothene, and CC1065, and the derivatives of these toxins that have toxin activity, can also be used. In some embodiments, a binding agent described herein is conjugated to a maytansinoid. In some embodiments, a binding agent described herein is conjugated to mertansine (DM1). Conjugates of a binding agent and cytotoxic agent are made using a variety of bifunctional protein-coupling agents such as N-succinimidyl-3-(2-pyridyidithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene).

III. Polynucleotides

In certain embodiments, the invention encompasses polynucleotides comprising polynucleotides that encode a binding agent (e.g., a soluble receptor or polypeptide) described herein. The term "polynucleotides that encode a polypeptide" encompasses a polynucleotide which includes only coding sequences for the polypeptide as well as a polynucleotide which includes additional coding and/or non-coding sequences. The polynucleotides of the invention can be in the form of RNA or in the form of DNA. DNA includes cDNA, genomic DNA, and synthetic DNA; and can be double-stranded or single-stranded, and if single stranded can be the coding strand or non-coding (anti-sense) strand.

In certain embodiments, the polynucleotide comprises a polynucleotide encoding a polypeptide comprising an amino acid sequence selected from the group consisting of: SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, and SEQ ID NO:38. In certain embodiments, the polynucleotide comprises a polynucleotide encoding a polypeptide comprising an amino acid sequence selected from the group consisting of: SEQ ID NO:18, SEQ ID NO:19, SEQ ID NO:20, SEQ ID NO:21, and SEQ ID NO:38.

In certain embodiments, a polynucleotide comprises a polynucleotide having a nucleotide sequence at least 80% identical, at least 85% identical, at least 90% identical, at least 95% identical, and in some embodiments, at least 96%, 97%, 98% or 99% identical to a polynucleotide encoding an amino acid sequence selected from the group consisting of:

SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, and SEQ ID NO:38. In certain embodiments, a polynucleotide comprises a polynucleotide having a nucleotide sequence at least 80% identical, at least 85% identical, at least 90% identical, at least 95% identical, and in some embodiments, at least 96%, 97%, 98% or 99% identical to a polynucleotide encoding an amino acid sequence selected from the group consisting of: SEQ ID NO:18, SEQ ID NO:19, SEQ ID NO:20, SEQ ID NO:21, and SEQ ID NO:38. Also provided is a polynucleotide that comprises a polynucleotide that hybridizes to a polynucleotide encoding an amino acid sequence selected from the group consisting of: SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, and SEQ ID NO:38. Also provided is a polynucleotide that comprises a polynucleotide that hybridizes to a polynucleotide encoding an amino acid sequence selected from the group consisting of: SEQ ID NO:18, SEQ ID NO:19, SEQ ID NO:20, SEQ ID NO:21, and SEQ ID NO:38. Also provided is a polynucleotide that comprises a polynucleotide that hybridizes to the complement of a polynucleotide encoding an amino acid sequence selected from the group consisting of: SEQ ID NO:18, SEQ ID NO:19, SEQ ID NO:20, SEQ ID NO:21, and SEQ ID NO:38. In certain embodiments, the hybridization is under conditions of high stringency. Conditions of high stringency are known to those of skill in the art and may include but are not limited to, (1) employ low ionic strength and high temperature for washing, for example 15 mM sodium chloride/1.5 mM sodium citrate (1×SSC) with 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 in 5×SSC (0.75M NaCl, 75 mM sodium citrate) at 42° C.; or (3) employ 50% formamide, 5×SSC, 50 mM sodium phosphate (pH 6.8), 0.1% sodium pyrophosphate, 5×Denhardt's solution, sonicated salmon sperm DNA (50 μm/ml), 0.1% SDS, and 10% dextran sulfate at 42° C., with washes in 0.2×SSC containing 50% formamide at 55° C., followed by a high-stringency wash consisting of 0.1×SSC containing EDTA at 55° C.

In certain embodiments, a polynucleotide comprises the coding sequence for the mature polypeptide fused in the same reading frame to a polynucleotide which aids, for example, in expression and secretion of a polypeptide from a host cell (e.g., a leader sequence which functions as a secretory sequence for controlling transport of a polypeptide from the cell). The polypeptide having a leader sequence is a preprotein and can have the leader sequence cleaved by the host cell to form the mature form of the polypeptide. The polynucleotides can also encode for a proprotein which is the mature protein plus additional 5' amino acid residues. A mature protein having a prosequence is a proprotein and is an inactive form of the protein. Once the prosequence is cleaved an active mature protein remains.

In certain embodiments, a polynucleotide comprises the coding sequence for the mature polypeptide fused in the same reading frame to a marker sequence that allows, for example, for purification of the encoded polypeptide. For example, the marker sequence can be a hexa-histidine tag supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g., COS-7 cells) is used. In some embodiments, the marker sequence is a FLAG-tag, a peptide of sequence DYKDDDDK (SEQ ID NO:32) which can be used in conjunction with other affinity tags.

The present invention further relates to variants of the hereinabove described polynucleotides encoding, for example, fragments, analogs, and/or derivatives.

In certain embodiments, the present invention provides a polynucleotide comprising a polynucleotide having a nucleotide sequence at least about 80% identical, at least about 85% identical, at least about 90% identical, at least about 95% identical, and in some embodiments, at least about 96%, 97%, 98% or 99% identical to a polynucleotide encoding a polypeptide comprising a binding agent (e.g., a soluble receptor or a polypeptide) described herein.

As used herein, the phrase a polynucleotide having a nucleotide sequence at least, for example, 95% "identical" to a reference nucleotide sequence is intended to mean that the nucleotide sequence of the polynucleotide is identical to the reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the 5' or 3' terminal positions of the reference nucleotide sequence or anywhere between those terminal positions, interspersed either individually among nucleotides in the reference sequence or in one or more contiguous groups within the reference sequence.

The polynucleotide variants can contain alterations in the coding regions, non-coding regions, or both. In some embodiments, a polynucleotide variant contains alterations which produce silent substitutions, additions, or deletions, but does not alter the properties or activities of the encoded polypeptide. In some embodiments, a polynucleotide variant comprises silent substitutions that results in no change to the amino acid sequence of the polypeptide (due to the degeneracy of the genetic code). Polynucleotide variants can be produced for a variety of reasons, for example, to optimize codon expression for a particular host (i.e., change codons in the human mRNA to those preferred by a bacterial host such as E. coli). In some embodiments, a polynucleotide variant comprises at least one silent mutation in a non-coding or a coding region of the sequence.

In some embodiments, a polynucleotide variant is produced to modulate or alter expression (or expression levels) of the encoded polypeptide. In some embodiments, a polynucleotide variant is produced to increase expression of the encoded polypeptide. In some embodiments, a polynucleotide variant is produced to decrease expression of the encoded polypeptide. In some embodiments, a polynucleotide variant has increased expression of the encoded polypeptide as compared to a parental polynucleotide sequence.

In some embodiments, a polynucleotide variant has decreased expression of the encoded polypeptide as compared to a parental polynucleotide sequence.

In some embodiments, at least one polynucleotide variant is produced (without changing the amino acid sequence of the encoded polypeptide) to increase production of a heterodimeric molecule. In some embodiments, at least one polynucleotide variant is produced (without changing the amino acid sequence of the encoded polypeptide) to increase production of a bispecific antibody.

In certain embodiments, the polynucleotides are isolated. In certain embodiments, the polynucleotides are substantially pure.

Vectors and cells comprising the polynucleotides described herein are also provided. In some embodiments, an expression vector comprises a polynucleotide molecule. In some embodiments, a host cell comprises an expression vector comprising the polynucleotide molecule. In some embodiments, a host cell comprises a polynucleotide molecule.

IV. Methods of Use and Pharmaceutical Compositions

The binding agents of the invention are useful in a variety of applications including, but not limited to, therapeutic treatment methods, such as immunotherapy for cancer. In certain embodiments, the binding agents are useful for activating, promoting, increasing, and/or enhancing an immune response, inhibiting tumor growth, reducing tumor volume, increasing tumor cell apoptosis, and/or reducing the tumorigenicity of a tumor. The binding agents of the invention are also useful for immunotherapy against pathogens, such as viruses. In certain embodiments, the binding agents are useful for activating, promoting, increasing, and/or enhancing an immune response, inhibiting viral infection, reducing viral infection, increasing virally-infected cell apoptosis, and/or increasing killing of virus-infected cells. The methods of use may be in vitro, ex vivo, or in vivo methods. In some embodiments, a binding agent is an agonist of an immune response. In some embodiments, a binding agent is an antagonist of TIGIT. In some embodiments, a binding agent is an antagonist of CD96. In some embodiments, a binding agent is an antagonist of TIGIT and CD96. In some embodiments, a binding agent is an agonist of CD226.

The present invention provides methods for activating an immune response in a subject using the binding agents described herein. In some embodiments, the invention provides methods for promoting an immune response in a subject using a binding agent described herein. In some embodiments, the invention provides methods for increasing an immune response in a subject using a binding agent described herein. In some embodiments, the invention provides methods for enhancing an immune response in a subject using a binding agent described herein. In some embodiments, the activating, promoting, increasing, and/or enhancing of an immune response comprises increasing cell-mediated immunity. In some embodiments, the activating, promoting, increasing, and/or enhancing of an immune response comprises increasing T-cell activity. In some embodiments, the activating, promoting, increasing, and/or enhancing of an immune response comprises increasing CTL activity. In some embodiments, the activating, promoting, increasing, and/or enhancing of an immune response comprises increasing NK cell activity. In some embodiments, the activating, promoting, increasing, and/or enhancing of an immune response comprises increasing T-cell activity and increasing NK cell activity. In some embodiments, the activating, promoting, increasing, and/or enhancing of an immune response comprises increasing CU activity and increasing NK cell activity. In some embodiments, the immune response is a result of antigenic stimulation. In some embodiments, the antigenic stimulation is a tumor cell. In some embodiments, the antigenic stimulation is cancer. In some embodiments, the antigenic stimulation is a pathogen. In some embodiments, the antigenic stimulation is a virally-infected cell.

In some embodiments, a method of increasing an immune response in a subject comprises administering to the subject a therapeutically effective amount of a binding agent described herein, wherein the binding agent inhibits the interaction between TIGIT and PVR, inhibits the interaction between CD96 and PVR, and does not inhibit the interaction between CD226 and PVR.

In some embodiments, the invention provides methods of increasing the activity of CD226-positive cells. In some embodiments, the method comprises contacting the CD226-positive cells with an effective amount of a binding agent described herein. In some embodiments, the CD226-positive cells are T-cells, NK cells, monocytes, macrophages, and/or B-cells. In some embodiments, the increasing of activity of CD226-positive cells is evidenced by increased cytolytic activity. In some embodiments, the increasing of activity of CD226-positive cells is evidenced by increased killing of target cells. In some embodiments, the increasing of activity of CD226-positive cells is evidenced by increased killing of tumor cells. In some embodiments, the increasing of activity of CD226-positive cells is evidenced by inhibition of tumor growth. In some embodiments, the increasing of activity of CD226-positive cells is evidenced by inhibition of viral infection. In some embodiments, the increasing of activity of CD226-positive cells is evidenced by increased killing of virally-infected cells.

The present invention also provides methods for inhibiting growth of a tumor using the binding agents described herein. In certain embodiments, the method of inhibiting growth of a tumor comprises contacting a cell mixture with a binding agent in vitro. For example, an immortalized cell line or a cancer cell line mixed with immune cells (e.g., T-cells or NK cells) is cultured in medium to which is added a binding agent. In some embodiments, tumor cells are isolated from a patient sample such as, for example, a tissue biopsy, pleural effusion, or blood sample, mixed with immune cells (e.g., T-cells and/or NK cells), and cultured in medium to which is added a binding agent. In some embodiments, the binding agent increases, promotes, and/or enhances the activity of the immune cells. In some embodiments, the binding agent inhibits tumor cell growth. In some embodiments, the binding agent comprises a soluble receptor. In some embodiments, the binding agent is a soluble receptor. In some embodiments, the binding agent is an antibody. In some embodiments, the binding agent is a polypeptide.

In some embodiments, the method of inhibiting growth of a tumor comprises contacting the tumor or tumor cells with a binding agent in vivo. In certain embodiments, contacting a tumor or tumor cell with a binding agent is undertaken in an animal model. For example, a binding agent may be administered to mice which have syngeneic tumors. In some embodiments, the binding agent increases, promotes, and/or enhances the activity of immune cells in the mice. In some embodiments, the binding agent inhibits tumor growth. In some embodiments, the binding agent is administered at the same time or shortly after introduction of tumor cells into the animal to prevent tumor growth ("preventative model"). In some embodiments, the binding agent is administered as a therapeutic after tumors have grown to a specified size ("therapeutic model"). In some embodiments, the binding agent comprises a soluble receptor. In some embodiments, the binding agent is a soluble receptor. In some embodiments, the binding agent is an antibody. In some embodiments, the binding agent is a polypeptide.

In certain embodiments, the method of inhibiting growth of a tumor comprises administering to a subject a therapeutically effective amount of a binding agent described herein. In certain embodiments, the subject is a human. In certain embodiments, the subject has a tumor or has had a tumor which was removed. In some embodiments, the binding agent comprises a soluble receptor. In some embodiments, the binding agent is a soluble receptor. In some embodiments, the binding agent is an antibody. In some embodiments, the binding agent is a polypeptide.

In addition, the invention provides a method of inhibiting growth of a tumor in a subject, comprising administering a therapeutically effective amount of a binding agent to the subject. In certain embodiments, the tumor comprises cancer stem cells. In certain embodiments, the frequency of cancer stem cells in the tumor is reduced by administration of the binding agent. In some embodiments, a method of reducing the frequency of cancer stem cells in a tumor in a subject, comprising administering to the subject a therapeutically effective amount of a binding agent is provided. In some embodiments, the binding agent comprises a soluble receptor. In some embodiments, the binding agent is a soluble receptor. In some embodiments, the binding agent is an antibody. In some embodiments, the binding agent is a polypeptide.

In some embodiments, a method of inhibiting tumor growth in a subject comprises: administering to the subject a therapeutically effective amount of a binding agent described herein, wherein the binding agent inhibits the interaction between TIGIT and PVR, inhibits the interaction between CD96 and PVR, and does not inhibit the interaction between CD226 and PVR. In some embodiments, the PVR is expressed on the tumor cell. In some embodiments, TIGIT is expressed on NK cells and/or T-cells. In some embodiments, CD96 is expressed on NK cells and/or T-cells. In some embodiments, CD226 is expressed on NK cells and/or T-cells. In some embodiments, PVR is expressed on tumor cells and TIGIT and CD226 are expressed on NK cells and/or T-cells. In some embodiments, PVR is expressed on tumor cells and TIGIT, CD96, and CD226 are expressed on NK cells and/or T-cells.

In addition, the invention provides a method of reducing the tumorigenicity of a tumor in a subject, comprising administering to a subject a therapeutically effective amount of a binding agent described herein. In certain embodiments, the tumor comprises cancer stem cells. In some embodiments, the tumorigenicity of a tumor is reduced by reducing the frequency of cancer stem cells in the tumor. In some embodiments, the methods comprise using the binding agents described herein. In certain embodiments, the frequency of cancer stem cells in the tumor is reduced by administration of a binding agent.

In some embodiments, the tumor is a solid tumor. In certain embodiments, the tumor is a tumor selected from the group consisting of: colorectal tumor, pancreatic tumor, lung tumor, ovarian tumor, liver tumor, breast tumor, kidney tumor, prostate tumor, neuroendocrine tumor, gastrointestinal tumor, melanoma, cervical tumor, bladder tumor, glioblastoma, and head and neck tumor. In certain embodiments, the tumor is a colorectal tumor. In certain embodiments, the tumor is an ovarian tumor. In some embodiments, the tumor is a lung tumor. In certain embodiments, the tumor is a pancreatic tumor. In certain embodiments, the tumor is a melanoma tumor.

The present invention further provides methods for treating cancer in a subject comprising administering a therapeutically effective amount of the binding agent to a subject. In some embodiments, the binding agent binds the extracellular domain of TIGIT and/or CD96, increases an immune response, and inhibits or reduces growth of the cancer. In some embodiments, the binding agent binds TIGIT. In some embodiments, the binding agent binds TIGIT and CD96. In some embodiments, the binding agent binds TIGIT and does not bind (or binds weakly to) CD226. In some embodiments, the binding agent binds TIGIT and CD96 and does not bind (or binds weakly to) CD226. In some embodiments, the binding agent comprises a soluble receptor. In some embodiments, the binding agent is a soluble receptor. In some embodiments, the binding agent is an antibody. In some embodiments, the binding agent is a polypeptide.

The present invention provides for methods of treating cancer comprising administering a therapeutically effective amount of a binding agent described herein to a subject (e.g., a subject in need of treatment). In certain embodiments, the subject is a human. In certain embodiments, the subject has a cancerous tumor. In certain embodiments, the subject has had a tumor removed.

In certain embodiments, the cancer is a cancer selected from the group consisting of colorectal cancer, pancreatic cancer, lung cancer, ovarian cancer, liver cancer, breast cancer, kidney cancer, prostate cancer, gastrointestinal cancer, melanoma, cervical cancer, neuroendocrine cancer, bladder cancer, glioblastoma, and head and neck cancer. In certain embodiments, the cancer is pancreatic cancer. In certain embodiments, the cancer is ovarian cancer. In certain embodiments, the cancer is colorectal cancer. In certain embodiments, the cancer is breast cancer. In certain embodiments, the cancer is prostate cancer. In certain embodiments, the cancer is lung cancer. In certain embodiments, the cancer is melanoma.

In some embodiments, the cancer is a hematologic cancer. In some embodiment, the cancer is selected from the group consisting of: acute myelogenous leukemia (AML), Hodgkin lymphoma, multiple myeloma, T-cell acute lymphoblastic leukemia (T-ALL), chronic lymphocytic leukemia (CLL), hairy cell leukemia, chronic myelogenous leukemia (CML), non-Hodgkin lymphoma, diffuse large B-cell lymphoma (DLBCL), mantle cell lymphoma (MCL), and cutaneous T-cell lymphoma (CTCL).

The invention also provides a method of inactivating, inhibiting, or suppressing TIGIT and/or CD96 signaling in a cell comprising contacting the cell with an effective amount of a binding agent described herein. In certain embodiments, the cell is a T-cell. In some embodiments, the cell is a cytolytic cell. In some embodiments, the cell is a CTL. In some embodiments, the cell is a NK cell. In certain embodiments, the method is an in vivo method wherein the step of contacting the cell with the binding agent comprises administering a therapeutically effective amount of the binding agent to the subject. In some embodiments, the method is an in vitro or ex vivo method. In certain embodiments, the binding agent inhibits, suppresses, and/or decreases TIGIT and/or CD96 signaling. In some embodiments, the binding agent comprises a soluble receptor. In some embodiments, the binding agent is a soluble receptor. In some embodiments, the binding agent is a polypeptide. In some embodiments, the binding agent is an antibody.

The invention also provides a method of activating or enhancing CD226 signaling in a cell comprising contacting the cell with an effective amount of a binding agent described herein. In certain embodiments, the cell is a T-cell. In some embodiments, the cell is a cytolytic cell. In some embodiments, the cell is a CTL. In some embodiments, the cell is a NK cell. In certain embodiments, the method is an in vivo method wherein the step of contacting the cell with the binding agent comprises administering a therapeutically effective amount of the binding agent to the subject. In some embodiments, the method is an in vitro or ex vivo method. In certain embodiments, the binding agent activates, promotes, induces, enhances, and/or increases CD226 signaling. In some embodiments, the binding agent comprises a soluble receptor. In some embodiments, the binding agent is a soluble receptor. In some embodiments, the binding agent is a polypeptide. In some embodiments, the binding agent is an antibody.

Over-expression or aberrant exposure of some members of the immunoglobulin superfamily on cells (e.g., tumor cells or virally infected cells) may allow the receptors to serve as targets for surveillance by the immune system ("immunosurveillance"). For example, a central characteristic of epithelial cell biology is that epithelial cells exist in single-cell layers. As such, they have three distinct surfaces, an apical surface exposed to the lumen, a basolateral membrane that interacts with the basement membrane, and an "intercellular surface" forming the interaction region between adjacent cells. Without being bound by theory, we believe that some of the members of the Ig superfamily would generally be restricted to this third surface, the intercellular surface, as this would be the likely region to enable direct cell-cell communication.

Many proteins are involved in cell-to-cell interactions and cell interactions with the microenvironment. Some of these proteins are known to reside within the intercellular membrane region, including cadherens which contribute to adherens junctions, connexins which contribute to gap junctions, and claudins and occludin which contribute to tight junctions. In addition to these proteins, other proteins are thought to reside in the apical junctional complex created by the tight junctions and adherens junctions. For example, within some normal cellular architecture members of the Ig superfamily (e.g., receptors) would be expressed at the intercellular surfaces and would not be detected by a binding agent described herein. However, a cell with altered cellular morphology or a cell that has lost normal cellular architecture (e.g., a tumor cell or a virally-infected cell) may have aberrant exposure of a protein/receptor, for example, PVR, PVRL2, and/or PVRL3, making these cells detectable by surveillance with the binding agents described herein.

In addition, over-expression of a PVR family member on a cell's surface may make that cell a better target to cells expressing counter receptors (e.g., CTLs and/or NK cells). Interestingly, human PVR and PVRL2 have been found to be over-expressed on certain tumors, including colorectal cancer, gastric cancers, ovarian cancers, neuroblastomas, myeloid leukemias, and multiple myeloma (see, for example, Masson et al., 2001, *Gut*, 49:236-240; Tahara-Hanaoka et al., 2006, *Blood*, 107:1491-1496; Carlsten et al., 2007, *Cancer Res.*, 67:1317-1325; Castriconi et al., 2004, *Cancer Res.*, 64:9180-9184; Pende et al., 2005, *Blood*, 105:2066-2073; El-Sherbiny et al., 2007, *Cancer Res.*, 67:8444-8449).

Thus, the present invention provides methods of identifying a human subject for treatment with a binding agent, comprising determining if the subject has a tumor that has an elevated level of PVR as compared to expression of PVR in a reference sample or a pre-determined level of PVR. As used herein, a "reference sample" includes but is not limited to, normal tissue, non-cancerous tissue of the same tissue type, tumor tissue of the same tissue type, and tumor tissue of a different tissue type. Thus, in some embodiments, the level of expression of PVR in a tumor is compared to the level of expression of PVR in normal tissue. In some embodiments, the level of expression of PVR in a tumor is compared to the level of expression of PVR in non-cancerous tissue of the same tissue type. In some embodiments, the level of expression of PVR in a tumor is compared to the level of expression of PVR in tumors of the same tissue type. In some embodiments, the level of expression of PVR in a tumor is compared to the level of expression of PVR in tumors of a different tissue type. In some embodiments, the level of expression of PVR in a tumor is compared to a pre-determined level of PVR. In some embodiments, determining the level of PVR expression is done prior to treatment. In some embodiments, determining the level of PVR expression is by immunohistochemistry. In some embodiments, the subject is administered a binding agent described herein if the tumor has an elevated level of PVR expression as compared to the expression of PVR in the reference sample or the pre-determined level. For example, in some embodiments, the subject is administered a binding agent described herein if the tumor has an elevated level of PVR expression as compared to the level of PVR expression in a reference sample. In some embodiments, the subject is administered a binding agent described herein if the tumor has an elevated level of PVR expression as compared to a pre-determined level of PVR.

In some embodiments, if the tumor has an elevated level of PVR, the subject is selected for treatment with a binding agent that specifically binds TIGIT and/or CD96. In some embodiments, if selected for treatment, the subject is administered a binding agent described herein. In certain embodiments, the subject has had a tumor removed.

The present invention also provides methods of identifying a human subject for treatment with a binding agent, comprising determining if the subject has a tumor that has an aberrant expression of PVR as compared to expression of PVR in tissue of the same type or in a reference sample. In some embodiments, if the tumor has an aberrant expression of PVR, the subject is selected for treatment with a binding agent that specifically binds TIGIT and/or CD96. In some embodiments, if selected for treatment, the subject is administered a binding agent described herein. In certain embodiments, the subject has had a tumor removed.

The present invention also provides methods of selecting a human subject for treatment with a binding agent described herein, the method comprising determining if the subject has a tumor that has an elevated expression level of PVR, wherein if the tumor has an elevated expression level of PVR the subject is selected for treatment. In some embodiments, a method of inhibiting tumor growth in a human subject comprises determining if the tumor has an elevated expression level of PVR, and administering to the subject a therapeutically effective amount of a binding agent described herein. In some embodiments, a method of treating cancer in a human subject comprises (a) selecting a subject for treatment based, at least in part, on the subject having a cancer that has an elevated level of PVR, and (b)

administering to the subject a therapeutically effective amount of a binding agent described herein.

Methods for determining the level of PVR nucleic acid expression in a cell, tumor, or cancer are known by those of skill in the art. These methods include, but are not limited to, PCR-based assays, microarray analyses, and nucleotide sequencing (e.g., NextGen sequencing). Methods for determining the level of PVR protein expression in a cell, tumor, or cancer include, but are not limited to, Western blot analysis, protein arrays, ELISAs, immunohistochemistry (IHC), and FACS.

Methods for determining whether a tumor or cancer has an elevated level of PVR expression can use a variety of samples. In some embodiments, the sample is taken from a subject having a tumor or cancer. In some embodiments, the sample is a fresh tumor/cancer sample. In some embodiments, the sample is a frozen tumor/cancer sample. In some embodiments, the sample is a formalin-fixed paraffin-embedded sample. In some embodiments, the sample is a blood sample. In some embodiments, the sample is a plasma sample. In some embodiments, the sample is processed to a cell lysate. In some embodiments, the sample is processed to DNA or RNA.

The present invention further provides pharmaceutical compositions comprising the binding agents described herein. In certain embodiments, the pharmaceutical compositions further comprise a pharmaceutically acceptable vehicle. In some embodiments, the pharmaceutical compositions find use in immunotherapy. In some embodiments, the pharmaceutical compositions find use in inhibiting tumor growth in a subject (e.g., a human patient). In some embodiments, the pharmaceutical compositions find use in treating cancer in a subject (e.g., a human patient).

In certain embodiments, formulations are prepared for storage and use by combining a purified binding agent of the present invention with a pharmaceutically acceptable vehicle (e.g., a carrier or excipient). Suitable pharmaceutically acceptable vehicles include, but are not limited to, nontoxic buffers such as phosphate, citrate, and other organic acids; salts such as sodium chloride; antioxidants including ascorbic acid and methionine; preservatives such as octadecyldimethylbenzyl ammonium chloride, hexamethonium chloride, benzalkonium chloride, benzethonium chloride, phenol, butyl or benzyl alcohol, alkyl parabens, such as methyl or propyl paraben, catechol, resorcinol, cyclohexanol, 3-pentanol, and m-cresol; low molecular weight polypeptides (e.g., less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosaccharides, disaccharides, glucose, mannose, or dextrins; chelating agents such as EDTA; sugars such as sucrose, mannitol, trehalose or sorbitol; salt-forming counter-ions such as sodium; metal complexes such as Zn-protein complexes; and non-ionic surfactants such as TWEEN or polyethylene glycol (PEG). (*Remington: The Science and Practice of Pharmacy*, $22^{st}$ Edition, 2012, Pharmaceutical Press, London.).

The pharmaceutical compositions of the present invention can be administered in any number of ways for either local or systemic treatment. Administration can be topical by epidermal or transdermal patches, ointments, lotions, creams, gels, drops, suppositories, sprays, liquids and powders; pulmonary by inhalation or insufflation of powders or aerosols, including by nebulizer, intratracheal, and intranasal; oral; or parenteral including intravenous, intraarterial, intratumoral, subcutaneous, intraperitoneal, intramuscular (e.g., injection or infusion), or intracranial (e.g., intrathecal or intraventricular).

The therapeutic formulation can be in unit dosage form. Such formulations include tablets, pills, capsules, powders, granules, solutions or suspensions in water or non-aqueous media, or suppositories. In solid compositions such as tablets the principal active ingredient is mixed with a pharmaceutical carrier. Conventional tableting ingredients include corn starch, lactose, sucrose, sorbitol, talc, stearic acid, magnesium stearate, dicalcium phosphate or gums, and diluents (e.g., water). These can be used to form a solid preformulation composition containing a homogeneous mixture of a compound of the present invention, or a non-toxic pharmaceutically acceptable salt thereof. The solid preformulation composition is then subdivided into unit dosage forms of a type described above. The tablets, pills, etc. of the formulation or composition can be coated or otherwise compounded to provide a dosage form affording the advantage of prolonged action. For example, the tablet or pill can comprise an inner composition covered by an outer component. Furthermore, the two components can be separated by an enteric layer that serves to resist disintegration and permits the inner component to pass intact through the stomach or to be delayed in release. A variety of materials can be used for such enteric layers or coatings, such materials include a number of polymeric acids and mixtures of polymeric acids with such materials as shellac, cetyl alcohol and cellulose acetate.

The binding agents described herein can also be entrapped in microcapsules. Such microcapsules are prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules) or in macroemulsions as described in *Remington: The Science and Practice of Pharmacy*, $22^{st}$ Edition, 2012, Pharmaceutical Press, London.

In certain embodiments, pharmaceutical formulations include a binding agent of the present invention complexed with liposomes. Methods to produce liposomes are known to those of skill in the art. For example, some liposomes can be generated by reverse phase evaporation with a lipid composition comprising phosphatidylcholine, cholesterol, and PEG-derivatized phosphatidylethanolamine (PEG-PE). Liposomes can be extruded through filters of defined pore size to yield liposomes with the desired diameter.

In certain embodiments, sustained-release preparations can be produced. Suitable examples of sustained-release preparations include semi-permeable matrices of solid hydrophobic polymers containing a binding agent, where the matrices are in the form of shaped articles (e.g., films or microcapsules). Examples of sustained-release matrices include polyesters, hydrogels such as poly(2-hydroxyethylmethacrylate) or poly(vinyl alcohol), polylactides, copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

In certain embodiments, in addition to administering a binding agent, the method or treatment further comprises administering at least one immune response stimulating agent. In some embodiments, the immune response stimulating agent includes, but is not limited to, a colony stimulating factor (e.g., granulocyte-macrophage colony stimulating factor (GM-CSF), macrophage colony stimulating factor (M-CSF), granulocyte colony stimulating factor (G-CSF), stem cell factor (SCF)), an interleukin (e.g., IL-1, IL2, IL-3, IL-7, IL-12, IL-15, IL-18), an antibody that blocks immunosuppressive functions (e.g., an anti-CTLA4 antibody, anti-CD28 antibody, anti-CD3 antibody), a toll-like receptor (e.g., TLR4, TLR7, TLR9), or a member of the B7 family (e.g., CD80, CD86). An immune response stimulating agent can be administered prior to, concurrently with, and/or subsequently to, administration of the binding agent. Pharmaceutical compositions comprising a binding agent and the immune response stimulating agent(s) are also provided. In some embodiments, the immune response stimulating agent comprises 1, 2, 3, or more immune response stimulating agents.

In certain embodiments, in addition to administering a binding agent, the method or treatment further comprises administering at least one additional therapeutic agent. An additional therapeutic agent can be administered prior to, concurrently with, and/or subsequently to, administration of the binding agent. Pharmaceutical compositions comprising a binding agent and the additional therapeutic agent(s) are also provided. In some embodiments, the at least one additional therapeutic agent comprises 1, 2, 3, or more additional therapeutic agents.

Combination therapy with two or more therapeutic agents often uses agents that work by different mechanisms of action, although this is not required. Combination therapy using agents with different mechanisms of action may result in additive or synergetic effects. Combination therapy may allow for a lower dose of each agent than is used in monotherapy, thereby reducing toxic side effects and/or increasing the therapeutic index of the agent(s). Combination therapy may decrease the likelihood that resistant cancer cells will develop. In some embodiments, combination therapy comprises a therapeutic agent that affects the immune response (e.g., enhances or activates the response) and a therapeutic agent that affects (e.g., inhibits or kills) the tumor/cancer cells.

In some embodiments, the combination of a binding agent and at least one additional therapeutic agent results in additive or synergistic results. In some embodiments, the combination therapy results in an increase in the therapeutic index of the binding agent. In some embodiments, the combination therapy results in an increase in the therapeutic index of the additional agent(s). In some embodiments, the combination therapy results in a decrease in the toxicity and/or side effects of the binding agent. In some embodiments, the combination therapy results in a decrease in the toxicity and/or side effects of the additional agent(s).

Useful classes of therapeutic agents include, for example, antitubulin agents, auristatins, DNA minor groove binders, DNA replication inhibitors, alkylating agents (e.g., platinum complexes such as cisplatin, mono(platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, purine antimetabolites, puromycins, radiation sensitizers, steroids, taxanes, topoisomerase inhibitors, vinca alkaloids, or the like. In certain embodiments, the second therapeutic agent is an alkylating agent, an antimetabolite, an antimitotic, a topoisomerase inhibitor, or an angiogenesis inhibitor.

Therapeutic agents that may be administered in combination with the binding agents described herein include chemotherapeutic agents. Thus, in some embodiments, the method or treatment involves the administration of a binding agent of the present invention in combination with a chemotherapeutic agent or in combination with a cocktail of chemotherapeutic agents. Treatment with a binding agent can occur prior to, concurrently with, or subsequent to administration of chemotherapies. Combined administration can include co-administration, either in a single pharmaceutical formulation or using separate formulations, or consecutive administration in either order but generally within a time period such that all active agents can exert their biological activities simultaneously. Preparation and dosing schedules for such chemotherapeutic agents can be used according to manufacturers' instructions or as determined empirically by the skilled practitioner. Preparation and dosing schedules for such chemotherapy are also described in *The Chemotherapy Source Book*, 4$^{th}$ *Edition*, 2008, M. C. Perry, Editor, Lippincott, Williams & Wilkins, Philadelphia, Pa.

Chemotherapeutic agents useful in the instant invention include, but are not limited to, alkylating agents such as thiotepa and cyclosphosphamide (CYTOXAN); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytosine arabinoside, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenishers such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofuran; spirogermanium; tenuazonic acid; triaziquone; 2,2', 2"-trichlorotriethylamine; urethan; vindesine; dacarbazine; mannomustine; mitobronitol; mitolactol; pipobroman; gacytosine; arabinoside (Ara-C); taxoids, e.g. paclitaxel (TAXOL) and docetaxel (TAXOTERE); chlorambucil; gemcitabine; 6-thioguanine; mercaptopurine; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; ibandronate; CPT11; topoisomerase inhibitor RFS 2000; difluoromethylornithine (DMFO); retinoic acid; esperamicins; capecitabine (XELODA); and pharmaceutically acceptable salts, acids or derivatives of any of the above. Chemotherapeutic agents also include anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (FARESTON); and anti-androgens such as flutamide, nilutamide, bicalutamide, leuprolide, and goserelin; and pharmaceutically acceptable salts, acids or derivatives of any of the above. In certain embodiments, the additional therapeutic agent is cisplatin. In certain embodiments, the additional therapeutic agent is carboplatin.

In certain embodiments, the chemotherapeutic agent is a topoisomerase inhibitor. Topoisomerase inhibitors are chemotherapy agents that interfere with the action of a topoisomerase enzyme (e.g., topoisomerase I or II). Topoisomerase inhibitors include, but are not limited to, doxorubicin HCl, daunorubicin citrate, mitoxantrone HCl, actinomycin D, etoposide, topotecan HCl, teniposide (VM-26), and irinotecan, as well as pharmaceutically acceptable salts, acids, or derivatives of any of these. In some embodiments, the additional therapeutic agent is irinotecan.

In certain embodiments, the chemotherapeutic agent is an anti-metabolite. An anti-metabolite is a chemical with a structure that is similar to a metabolite required for normal biochemical reactions, yet different enough to interfere with one or more normal functions of cells, such as cell division. Anti-metabolites include, but are not limited to, gemcitabine, fluorouracil, capecitabine, methotrexate sodium, ralitrexed, pemetrexed, tegafur, cytosine arabinoside, thioguanine, 5-azacytidine, 6-mercaptopurine, azathioprine, 6-thioguanine, pentostatin, fludarabine phosphate, and cladribine, as well as pharmaceutically acceptable salts, acids, or derivatives of any of these. In certain embodiments, the additional therapeutic agent is gemcitabine.

In certain embodiments, the chemotherapeutic agent is an antimitotic agent, including, but not limited to, agents that bind tubulin. In some embodiments, the agent is a taxane. In certain embodiments, the agent is paclitaxel or docetaxel, or a pharmaceutically acceptable salt, acid, or derivative of paclitaxel or docetaxel. In certain embodiments, the agent is paclitaxel (TAXOL), docetaxel (TAXOTERE), albumin-bound paclitaxel (ABRAXANE), DHA-paclitaxel, or PG-paclitaxel. In certain alternative embodiments, the antimitotic agent comprises a vinca alkaloid, such as vincristine, binblastine, vinorelbine, or vindesine, or pharmaceutically acceptable salts, acids, or derivatives thereof. In some embodiments, the antimitotic agent is an inhibitor of kinesin Eg5 or an inhibitor of a mitotic kinase such as Aurora A or Plk1. In certain embodiments, the additional therapeutic agent is paclitaxel.

In some embodiments, an additional therapeutic agent comprises an agent such as a small molecule. For example, treatment can involve the combined administration of a binding agent of the present invention with a small molecule that acts as an inhibitor against tumor-associated antigens including, but not limited to, EGFR, HER2 (ErbB2), and/or VEGF. In some embodiments, a binding agent of the present invention is administered in combination with a protein kinase inhibitor selected from the group consisting of: gefitinib (IRESSA), erlotinib (TARCEVA), sunitinib (SUTENT), lapatanib, vandetanib (ZACTIMA), AEE788, CI-1033, cediranib (RECENTIN), sorafenib (NEXAVAR), and pazopanib (GW786034B). In some embodiments, an additional therapeutic agent comprises an mTOR inhibitor.

In certain embodiments, the additional therapeutic agent is a small molecule that inhibits a cancer stem cell pathway. In some embodiments, the additional therapeutic agent is an inhibitor of the Notch pathway. In some embodiments, the additional therapeutic agent is an inhibitor of the Wnt pathway. In some embodiments, the additional therapeutic agent is an inhibitor of the BMP pathway. In some embodiments, the additional therapeutic agent is an inhibitor of the Hippo pathway. In some embodiments, the additional therapeutic agent is an inhibitor of the mTOR/AKR pathway.

In some embodiments, an additional therapeutic agent comprises a biological molecule, such as an antibody. For example, treatment can involve the combined administration of a binding agent of the present invention with antibodies against tumor-associated antigens including, but not limited to, antibodies that bind EGFR, HER2/ErbB2, and/or VEGF. In certain embodiments, the additional therapeutic agent is an antibody specific for a cancer stem cell marker. In some embodiments, the additional therapeutic agent is an antibody that binds a component of the Notch pathway. In some embodiments, the additional therapeutic agent is an antibody that binds a component of the Wnt pathway. In certain embodiments, the additional therapeutic agent is an antibody that inhibits a cancer stem cell pathway. In some embodiments, the additional therapeutic agent is an inhibitor of the Notch pathway. In some embodiments, the additional therapeutic agent is an inhibitor of the Wnt pathway. In some embodiments, the additional therapeutic agent is an inhibitor of the BMP pathway. In some embodiments, the additional therapeutic agent is an antibody that inhibits β-catenin signaling. In certain embodiments, the additional therapeutic agent is an antibody that is an angiogenesis inhibitor (e.g., an anti-VEGF or VEGF receptor antibody). In certain embodiments, the additional therapeutic agent is bevacizumab (AVASTIN), ramucirumab, trastuzumab (HERCEPTIN), pertuzumab (OMNITARG), panitumumab (VECTIBIX), nimotuzumab, zalutumumab, or cetuximab (ERBITUX).

Furthermore, treatment with a binding agent described herein can include combination treatment with other biologic molecules, such as one or more cytokines (e.g., lymphokines, interleukins, tumor necrosis factors, and/or growth factors) or can be accompanied by surgical removal of tumors, removal of cancer cells, or any other therapy deemed necessary by a treating physician.

In some embodiments, the binding agent can be combined with a growth factor selected from the group consisting of, but not limited to: adrenomedullin (AM), angiopoietin (Ang), BMPs, BDNF, EGF, erythropoietin (EPO), FGF, GDNF, G-CSF, GM-CSF, GDF9, HGF, HDGF, IGF, migration-stimulating factor, myostatin (GDF-8), NGF, neurotrophins, PDGF, thrombopoietin, TGF-α, TGF-β, TNF-α, VEGF, PlGF, IL-1, IL-2, IL-3, IL-4, IL-5, IL-6, IL-7, IL-12, IL-15, and IL-18.

In certain embodiments, the treatment involves the administration of a binding agent of the present invention in combination with radiation therapy. Treatment with a binding agent can occur prior to, concurrently with, or subsequent to administration of radiation therapy. Dosing schedules for such radiation therapy can be determined by the skilled medical practitioner.

In certain embodiments, the treatment involves the administration of a binding agent of the present invention in combination with anti-viral therapy. Treatment with a binding agent can occur prior to, concurrently with, or subsequent to administration of antiviral therapy. The anti-viral drug used in combination therapy will depend upon the virus the subject is infected with.

Combined administration can include co-administration, either in a single pharmaceutical formulation or using separate formulations, or consecutive administration in either order but generally within a time period such that all active agents can exert their biological activities simultaneously.

It will be appreciated that the combination of a binding agent and at least one additional therapeutic agent may be administered in any order or concurrently. In some embodiments, the binding agent will be administered to patients that have previously undergone treatment with a second therapeutic agent. In certain other embodiments, the binding agent and a second therapeutic agent will be administered substantially simultaneously or concurrently. For example, a subject may be given a binding agent (e.g., a soluble receptor) while undergoing a course of treatment with a second therapeutic agent (e.g., chemotherapy). In certain embodiments, a binding agent will be administered within 1 year of the treatment with a second therapeutic agent. In certain alternative embodiments, a binding agent will be administered within 10, 8, 6, 4, or 2 months of any treatment with a second therapeutic agent. In certain other embodiments, a binding agent will be administered within 4, 3, 2, or 1 weeks of any treatment with a second therapeutic agent. In some embodiments, a binding agent will be administered within 5, 4, 3, 2, or 1 days of any treatment with a second therapeutic agent. It will further be appreciated that the two (or more) agents or treatments may be administered to the subject within a matter of hours or minutes (i.e., substantially simultaneously).

For the treatment of a disease, the appropriate dosage of a binding agent of the present invention depends on the type of disease to be treated, the severity and course of the disease, the responsiveness of the disease, whether the binding agent is administered for therapeutic or preventative purposes, previous therapy, the patient's clinical history, and so on, all at the discretion of the treating physician. The binding agent can be administered one time or over a series of treatments lasting from several days to several months, or until a cure is effected or a diminution of the disease state is achieved (e.g., reduction in tumor size). Optimal dosing schedules can be calculated from measurements of drug accumulation in the body of the patient and will vary depending on the relative potency of an individual agent. The administering physician can determine optimum dosages, dosing methodologies, and repetition rates. In certain embodiments, dosage is from 0.01 µg to 100 mg/kg of body weight, from 0.1 µg to 100 mg/kg of body weight, from 1 µg to 100 mg/kg of body weight, from 1 mg to 100 mg/kg of body weight, 1 mg to 80 mg/kg of body weight from 10 mg to 100 mg/kg of body weight, from 10 mg to 75 mg/kg of body weight, or from 10 mg to 50 mg/kg of body weight. In certain embodiments, the dosage of the binding agent is from about 0.1 mg to about 20 mg/kg of body weight. In some embodiments, the dosage of the binding agent is about 0.5 mg/kg of body weight. In some embodiments, the dosage of the binding agent is about 1 mg/kg of body weight. In some embodiments, the dosage of the binding agent is about 1.5 mg/kg of body weight. In some embodiments, the dosage of the binding agent is about 2 mg/kg of body weight. In some embodiments, the dosage of the binding agent is about 2.5 mg/kg of body weight. In some embodiments, the dosage of the binding agent is about 5 mg/kg of body weight. In some embodiments, the dosage of the binding agent is about 7.5 mg/kg of body weight. In some embodiments, the dosage of the binding agent is about 10 mg/kg of body weight. In some embodiments, the dosage of the binding agent is about 12.5 mg/kg of body weight. In some embodiments, the dosage of the binding agent is about 15 mg/kg of body weight. In certain embodiments, the dosage can be given once or more daily, weekly, monthly, or yearly. In certain embodiments, the binding agent is given once every week, once every two weeks, once every three weeks, or once every four weeks.

In some embodiments, a binding agent may be administered at an initial higher "loading" dose, followed by one or more lower doses. In some embodiments, the frequency of administration may also change. In some embodiments, a dosing regimen may comprise administering an initial dose, followed by additional doses (or "maintenance" doses) once a week, once every two weeks, once every three weeks, or once every month. For example, a dosing regimen may comprise administering an initial loading dose, followed by a weekly maintenance dose of, for example, one-half of the initial dose. Or a dosing regimen may comprise administering an initial loading dose, followed by maintenance doses of, for example one-half of the initial dose every other week. Or a dosing regimen may comprise administering three initial doses for 3 weeks, followed by maintenance doses of, for example, the same amount every other week.

As is known to those of skill in the art, administration of any therapeutic agent may lead to side effects and/or toxicities. In some cases, the side effects and/or toxicities are so severe as to preclude administration of the particular agent at a therapeutically effective dose. In some cases, drug therapy must be discontinued, and other agents may be tried. However, many agents in the same therapeutic class often display similar side effects and/or toxicities, meaning that the patient either has to stop therapy, or if possible, suffer from the unpleasant side effects associated with the therapeutic agent.

Thus, the present invention provides methods of administering to a subject the binding agents described herein comprising using an intermittent dosing strategy for administering one or more agents, which may reduce side effects and/or toxicities associated with administration of a binding agent, chemotherapeutic agent, etc. In some embodiments, a method for treating cancer in a human subject comprises administering to the subject a therapeutically effective dose of a binding agent in combination with a therapeutically effective dose of a chemotherapeutic agent, wherein one or both of the agents are administered according to an intermittent dosing strategy. In some embodiments, the intermittent dosing strategy comprises administering an initial dose of a binding agent to the subject, and administering subsequent doses of the binding agent about once every 2 weeks. In some embodiments, the intermittent dosing strategy comprises administering an initial dose of a binding agent to the subject, and administering subsequent doses of the binding agent about once every 3 weeks. In some embodiments, the intermittent dosing strategy comprises administering an initial dose of a binding agent to the subject, and administering subsequent doses of the binding agent about once every 4 weeks. In some embodiments, the binding agent is administered using an intermittent dosing strategy and the chemotherapeutic agent is administered weekly.

V. Screening

The present invention provides screening methods to identify agents that modulate the immune response. In some embodiments, the present invention provides methods for screening candidate agents, including but not limited to, proteins, peptides, peptidomimetics, small molecules, compounds, or other drugs, which modulate the immune response.

In some embodiments, a method of screening for a candidate agent that modulates the immune response comprises determining if the agent has an effect on immune response cells. In some embodiments, a method of screening for a candidate agent that modulates the immune response comprises determining if the agent is capable of increasing the activity of immune cells. In some embodiments, a method of screening for a candidate agent that modulates the immune response comprises determining if the agent is capable of increasing the activity of cytolytic cells, such as CTLs and/or NK cells.

VI. Kits Comprising Binding Agents

The present invention provides kits that comprise the binding agents described herein and that can be used to perform the methods described herein. In certain embodiments, a kit comprises at least one purified binding agent in one or more containers. In some embodiments, the kits contain all of the components necessary and/or sufficient to perform a detection assay, including all controls, directions for performing assays, and any necessary software for analysis and presentation of results. One skilled in the art will readily recognize that the disclosed binding agents of the present invention can be readily incorporated into one of the established kit formats which are well known in the art.

Further provided are kits that comprise a binding agent as well as at least one additional therapeutic agent. In certain embodiments, the second (or more) therapeutic agent is a chemotherapeutic agent. In certain embodiments, the second (or more) therapeutic agent is an angiogenesis inhibitor.

Embodiments of the present disclosure can be further defined by reference to the following non-limiting examples, which describe in detail preparation of certain antibodies of the present disclosure and methods for using antibodies of the present disclosure. It will be apparent to those skilled in the art that many modifications, both to materials and methods, may be practiced without departing from the scope of the present disclosure.

EXAMPLES

Example 1

PVR Family Constructs

Protein constructs of PVR family members TIGIT, CD96, CD226, PVRL1, PVRL2, PVRL3, PVRL4, PVR, and PVR variants were prepared including membrane-anchored proteins and soluble receptors (FIG. 2). Each membrane-anchored receptor was designed to be non-functional in regard to signaling, as the transmembrane and cytoplasmic domains were replaced with the human CD4 transmembrane domain and an intracellular green fluorescent protein (GFP) tag. The membrane-anchored protein constructs were generated by ligating at least one domain of the extracellular domain (ECD) of a human PVR family protein to the transmembrane domain of CD4 and a C-terminal GFP protein tag using standard recombinant DNA techniques. These constructs are referred to as "PVR family member"-CD4TM-GFP, for example PVR-CD4TM-GFP. The soluble receptors were designed to include at least one domain of the ECD linked to an immunoglobulin Fc domain. The soluble receptor PVR family protein constructs were generated by ligating the ECD region of human PVR family member proteins to the Fc domain of human IgG1 using standard recombinant DNA techniques. These constructs are referred to as "PVR family member"-Fc, for example CD226-Fc. As known to those of skill in the art, the ECD region of any given protein used in the constructs may comprise the ECD or comprise a fragment of the ECD, for example just a IgV domain. Also, what is considered to be the ECD or an Ig domain may vary by one, two, three, or more amino acids at the amino end, the carboxyl end, or both ends of the domain. These fusion proteins may be used to examine the binding interactions of the PVR family members.

The constructs generated include ECD regions, or a fragment thereof, from the PVR family members in Table 2.

TABLE 2

| Name | Full name | Other names | UniProtKB No. | SEQ ID NO |
|---|---|---|---|---|
| PVR Family | | | | |
| PVR | Poliovirus receptor | NECL-5, CD155, PVS | P15151 | |
| PVRL1 | Poliovirus receptor-related protein 1 | HVEC, HLGR, Nectin-1, CD111, PRR1 | Q15223 | |
| PVRL2 | Poliovirus receptor-related protein 2 | HVEB, PRR2, CD112, Nectin-2 | Q92692 | |
| PVRL3 | Poliovirus receptor-related protein 3 | Nectin-3, CD113 | Q9NQS3 | |
| PVRL4 | Poliovirus receptor-related protein 4 | Nectin-4, LNIR, PRR4 | Q96NY8 | |
| CD226 | CD226 antigen | DNAM1, PTA-1, TLiSA1 | Q15762 | |
| CD96 | T-cell surface protein tactile | | P40200 | |
| TIGIT | T-cell immunoreceptor with Ig and ITIM domains | VSIG9, Vstm3, WUCAM | Q495A1 | |

Example 2

Binding Interactions Between PVR Family Members

The binding interactions among members of the PVR family were examined by flow cytometry. Each of the family members was expressed both as an Fc fusion protein containing at least one domain of the ECD of the receptor fused to the Fc region of human IgG1, and also as an membrane-anchored form containing at least one domain of the ECD of the receptor fused to a human CD4 transmembrane region and an intracellular green fluorescent (GFP) protein tag (see Example 1).

Individual potential binding interactions were assessed by transfection of HEK-293T cells with an expression vector encoding a specific membrane-anchored receptor (PVR, PVRL1, PVRL2, PVRL3, or PVRL4), and then examining the ability of a specific receptor-Fc fusion protein (CD96, TIGIT, or CD226) to bind to the transfected cells. HEK-293T cells were transiently transfected with a cDNA expression vector encoding PVR-CD4TM-GFP, PVRL1-CD4TM-GFP, PVRL2-CD4TM-GFP, PVRL3-CD4TM-GFP, or PVRL4-CD4TM-GFP and then subsequently mixed with soluble CD226-Fc, TIGIT-Fc, or CD96-Fc fusion proteins. In addition, individual potential binding interactions were assessed by transfection of HEK-293T cells with an expression vector encoding a specific membrane-anchored receptor (PVR, PVRL1, PVRL2, PVRL3, or PVRL4), and then examining the ability of a specific receptor-Fc fusion protein (PVR, PVRL1, PVRL2, PVRL3, or PVRL4) to bind to the transfected cells. HEK-293T cells were transiently transfected with a cDNA expression vector encoding PVR-CD4TM-GFP, PVRL1-CD4TM-GFP, PVRL2-CD4TM-GFP, PVRL3-CD4TM-GFP, or PVRL4-CD4TM-GFP and then subsequently mixed with soluble PVR-Fc, PVRL1-Fc, PVRL2-Fc, PVRL3-Fc, or PVRL4-Fc fusion proteins. Binding was detected by subsequent staining of the cells with an anti-human Fc antibody conjugated to phytoerythrin (PE) and analysis using flow cytometry.

Figure 3A:
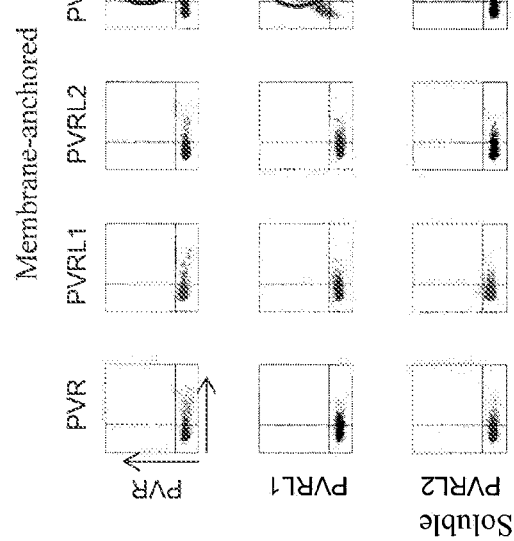
Figure 3B:
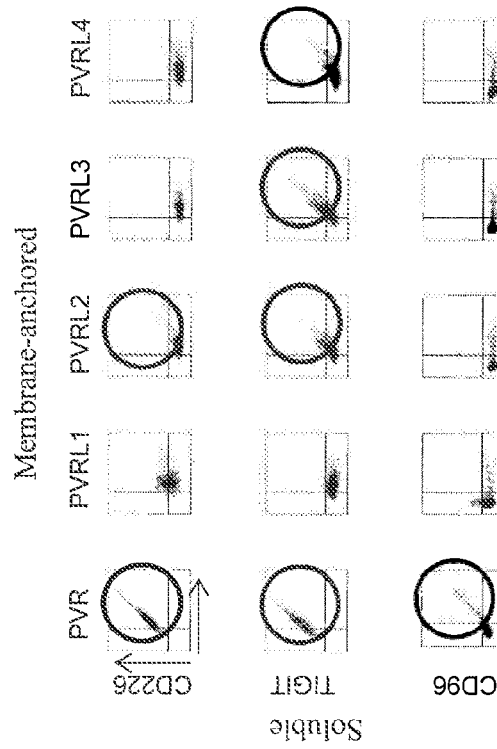

As shown in FIG. 3A, membrane-anchored PVR was bound by soluble receptors CD226, TIGIT and CD96. In addition, soluble receptor CD226 weakly bound to PVRL2, and soluble receptor TIGIT bound to PVRL2, PVRL3, and PVRL4. As shown in FIG. 3B, soluble receptor PVR bound PVRL3, soluble receptor PVRL1 bound PVRL3 and PVRL4; soluble receptor PVRL3 bound PVRL1, PVRL2 and PVR; and soluble receptor PVRL4 bound PVRL1. Positive binding interactions are highlighted by circles. Also shown is a schematic representation of the observed binding interactions between different members of the PVR family (FIG. 3C). Some of the indicated binding interactions observed during this analysis appear to be new.

Example 3

Generation of PVR Variants

The crystal structure of PVR bound to TIGIT has been previously disclosed (see, Stengel et al., 2012, *PNAS*, 109: 5399-5404). The structure was examined and residues within PVR that appeared to not be critical for TIGIT binding, but might potentially impact the binding of CD226 or CD96 were selected. These residues are highlighted in FIG. 4. A cDNA expression library of variant human PVR N-terminal IgV domain molecules was designed and generated in which amino acid positions 65, 67, 72, 73, 74, 81, 82, 84, and 85 (SEQ ID NO:18) were individually substituted with all twenty amino acids. The cDNA expression vector encoded the N-terminal IgV domain of PVR fused to a CD4 transmembrane domain and a green fluorescent protein (GFP) tag. The expression vector plasmid also contained a bacterial ampicillin resistance gene. The cDNA library of variant PVR molecules was transfected into CAP-T cells in the presence of a 100-fold excess of an irrelevant vector lacking ampicillin resistance. CAP-T cells are an immortalized amniocyte cell line, stably expressing the SV40 large T antigen (CEVEC Pharmaceuticals, Koln Germany). This strategy was designed to reduce the number of unique PVR variant plasmids transfected per cell. Forty-eight hours after transfection, cells were incubated with fluorescently-labeled TIGIT-Fc, CD96-Fc, CD226-Fc, a combination of TIGIT-Fc and CD226-Fc, or a combination of CD96-Fc and CD226-Fc. The cells were analyzed by fluorescence activated cell sorting (FACS) to isolate cells that displayed binding to either TIGIT or CD96, but lacked binding to CD226. Plasmids were recovered from the isolated cells, used to transformed bacteria, and the bacteria were plated on ampicillin-containing plates. Plasmids from individual colonies were sequenced and analyzed. In this manner amino acid substitutions that enable relative binding of PVR to TIGIT, CD96 and CD226 were identified.

FIG. 5 shows the binding pattern of two such amino acid variants. PVR variant S72N (serine to asparagine) did not significantly impact the binding to TIGIT or CD96 as compared to wild-type PVR, but the PVR variant S72N had substantially reduced binding to CD226 as compared to wild-type PVR. Another variant, PVR variant Q82K (glutamine to lysine) appeared to have increased the binding to TIGIT compared to wild-type PVR with a different binding pattern in the presence of TIGIT and CD226. This may allow TIGIT to more effectively compete with CD226 for binding to available variant PVRs.

Example 4

Natural Killer (NK) Cell Cytotoxicity Assays

The human chronic myelogenous leukemia cell line K562 and the human lung adenocarcinoma cell line A549 are cultured in RPMI 1640 culture medium (Gibco/Life Technologies, Carlsbad, Calif.) supplemented with 10% (v/v) fetal bovine serum (FBS), 2 mM L-glutamine, 100 U/ml penicillin, and 100 μg/ml streptomycin (Gibco) at 37° C. in a humidified atmosphere of 5% $CO_2$. K562 cells are transfected with GFP, human PVR, or the human PVR variants (4 μg DNA per $2\times10^6$ cells) via electroporation using an Amaxa Nucleofector device and Nucleofector Kit V according to the manufacturer's recommendations (Lonza, Basel, Switzerland). Transfection efficiency is routinely 60-70%, as assessed by flow cytometry for GFP positivity. A549 cells are transfected with the same constructs (3 μg DNA per $1\times10^6$ cells) using FuGENE 6 (Promega, Madison, Wis.) according to the manufacturer's instructions. Transfection efficacy is routinely >95%.

Primary human NK cells are isolated directly from fresh peripheral blood buffy coats (Stanford Blood Center, Palo Alto, Calif.) by 30-minute incubation with RosetteSep NK Cell Enrichment Cocktail (Stem Cell Technologies, Vancouver, British Columbia, Canada) prior to Ficoll-Hypaque density gradient centrifugation (Stem Cell Technologies). Human NK cells are cultured in L-glutamine-free RPMI 1640 medium supplemented with 10% FBS, 100 U/ml of penicillin, and 100 μg/ml of streptomycin. Isolated NK cells are routinely >98% CD56+CD3− by flow cytometry. The NK cell line NK-92 was purchased from the American Type Culture Collection (Manassas, Va.) and is maintained in RPMI 1640 containing 20% FBS, 100 U/ml penicillin, 100 µg/ml streptomycin, and 150 U/ml recombinant human IL-2.

NK-92 cells or primary human NK cells are plated in 96-well V-bottom plates with or without 300 U/ml recombinant human IL-2 (PeproTech, Rocky Hill, N.J.) and incubated overnight at 37° C. In some experiments, NK-92 cells or primary NK cells are incubated with 10 µg/ml of specific blocking antibodies to NKp30, NKp46, or NKG2D (Biolegend, San Diego, Calif.), or an equivalent amount of isotype-matched polyclonal human IgG (Sigma-Aldrich, St. Louis, Mo.) for 30 minutes at 4° C. prior to use in cytotoxicity assays. Target cells (K562 or A549 cells transfected with GFP, human PVR, or human PVR variants) are labeled with 10 µM calcein AM (Life Technologies) for 1 hour at 37° C. and then combined with the NK cells at various effector:target ratios (50:1-3:1). Following a 4-hour incubation at 37° C., cell-free supernatants are harvested and calcein release is quantified on a fluorometer at an excitation of 485 nm and an emission of 535 nm. The percentage of specific cell lysis is determined as: % lysis=100×(ER−SR)/(MR−SR), where ER, SR, and MR represent experimental, spontaneous, and maximum calcein release, respectively. Spontaneous release is the fluorescence emitted by target cells incubated in media alone (i.e., in the absence of effector cells), while maximum release is determined by lysing target cells with an equal volume of 10% SDS.

In some experiments, NK cell cytotoxicity is evaluated in the presence of soluble human PVR-Fc or the human PVR-Fc variants. Primary human NK cells or NK-92 cells are plated as described above, with the addition of 10 µg/ml of PVR-Fc or the human PVR-Fc variants. NK cell lysis against K562 cells or A549 cells is analyzed as described above.

Freshly isolated primary human NK cells were incubated overnight at 37° C. with or without 300 IU/ml recombinant human IL-2 (PeproTech, Rocky Hill, N.J.). The NK cells were then pre-treated with 30 µg/ml of PVR-Fc variant Q82K (gray bar), PVR-Fc wild-type control (black bar), or medium only (white bar) for 30 minutes at 4° C. in HBSS. The NK cells were washed, resuspended in media supplemented with an additional 30 µg/ml of the PVR-Fc variant or PVR-Fc WT, and plated in 96-well V-bottom plates. Target cells (HEK-293T cells or K562 cells) were labeled with 10 µM calcein AM (Life Technologies, Grand Island N.Y.) for 2 hours at 37° C. and then mixed with the NK cells at an effector:target ratio of 12:1. Following a 4-hour incubation at 37° C., cell-free supernatants were harvested and calcein release was quantified on a fluorometer at an excitation of 485 nm and an emission of 535 nm. The percentage of specific cell lysis was determined as described above.

Figure 6:
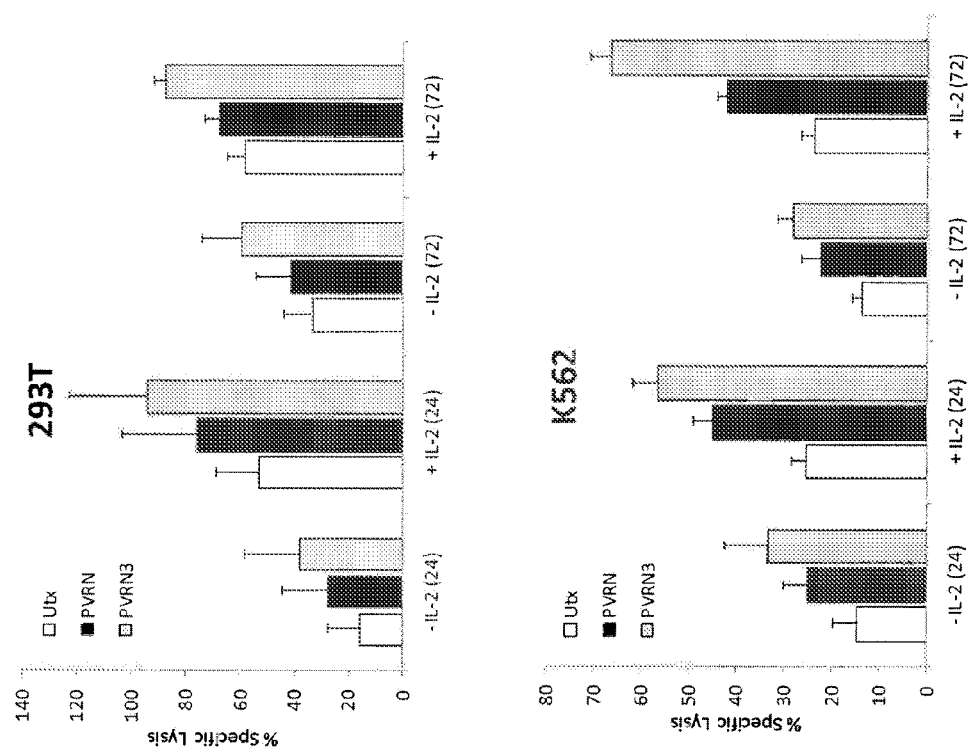
FIG. 6. Natural Killer Cell Cytotoxicity assay. Human NK cells were pre-treated with 30 µg/ml of PVR-Fc variant Q82K (gray bar), PVR-Fc wild-type control (black bar), or medium only (white bar). Target cells (HEK-293T cells or K562 cells) were labeled with 10 µM calcein AM mixed with the NK cells at an effector:target ratio of 12:1. Supernatants were harvested and calcein release was quantified on a fluorometer at an excitation of 485 nm and an emission of 535 nm.

NK cells demonstrated an increased ability to kill target cells when treated with PVR variant Q82K as compared to untreated NK cells or NK cells treated with a wild-type PVR (FIG. 6). Cell lysis was increased with the addition of IL-2 in all samples.

NK activation and/or activity can also be assessed by measuring the amount of IFN-gamma that is produced by NK cells during an assay. Wells of a 96-well flat-bottom culture plate were seeded with HEK-293T or A549 cells at a density of $5 \times 10^4$ target cells/well. Target cells were grown to confluence overnight. Freshly isolated human NK cells were pre-treated with 30 µg/ml of PVR-Fc variant Q82K (gray bar), PVR-Fc wild-type control (black bar), or medium only (white bar) for 30 minutes at 4° C. in HBSS. NK cells were then washed, resuspended in media supplemented with an additional 30 µg/ml of the PVR-Fc variant or PVR-Fc WT, and added to the target cells at $2 \times 10^5$ cells/well in media containing 300 IU/ml human IL-2. A duplicate set of cells were set up in media without human IL-2. Culture supernatants were harvested after 24 hours and analyzed for IFN-gamma content by ELISA (R&D Systems, Minneapolis, Minn.).

Figure 7:
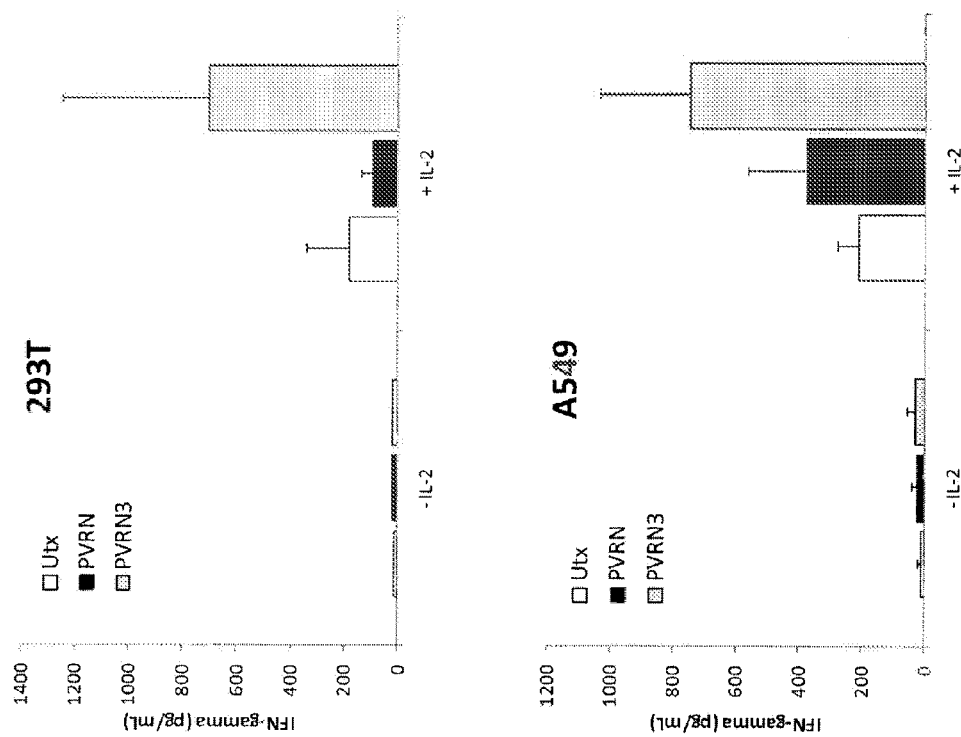
FIG. 7. Natural Killer Cytotoxicity assay. HEK-293T or A549 cells were seeded into plates and grown to confluence overnight. NK cells were pre-treated with 30 µg/ml of PVR-Fc variant Q82K (gray bar), PVR-Fc wild-type control (black bar), or medium only (white bar) and added to the target cells with or without human IL-2. Culture supernatants were harvested after 24 hours and analyzed for IFN-gamma content by ELISA (R&D Systems, Minneapolis, Minn.).

In the absence of IL-2, the NK cells produced very limited amounts of IFN-gamma and there appeared to be little difference between the different samples. In contrast, in the presence of IL-2, the NK cells produced higher levels of IFN-gamma when pre-treated with the PVR-Fc variant Q82K as compared to PVR-Fc wild-type or untreated controls (FIG. 7).

Example 5

FACS Analysis of Binding Interactions Between PVR Variants and TIGIT, CD226 and PVRL3

HEK-293T cells were transiently transfected with a cDNA expression vector encoding PVR-CD4TM-GFP, PVR S72N variant-CD4TM-GFP, PVR Q82K variant-CD4TM-GFP, or PVR Q82K+S72N double variant-CD4TM-GFP. After 24 hours, cells were mixed with soluble TIGIT-Fc, CD226-Fc or PVRL3-Fc fusion proteins and then subsequently stained with PE-conjugated anti-human Fc secondary antibody. Fusion protein binding was then analyzed by flow cytometry.

Figure 8A:
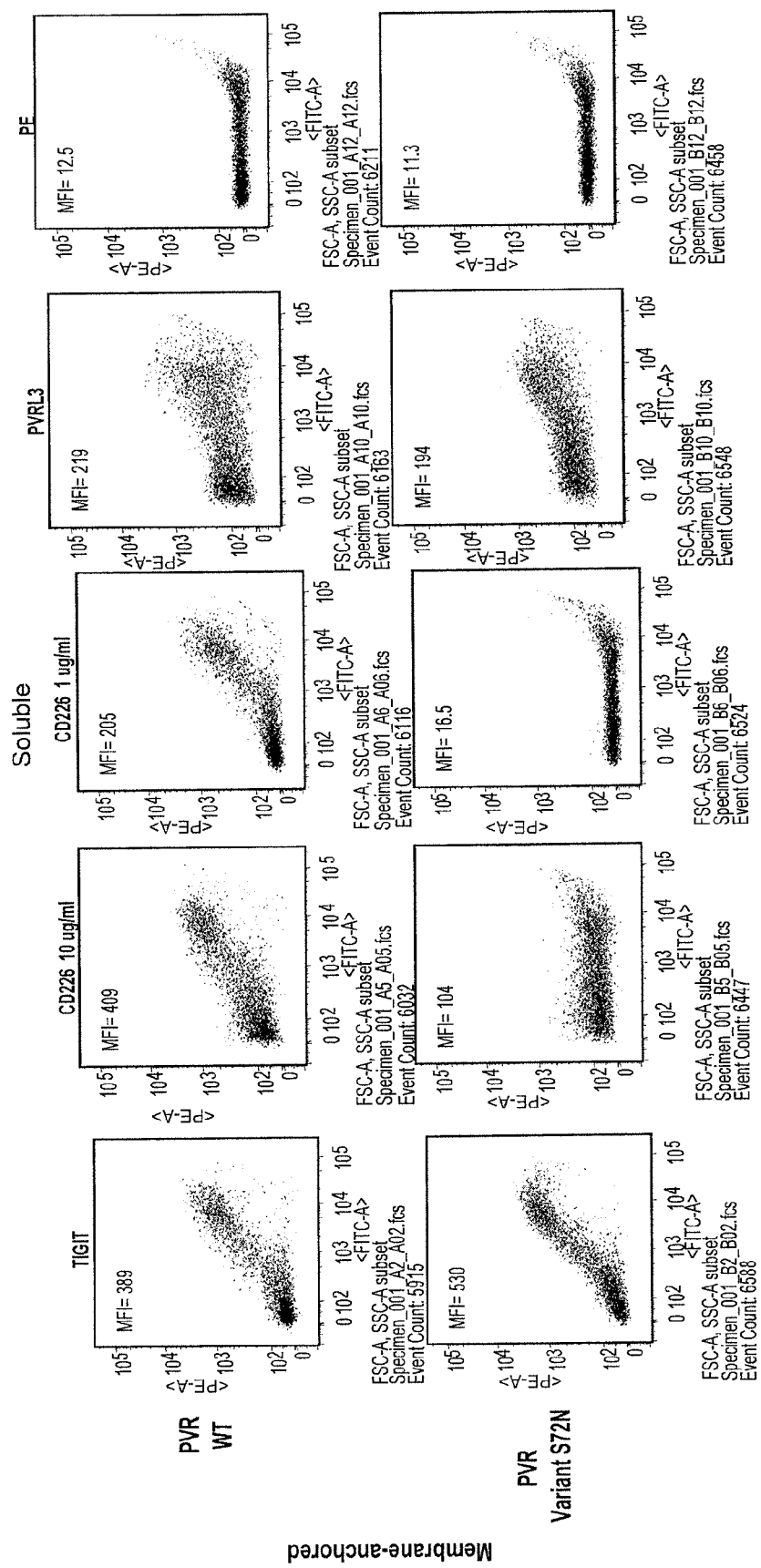
FIGS. 8A and 8B. FACS analysis of binding interactions between PVR variants and TIGIT, CD226, and PVRL3. HEK-293T cells were transiently transfected with a cDNA expression vector encoding (8A) PVR-CD4TM-GFP, (8A) PVR S72N variant-CD4TM-GFP, (8B) PVR Q82K variant-CD4TM-GFP, or (8B) PVR Q82K+S72N double variant-CD4TM-GFP. After 24 hours, cells were mixed with soluble TIGIT-Fc, CD226-Fc, or PVRL3-Fc fusion proteins and then subsequently stained with PE-conjugated anti-human Fc secondary antibody. Fusion protein binding was then analyzed by flow cytometry.
Figure 8B:
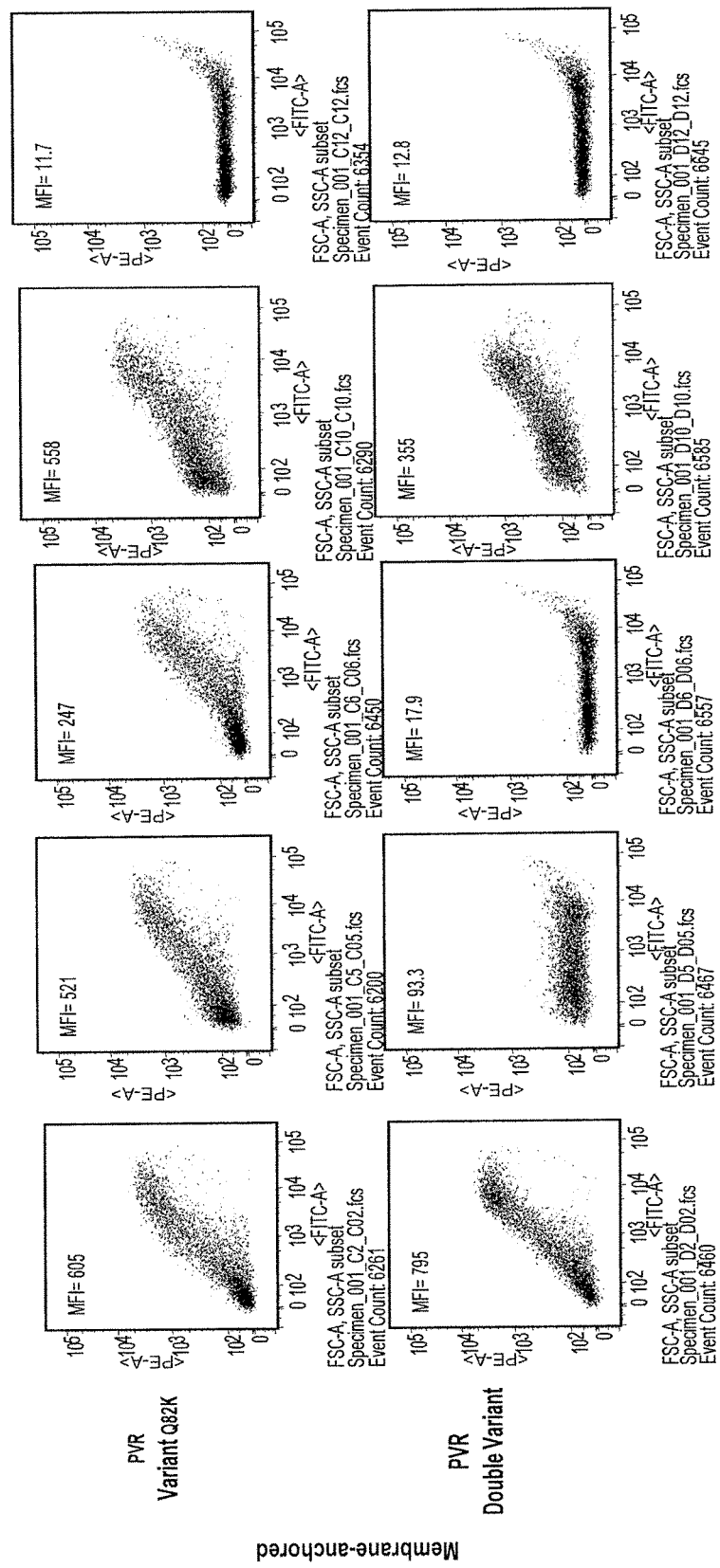

The results show that the double mutant PVR fusion protein exhibits improved binding to TIGIT as compared to parental wild-type PVR, but no detectable binding to CD226 (FIGS. 8A and 8B). The PVR variants had comparable or somewhat improved binding to PVRL3 relative to parental wild-type PVR. Therefore, in addition to enhancing an immune response (for example to a tumor), the PVR variants may have the ability to localize preferentially to tumors by binding to PVRL3 exposed on tumors by the disruption of normal tight junction architecture and targeting the tumor cells for immunosurveillance.

It is understood that the examples and embodiments described herein are for illustrative purposes only and that various modifications or changes in light thereof will be suggested to person skilled in the art and are to be included within the spirit and purview of this application.

All publications, patents, patent applications, internet sites, and accession numbers/database sequences including both polynucleotide and polypeptide sequences cited herein are hereby incorporated by reference herein in their entirety for all purposes to the same extent as if each individual publication, patent, patent application, internet site, or accession number/database sequence were specifically and individually indicated to be so incorporated by reference.

The sequences disclosed in the application are:

Human PVR with predicted
signal sequence underlined
(SEQ ID NO: 1)
MARAMAAAWPLLLVALLVLSWPPPGTGDVVVQAPTQVPGFLGDSVTLPCY

LQVPNMEVTHVSQLTWARHGESGSMAVFHQTQGPSYSESKRLEFVAARLG

AELRNASLRMFGLRVEDEGNYTCLFVTFPQGSRSVDIWLRVLAKPQNTAE

VQKVQLTGEPVPMARCVSTGGRPPAQITWHSDLGGMPNTSQVPGFLSGTV

TVTSLWILVPSSQVDGKNVTCKVEHESFEKPQLLTVNLTVYYPPEVSISG

YDNNWYLGQNEATLTCDARSNPEPTGYNWSTTMGPLPPFAVAQGAQLLIR

PVDKPINTTLICNVTNALGARQAELTVQVKEGPPSEHSGMSRNAIIFLVL

GILVFLILLGIGIYFYWSKCSREVLWHCHLCPSSTEHASASANGHVSYSA

VSRENSSSQDPQTEGTR

Human PVRL1 with predicted signal
sequence underlined
(SEQ ID NO: 2)
MARMGLAGAAGRWWGLALGLTAFFLPGVHSQVVQVNDSMYGFIGTDVVLH

CSFANPLPSVKITQVTWQKSTNGSKQNVAIYNPSMGVSVLAPYRERVEFL

RPSFTDGTIRLSRLELEDEGVYICEFATFPTGNRESQLNLTVMAKPTNWI

EGTQAVLRAKKGQDDKVLVATCTSANGKPPSVVSWETRLKGEAEYQEIRN

PNGTVTVISRYRLVPSREAHQQSLACIVNYHMDRFKESLTLNVQYEPEVT

IEGFDGNWYLQRMDVKLTCKADANPPATEYHWTTLNGSLPKGVEAQNRTL

FFKGPINYSLAGTYICEATNPIGTRSGQVEVNITEFPYTPSPPEHGRRAG

PVPTAIIGGVAGSILLVLIVVGGIVVALRRRHTFKGDYSTKKHVYGNGY

SKAGIPQHHPPMAQNLQYPDDSDDEKKAGPLGGSSYEEEEEEEGGGGGE

RKVGGPHPKYDEDAKRPYFTVDEAEARQDGYGDRTLGYQYDPEQLDLAEN

MVSQNDGSFISKKEWYV

Human PVRL2 with predicted signal
sequence underlined
(SEQ ID NO: 3)
MARAAALLPSRSPPTPLLWPLLLLLLLETGAQDVRVQVLPEVRGQLGGTV

ELPCHLLPPVPGLYISLVTWQRPDAPANHQNVAAFHPKMGPSFPSPKPGS

ERLSFVSAKQSTGQDTEAELQDATLALHGLTVEDEGNYTCEFATFPKGSV

RGMTWLRVIAKPKNQAEAQKVTFSQDPTTVALCISKEGRPPARISWLSSL

DWEAKETQVSGTLAGTVTVTSRFTLVPSGRADGVTVTCKVEHESFEEPAL

IPVTLSVRYPPEVSISGYDDNWYLGRTDATLSCDVRSNPEPTGYDWSTTS

GTFPTSAVAQGSQLVIHAVDSLFNTTFVCTVTNAVGMGRAEQVIFVRETP

NTAGAGATGGIIGGIIAAIIATAVAATGILICRQQRKEQTLQGAEEDEDL

EGPPSYKPPTPKAKLEAQEMPSQLFTLGASEHSPLKTPYFDAGASCTEQE

MPRYHELPTLEERSGPLHPGATSLGSPIPVPPGPPAVEDVSLDLEDEEGE

EEEEYLDKINPIYDALSYSSPSDSYQGKGFVMSRAMYV

Human PVRL3 with predicted signal
sequence underlined
(SEQ ID NO: 4)
MARTLRPSPLCPGGGKAQLSSASLLGAGLLLQPPTPPPLLLLLFPLLLFS

RLCGALAGPIIVEPHVTAVWGKNVSLKCLIEVNETITQISWEKIHGKSSQ

TVAVHHPQYGFSVQGEYQGRVLFKNYSLNDATITLHNIGFSDSGKYICKA

VTFPLGNAQSSTTVTVLVEPTVSLIKGPDSLIDGGNETVAAICIAATGKP

VAHIDWEGDLGEMESTTTSFPNETATIISQYKLFPTRFARGRRITCVVKH

PALEKDIRYSFILDIQYAPEVSVTGYDGNWFVGRKGVNLKCNADANPPPF

KSVWSRLDGQWPDGLLASDNTLHFVHPLTFNYSGVYICKVTNSLGQRSDQ

KVIYISDPPTTTTLQPTIQWHPSTADIEDLATEPKKLPFPLSTLATIKDD

TIATIIASVVGGALFIVLVSVLAGIFCYRRRRTFRGDYFAKNYIPPSDMQ

KESQIDVLQQDELDSYPDSVKKENKNPVNNLIRKDYLEEPEKTQWNNVEN

LNRFERPMDYYEDLKMGMKFVSDEHYDENEDDLVSHVDGSVISRREWYV

Human PVRL4 with predicted signal
sequence underlined
(SEQ ID NO: 4)
MPLSLGAEMWGPEAWLLLLLLLASFTGRCPAGELETSDVVTVVLGQDAKL

PCFYRGDSGEQVGQVAWARVDAGEGAQELALLHSKYGLHVSPAYEGRVEQ

PPPPRNPLDGSVLLRNAVQADEGEYECRVSTFPAGSFQARLRLRVLVPPL

PSLNPGPALEEGQGLTLAASCTAEGSPAPSVTWDTEVKGTTSSRSFKHSR

SAAVTSEFHLVPSRSMNGQPLTCVVSHPGLLQDQRITHILHVSFLAEASV

RGLEDQNLWHIGREGAMLKCLSEGQPPPSYNWTRLDGPLPSGVRVDGDTL

GFPPLTTEHSGIYVCHVSNEFSSRDSQVTVDVLDPQEDSGKQVDLVSASV

VVVGVIAALLFCLLVVVVVLMSRYHRRKAQQMTQKYEEELTLTRENSIRR

LHSHHTDPRSQPEESVGLRAEGHPDSLKDNSSCSVMSEEPEGRSYSTLTT

VREIETQTELLSPGSGRAEEEEDQDEGIKQAMNHFVQENGTLRAKPTGNG

IYINGRGHLV

Human TIGIT with predicted signal
sequence underlined
(SEQ ID NO: 6)
MRWCLLLIWAQGLRQAPLASGMMTGTIETTGNISAEKGGSIILQCHLSST

TAQVTQVNWEQQDQLLAICNADLGWHISPSFKDRVAPGPGLGLTLQSLTV

NDTGEYFCIYHTYPDGTYTGRIFLEVLESSVAEHGARFQIPLLGAMAATL

VVICTAVIVVVALTRKKKALRIHSVEGDLRRKSAGQEEWSPSAPSPPGSC

VQAEAAPAGLCGEQRGEDCAELHDYFNVLSYRSLGNCSFFTETG

Human CD96 with predicted signal
sequence underlined
(SEQ ID NO: 7)
MEKKWKYCAVYYIIQIHFVKGVWEKTVNTEENVYATLGSDVNLTCQTQTV

GFFVQMQWSKVTNKIDLIAVYHPQYGFYCAYGRPCESLVTFTETPENGSK

WTLHLRNMSCSVSGRYECMLVLYPEGIQTKIYNLLIQTHVTADEWNSNHT

IEIEINQTLEIPCFQNSSSKISSEFTYAWSVENSSTDSWVLLSKGIKEDN

GTQETLISQNHLISNSTLLKDRVKLGTDYRLHLSPVQIFDDGRKFSCHIR

VGPNKILRSSTTVKVFAKPEIPVIVENNSTDVLVERRFTCLLKNVFPKAN

ITWFIDGSFLHDEKEGIYITNEERKGKDGFLELKSVLTRVHSNKPAQSDN

LTIWCMALSPVPGNKVWNISSEKITFLLGSEISSTDPPLSVTESTLDTQP

SPASSVSPARYPATSSVTLVDVSALRPNTTPQPSNSSMTTRGFNYPWTSS

GTDTKKSVSRIPSETYSSSPSGAGSTLHDNVFTSTARAFSEVPTTANGST

KTNHVHITGIVVNKPKDGMSWPVIVAALLFCCMILFGLGVRKWCQYQKEI

MERPPPFKPPPPPIKYTCIQEPNESDLPYHEMETL

Human CD226 with predicted signal
sequence underlined
(SEQ ID NO: 8)
MDYPTLLLALLHVYRALCEEVLWHTSVPFAENMSLECVYPSMGILTQVEW

FKIGTQQDSIAIFSPTHGMVIRKPYAERVYFLNSTMASNNMTLFFRNASE

DDVGYYSCSLYTYPQGTWQKVIQVVQSDSFEAAVPSNSHIVSEPGKNVTL

TCQPQMTWPVQAVRWEKIQPRQIDLLTYCNLVHGRNFTSKFPRQIVSNCS

HGRWSVIVIPDVTVSDSGLYRCYLQASAGENETFVMRLTVAEGKTDNQYT

LFVAGGTVLLLLFVISITTIIVIFLNRRRRRERRDLFTESWDTQKAPNNY

RSPISTSQPTNQSMDDTREDIYVNYPTFSRRPKTRV

PVR Family
Human PVR - ECD without predicted
signal sequence
(SEQ ID NO: 9)
DVVVQAPTQVPGFLGDSVTLPCYLQVPNMEVTHVSQLTWARHGESGSMAV

FHQTQGPSYSESKRLEFVAARLGAELRNASLRMFGLRVEDEGNYTCLFVT

FPQGSRSVDIWLRVLAKPQNTAEVQKVQLTGEPVPMARCVSTGGRPPAQI

TWHSDLGGMPNTSQVPGFLSGTVTVTSLWILVPSSQVDGKNVTCKVEHES

FEKPQLLTVNLTVYYPPEVSISGYDNNWYLGQNEATLTCDARSNPEPTGY

NWSTTMGPLPPFAVAQGAQLLIRPVDKPINTTLICNVTNALGARQAELTV

QVKEGPPSEHSGMSRN

Human PVRL1 - ECD without predicted
signal sequenc
(SEQ ID NO: 10)
QVVQVNDSMYGFIGTDVVLHCSFANPLPSVKITQVTWQKSTNGSKQNVAI

YNPSMGVSVLAPYRERVEFLRPSFTDGTIRLSRLELEDEGVYICEFATFP

TGNRESQLNLTVMAKPTNWIEGTQAVLRAKKGQDDKVLVATCTSANGKPP

SVVSWETRLKGEAEYQEIRNPNGTVTVISRYRLVPSREAHQQSLACIVNY

HMDRFKESLTLNVQYEPEVTIEGFDGNWYLQRMDVKLTCKADANPPATEY

HWTTLNGSLPKGVEAQNRTLFFKGPINYSLAGTYICEATNPIGTRSGQVE

VNITEFPYTPSPPEHGRRAGPVPTA

Human PVRL2 - ECD without predicted
signal sequence
(SEQ ID NO: 11)
QDVRVQVLPEVRGQLGGTVELPCHLLPPVPGLYISLVTWQRPDAPANHQN

VAAFHPKMGPSFPSPKPGSERLSFVSAKQSTGQDTEAELQDATLALHGLT

VEDEGNYTCEFATFPKGSVRGMTWLRVIAKPKNQAEAQKVTFSQDPTTVA

LCISKEGRPPARISWLSSLDWEAKETQVSGTLAGTVTVTSRFTLVPSGRA

DGVTVTCKVEHESFEEPALIPVTLSVRYPPEVSISGYDDNWYLGRTDATL

SCDVRSNPEPTGYDWSTTSGTFPTSAVAQGSQLVIHAVDSLFNTTFVCTV

TNAVGMGRAEQVIFVRETPNTAGAGATGG

Human PVRL3 - ECD without predicted
signal sequence
(SEQ ID NO: 12)
GPIIVEPHVTAVWGKNVSLKCLIEVNETITQISWEKIHGKSSQTVAVHHP

QYGFSVQGEYQGRVLFKNYSLNDATITLHNIGFSDSGKYICKAVTFPLGN

AQSSTTVTVLVEPTVSLIKGPDSLIDGGNETVAAICIAATGKPVAHIDWE

GDLGEMESTTTSFPNETATIISQYKLFPTRFARGRRITCVVKHPALEKDI

RYSFILDIQYAPEVSVTGYDGNWFVGRKGVNLKCNADANPPPFKSVWSRL

DGQWPDGLLASDNTLHFVHPLTFNYSGVYICKVTNSLGQRSDQKVIYISD

PPTTTTLQPTIQWHPSTADIEDLATEPKKLPFPLSTLATIKDDTIAT

Human PVRL4 - ECD without predicted
signal sequence
(SEQ ID NO: 13)
GELETSDVVTVVLGQDAKLPCFYRGDSGEQVGQVAWARVDAGEGAQELAL

LHSKYGLHVSPAYEGRVEQPPPPRNPLDGSVLLRNAVQADEGEYECRVST

FPAGSFQARLRLRVLPPLPSLNPGPALEEGQGLTLAASCTAEGSPAPSV

TWDTEVKGTTSSRSFKHSRSAAVTSEFHLVPSRSMNGQPLTCVVSHPGLL

QDQRITHILHVSFLAEASVRGLEDQNLWHIGREGAMLKCLSEGQPPPSYN

WTRLDGPLPSGVRVDGDTLGFPPLTTEHSGIYVCHVSNEFSSRDSQVTVD

VLDPQEDSGKQVDLVSAS

Human TIGIT - ECD without predicted
signal sequence
(SEQ ID NO: 14)
MMTGTIETTGNISAEKGGSIILQCHLSSTTAQVTQVNWEQQDQLLAICNA

DLGWHISPSFKDRVAPGPGLGLTLQSLTVNDTGEYFCIYHTYPDGTYTGR

IFLEVLESSVAEHGARFQIPLLGAMAATLVVICTAVIVVVA

Human CD96 - ECD without predicted
signal sequence
(SEQ ID NO: 15)
KTVNTEENVYATLGSDVNLTCQTQTVGFFVQMQWSKVTNKIDLIAVYHPQ

YGFYCAYGRPCESLVTFTETEPENGSKWTLHLRNMSCSVSGRYECMLVLYP

EGIQTKIYNLLIQTHVTADEWNSNHTIEIEINQTLEIPCFQNSSSKISSE

FTYAWSVENSSTDSWVLLSKGIKEDNGTQETLISQNHLISNSTLLKDRVK

LGTDYRLHLSPVQIFDDGRKFSCHIRVGPNKILRSSTTVKVFAKPEIPVI

VENNSTDVLVERRFTCLLKNVFPKANITWFIDGSFLHDEKEGIYITNEER

KGKDGFLELKSVLTRVHSNKPAQSDNLTIWCMALSPVPGNKVWNISSEKI

TFLLGSEISSTDPPLSVTESTLDTQPSPASSVSPARYPATSSVTLVDVSA

LRPNTTPQPSNSSMTTRGFNYPWTSSGTDTKKSVSRIPSETYSSSPSGAG

STLHDNVFTSTARAFSEVPTTANGSTKTNHVHITGIVVNKPKDGMS

Human CD226 - ECD without predicted
signal sequence
(SEQ ID NO: 16)
EEVLWHTSVPFAENMSLECVYPSMGILTQVEWFKIGTQQDSIAIFSPTHG

MVIRKPYAERVYFLNSTMASNNMTLFFRNASEDDVGYYSCSLYTYPQGTW

QKVIQVVQSDSFEAAVPSNSHIVSEPGKNVTLTCQPQMTWPVQAVRWEKI

QPRQIDLLTYCNLVHGRNFTSKFPRQIVSNCSHGRWSVIVIPDVTVSDSG

LYRCYLQASAGENETFVMRLTVAEGKTDNQYTLFVA

Human PVR - N-terminal IgV domain
(SEQ ID NO: 17)
DVVVQAPTQVPGFLGDSVTLPCYLQVPNMEVTHVSQLTWARHGESGSMAV

FHQTQGPSYSESKRLEFVAARLGAELRNASLRMFGLRVEDEGNYTCLFVT

FPQGSRSVDIWLRVLA

Variant 1 Human PVR - N-terminal IgV domain
(SEQ ID NO: 18)
DVVVQAPTQVPGFLGDSVTLPCYLQVPNMEVTHVSQLXWXRHGEXXXMAV

FHQXXGXXYSESKRLEFVAARLGAELRNASLRMFGLRVEDEGNYTCLFVT

FPQGSRSVDIWL

X = any amino acid
Variant 2 Human PVR - N-terminal IgV domain
(SEQ ID NO: 19)
DVVVQAPTQVPGFLGDSVTLPCYLQVPNMEVTHVSQLTWARHGENGSMAV

FHQTQGPSYSESKRLEFVAARLGAELRNASLRMFGLRVEDEGNYTCLFVT

FPQGSRSVDIWL

Variant 3 Human PVR - N-terminal IgV domain
(SEQ ID NO: 20)
DVVVQAPTQVPGFLGDSVTLPCYLQVPNMEVTHVSQLTWARHGESGSMAV
FHQTKGPSYSESKRLEFVAARLGAELRNASLRMFGLRVEDEGNYTCLFVT
FPQGSRSVDIWL Variant 4 Human PVR - N-terminal IgV domain
(SEQ ID NO: 21)
DVVVQAPTQVPGFLGDSVTLPCYLQVPNMEVTHVSQLTWARHGENGSMAV
FHQTKGPSYSESKRLEFVAARLGAELRNASLRMFGLRVEDEGNYTCLFVT
FPQGSRSVDIWL Human PVRL1 - N-terminal IgV domain
(SEQ ID NO: 22)
QVVQVNDSMYGFIGTDVVLHCSFANPLPSVKITQVTWQKSTNGSKQNVAI
YNPSMGVSVLAPYRERVEFLRPSFTDGTIRLSRLELEDEGVYICEFATFP
TGNRESQLNLTVMA Human PVRL2 - N-terminal IgV domain
(SEQ ID NO: 23)
DVRVQVLPEVRGQLGGTVELPCHLLPPVPGLYISLVTWQRPDAPANHQNV
AAFHPKMGPSFPSPKPGSERLSFVSAKQSTGQDTEAELQDATLALHGLTV
EDEGNYTCEFATFPKGSVRG
MTWLRVIA Human PVRL3 - N-terminal IgV domain
(SEQ ID NO: 24)
GPIIVEPHVTAVWGKNVSLKCLIEVNETITQISWEKIHGKSSQTVAVHHP
QYGFSVQGEYQGRVLFKNYSLNDATITLHNIGFSDSGKYICKAVTFPLGN
AQSSTTVTVLV Human PVRL4 - N-terminal IgV domain
(SEQ ID NO: 25)
GELETSDVVTVVLGQDAKLPCFYRGDSGEQVGQVAWARVDAGEGAQELAL
LHSKYGLHVSPAYEGRVEQPPPPRNPLDGSVLLRNAVQADEGEYECRVST
FPAGSFQARLRLRVLVPPLP Human IgG$_1$ Fc region
(SEQ ID NO: 26)
DKTHTCPPCPAPELLGGPSVFLFPPKPKDTLMISRTPEVTCVVVDVSHED
PEVKFNWYVDGVEVHNAKTKPREEQYNSTYRVVSVLTVLHQDWLNGKEYK
CKVSNKALPAPIEKTISKAKGQPREPQVYTLPPSRDELTKNQVSLTCLVK
GFYPSDIAVEWESNGQPENNYKTTPPVLDSDGSFFLYSKLTVDKSRWQQG
NVFSCSVMHEALHNHYTQKSLSLSPGK Human IgG$_1$ Fc region
(SEQ ID NO: 27)
KSSDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSLTC
LVKGFYPSDIAVEWESNGQPENNYKTTPPVLDSDGSFFLYSKLTVDKSRW
QQGNVFSCSVMHEALHNHYTQKSLSLSPGK Human IgG$_1$ Fc region
(SEQ ID NO: 28)
EPKSSDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLN
GKEYKCKVSNKALPAPIEKTISKAKGQPREPQVYTLPPSRDELTKNQVSL
TCLVKGFYPSDIAVEWESNGQPENNYKTTPPVLDSDGSFFLYSKLTVDKS
RWQQGNVFSCSVMHEALHNHYTQKSLSLSPGK Human IgG2 Fc region
(SEQ ID NO: 29)
CVECPPCPAPPVAGPSVFLFPPKPKDTLMISRTPEVTCVVVDVSHEDPEV
QFNWYVDGVEVHNAKTKPREEQFNSTFRVVSVLTVVHQDWLNGKEYKCKV
SNKGLPAPIEKTISKTKGQPREPQVYTLPPSREEMTKNQVSLTCLVKGFY
PSDIAVEWESNGQPENNYKTTPPMLDSDGSFFLYSKLTVDKSRWQQGNVF
SCSVMHEALHNHYTQKSLSLSPGK Human IgG2 Fc region (13B chain)
(SEQ ID NO: 30)
CVECPPCPAPPVAGPSVFLFPPKPKDTLMISRTPEVTCVVVDVSHEDPEV
QFNWYVDGVEVHNAKTKPREEQFNSTFRVVSVLTVVHQDWLNGKEYKCKV
SNKGLPAPIEKTISKTKGQPREPQVYTLPPSREEMTKNQVSLTCLVEGFY
PSDIAVEWESNGQPENNYKTTPPMLDSDGSFFLYSELTVDKSRWQQGNVF
SCSVMHEALHNHYTQKSLSLSPGK Human IgG2 Fc region (13A chain)
(SEQ ID NO: 31)
CVECPPCPAPPVAGPSVFLFPPKPKDTLMISRTPEVTCVVVDVSHEDPEV
QFNWYVDGVEVHNAKTKPREEQFNSTFRVVSVLTVVHQDWLNGKEYKCKV
SNKGLPAPIEKTISKTKGQPREPQVYTLPPSREKMTKNQVSLTCLVKGFY
PSDIAVEWESNGQPENNYKTTPPMLKSDGSFFLYSKLTVDKSRWQQGNVF
SCSVMHEALHNHYTQKSLSLSPGK FLAG Tag
(SEQ ID NO: 32)
DYKDDDDK Linker
(SEQ ID NO: 33)
ESGGGGVT Linker
(SEQ ID NO: 34)
LESGGGGVT Linker
(SEQ ID NO: 35)
GRAQVT Linker
(SEQ ID NO: 36)
WRAQVT Linker
(SEQ ID NO: 37)
ARGRAQVT Variant human PVRL2 - N-terminal IgV domain
(SEQ ID NO: 38)
DVRVQVLPEVRGQLGGTVELPCHLLPPVPGLYISLVXWXRPDAPANXXXV
AAFHPXXGXXFPSPKPGSERLSFVSAKQSTGQDTEAELQDATLALHGLTV
EDEGNYTCEFATFPKGSVRG
MTWLRVIA
X = any amino acid Human IgG1 Heavy chain constant region
(SEQ ID NO: 39)
ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEP
KSCDKTHTCPPCPAPELLGGPSVFLFPPKPKDTLMISRTPEVTCVVVDVS HEDPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSLTC
LVKGFYPSDIAVEWESNGQPENNYKTTPPVLDSDGSFFLYSKLTVDKSRW
QQGNVFSCSVMHEALHNHYTQKSLSLSPGK Human IgG2 Heavy chain constant region
(SEQ ID NO: 40)
ASTKGPSVFPLAPCSRSTSESTAALGCLVKDYFPEPVTVSWNSGALTSGV
HTFPAVLQSSGLYSLSSVVTVPSSNFGTQTYTCNVDHKPSNTKVDKTVER
KCCVECPPCPAPPVAGPSVFLFPPKPKDTLMISRTPEVTCVVVDVSHEDP
EVQFNWYVDGVEVHNAKTKPREEQFNSTFRVVSVLTVVHQDWLNGKEYKC
KVSNKGLPAPIEKTISKTKGQPREPQVYTLPPSREEMTKNQVSLTCLVKG
FYPSDIAVEWESNGQPENNYKTTPPMLDSDGSFFLYSKLTVDKSRWQQGN
VFSCSVMHEALHNHYTQKSLSLSPGK Human IgG3 Heavy chain constant region
(SEQ ID NO: 41)
ASTKGPSVFPLAPCSRSTSGGTAALGCLVKDYFPEPVTVSWNSGALTSGV
HTFPAVLQSSGLYSLSSVVTVPSSSLGTQTYTCNVNHKPSNTKVDKRVEL
KTPLGDTTHTCPRCPEPKSCDTPPPCPRCPEPKSCDTPPPCPRCPEPKSC
DTPPPCPRCPAPELLGGPSVFLFPPKPKDTLMISRTPEVTCVVVDVSHED
PEVQFKWYVDGVEVHNAKTKPREEQYNSTFRVVSVLTVLHQDWLNGKEYK
CKVSNKALPAPIEKTISKTKGQPREPQVYTLPPSREEMTKNQVSLTCLVK
GFYPSDIAVEWESSGQPENNYNTTPPMLDSDGSFFLYSKLTVDKSRWQQG
NIFSCSVMHEALHNRFTQKSLSLSPGK Human IgG4 Heavy chain constant region
(SEQ ID NO: 42)
ASTKGPSVFPLAPCSRSTSESTAALGCLVKDYFPEPVTVSWNSGALTSGV
HTFPAVLQSSGLYSLSSVVTVPSSSLGTKTYTCNVDHKPSNTKVDKRVES
KYGPPCPSCPAPEFLGGPSVFLFPPKPKDTLMISRTPEVTCVVVDVSQED
PEVQFNWYVDGVEVHNAKTKPREEQFNSTYRVVSVLTVLHQDWLNGKEYK
CKVSNKGLPSSIEKTISKAKGQPREPQVYTLPPSQEEMTKNQVSLTCLVK
GFYPSDIAVEWESNGQPENNYKTTPPVLDSDGSFFLYSRLTVDKSRWQEG
NVFSCSVMHEALHNHYTQKSLSLSLGK Human IgG2 Fc region
(SEQ ID NO: 43)
TKVDKTVERKCCVECPPCPAPPVAGPSVFLFPPKPKDTLMISRTPEVTCV
VVDVSHEDPEVQFNWYVDGVEVHNAKTKPREEQFNSTFRVVSVLTVVHQD
WLNGKEYKCKVSNKGLPAPIEKTISKTKGQPREPQVYTLPPSREEMTKNQ
VSLTCLVKGFYPSDIAVEWESNGQPENNYKTTPPMLDSDGSFFLYSKLTV
DKSRWQQGNVFSCSVMHEALHNHYTQKSLSLSPGK Human IgG2 Fc region variant
(SEQ ID NO: 44)
TKVDKTVERKSCVECPPCPAPPVAGPSVFLFPPKPKDTLMISRTPEVTCV
VVDVSHEDPEVQFNWYVDGVEVHNAKTKPREEQFNSTFRVVSVLTVVHQD
WLNGKEYKCKVSNKGLPAPIEKTISKTKGQPREPQVYTLPPSREEMTKNQ
VSLTCLVKGFYPSDIAVEWESNGQPENNYKTTPPMLDSDGSFFLYSKLTV
DKSRWQQGNVFSCSVMHEALHNHYTQKSLSLSPGK Human IgG2 Fc region (Variant 13A)
(SEQ ID NO: 45)
TKVDKTVERKCCVECPPCPAPPVAGPSVFLFPPKPKDTLMISRTPEVTCV
VVDVSHEDPEVQFNWYVDGVEVHNAKTKPREEQFNSTFRVVSVLTVVHQD
WLNGKEYKCKVSNKGLPAPIEKTISKTKGQPREPQVYTLPPSREKMTKNQ
VSLTCLVKGFYPSDIAVEWESNGQPENNYKTTPPMLKSDGSFFLYSKLTV
DKSRWQQGNVFSCSVMHEALHNHYTQKSLSLSPGK Human IgG2 Fc region variant (Variant 13A)
(SEQ ID NO: 46)
TKVDKTVERKSCVECPPCPAPPVAGPSVFLFPPKPKDTLMISRTPEVTCV
VVDVSHEDPEVQFNWYVDGVEVHNAKTKPREEQFNSTFRVVSVLTVVHQD
WLNGKEYKCKVSNKGLPAPIEKTISKTKGQPREPQVYTLPPSREKMTKNQ
VSLTCLVKGFYPSDIAVEWESNGQPENNYKTTPPMLKSDGSFFLYSKLTV
DKSRWQQGNVFSCSVMHEALHNHYTQKSLSLSPGK Human IgG2 Fc region (Variant 13B)
(SEQ ID NO: 47)
TKVDKTVERKCCVECPPCPAPPVAGPSVFLFPPKPKDTLMISRTPEVTCV
VVDVSHEDPEVQFNWYVDGVEVHNAKTKPREEQFNSTFRVVSVLTVVHQD
WLNGKEYKCKVSNKGLPAPIEKTISKTKGQPREPQVYTLPPSREEMTKNQ
VSLTCLVEGFYPSDIAVEWESNGQPENNYKTTPPMLDSDGSFFLYSELTV
DKSRWQQGNVFSCSVMHEALHNHYTQKSLSLSPGK Human IgG2 Fc region variant (Variant 13B)
(SEQ ID NO: 48)
TKVDKTVERKSCVECPPCPAPPVAGPSVFLFPPKPKDTLMISRTPEVTCV
VVDVSHEDPEVQFNWYVDGVEVHNAKTKPREEQFNSTFRVVSVLTVVHQD
WLNGKEYKCKVSNKGLPAPIEKTISKTKGQPREPQVYTLPPSREEMTKNQ
VSLTCLVEGFYPSDIAVEWESNGQPENNYKTTPPMLDSDGSFFLYSELTV
DKSRWQQGNVFSCSVMHEALHNHYTQKSLSLSPGK

---

What is claimed is:

1. A method of activating or increasing an immune response in a subject comprising, administering to the subject a therapeutically effective amount of a polypeptide comprising a poliovirus receptor (PVR) variant, wherein the PVR variant comprises the amino acid sequence of wild-type PVR (SEQ ID NO:1), except for one or more amino acid substitutions of amino acid residues selected from the group consisting of 65, 67, 72, 73, 74, 81, 82, 84, and 85 of wild-type PVR (SEQ ID NO:1), and wherein the PVR variant specifically binds the extracellular domain of human TIGIT and does not bind the extracellular domain of human CD226.

2. The method of claim 1, wherein the PVR variant also binds the extracellular domain of human CD96.

3. The method of claim 1, wherein the one or more amino acid substitutions within the PVR variant comprise substitutions in one or more amino acids:

(a) corresponding to amino acid 72 of wild-type PVR (SEQ ID NO:1);

(b) corresponding to amino acid 82 of wild-type PVR (SEQ ID NO 1); or (c) corresponding to amino acid 72 and amino acid 82 of wild-type PVR (SEQ ID NO:1).

4. The method of claim 1, wherein the PVR variant comprises an amino acid sequence selected from the group consisting of: SEQ ID NO:18, SEQ ID NO:19, SEQ ID NO:20, and SEQ ID NO:21.

5. The method of claim 1, wherein the polypeptide is a soluble receptor.

6. The method of claim 1, wherein the PVR variant is linked to a non-PVR polypeptide.

7. The method of claim 6, wherein the non-PVR polypeptide comprises a human Fc region.

8. The method of claim 1, wherein the polypeptide comprising a PVR variant:

(a) increases cell-mediated immunity;

(b) increases T-cell activity;

(c) increases cytolytic (CTL) activity;

(d) increases natural killer (NK) cell activity;

(e) is an antagonist of TIGIT-mediated signaling;

(f) is an antagonist of CD96-mediated signaling;

(g) inhibits TIGIT signaling;

(h) inhibits CD96 signaling;

(i) increases CD226 signaling;

(j) inhibits or blocks the interaction between PVR and TIGIT;

(k) inhibits or blocks the interaction between PVR and TIGIT and the interaction between PVR and CD96;

(l) does not inhibit the interaction between PVR and CD226;

(m) inhibits or blocks the interaction between PVR and TIGIT and the interaction between PVR and CD96, and does not inhibit, the interaction between PVR and CD226; and/or (n) inhibits or blocks the interaction between PVRL2 and TIGIT, the interaction, between PVRL3 and TIGIT, and/or the interaction between PVRL4 and TIGIT.

9. The method of claim 1, wherein the immune response is directed to a tumor cell or cancer.

10. The method of claim 1, further comprising the administration of at least one additional therapeutic agent.

11. The method of claim 10, wherein the additional therapeutic agent is an immune response stimulating agent, a chemotherapeutic agent, a small molecule agent, and/or an antibody.

12. The method of claim 11, wherein the additional therapeutic agent is an immune response stimulating agent comprising an antibody that block immunosuppressive functions.

13. A method of inhibiting tumor growth in a subject comprising: administering to the subject a therapeutically effective amount of a polypeptide comprising a poliovirus receptor (PVR) variant, wherein the PVR variant comprises the amino acid sequence of wild-type PVR (SEQ ID NO:1), except for one or more amino acid substitutions of amino acid residues selected from the group consisting of 65, 67, 72, 73, 74, 81, 82, 84, and 85 of wild-type PVR (SEQ ID NO:1), and wherein the PVR variant specifically binds the extracellular domain of human TIGIT and does not bind the extracellular domain of human CD226.

14. The method of claim 13, wherein the tumor is selected from the group consisting of: colorectal tumor, pancreatic tumor, lung tumor, ovarian tumor, liver tumor, breast tumor, kidney tumor, prostate tumor, neuroendocrine tumor, gastrointestinal tumor, melanoma, cervical tumor, bladder tumor, glioblastoma, and head and neck tumor.

15. A method of treating cancer in a subject comprising: administering to the subject a therapeutically effective amount of a polypeptide comprising a poliovirus receptor (PVR) variant, wherein the PVR variant comprises the amino acid sequence of wild-type PVR (SEQ ID NO:1), except for one or more amino acid substitutions of amino acid residues selected from the group consisting of 65, 67, 72, 73, 74, 81, 82, 84, and 85 of wild-type PVR (SEQ ID NO:1), and wherein the PVR variant specifically binds the extracellular domain of human TIGIT and does not bind the extracellular domain of human CD226.

16. The method of claim 15, wherein the cancer is selected from the group consisting of colorectal cancer, ovarian cancer, pancreatic cancer, lung cancer, liver cancer, breast cancer, kidney cancer, prostate cancer, gastrointestinal cancer, melanoma, cervical cancer, bladder cancer, glioblastoma, and head and neck cancer.

17. The method of claim 15, wherein the cancer a hematologic cancer.

18. The method of claim 17, wherein the hematologic cancer is selected from the group consisting of: acute myelogenous leukemia (AML), Hodgkin lymphoma, multiple myeloma, T-cell acute lymphoblastic leukemia (T-ALL), chronic lymphocytic leukemia (CLL), hairy cell leukemia, chronic myelogenous leukemia (CML), non-Hodgkin lymphoma, diffuse large B-cell lymphoma (DLBCL), mantle cell lymphoma (MCL), and cutaneous T-cell lymphoma (CTCL).

* * * * *

SEQUENCE LISTING

<160> NUMBER OF SEQ ID NOS: 62

<210> SEQ ID NO 1
<211> LENGTH: 417
<212> TYPE: PRT
<213> ORGANISM: Homo sapiens

```
<400> SEQUENCE: 1

Met Ala Arg Ala Met Ala Ala Trp Pro Leu Leu Leu Val Ala Leu
1               5                   10                  15

Leu Val Leu Ser Trp Pro Pro Gly Thr Gly Asp Val Val Gln
                20              25                  30

Ala Pro Thr Gln Val Pro Gly Phe Leu Gly Asp Ser Val Thr Leu Pro
            35                  40                  45

Cys Tyr Leu Gln Val Pro Asn Met Glu Val Thr His Val Ser Gln Leu
        50                  55                  60

Thr Trp Ala Arg His Gly Glu Ser Gly Ser Met Ala Val Phe His Gln
65                  70                  75                  80

Thr Gln Gly Pro Ser Tyr Ser Glu Ser Lys Arg Leu Glu Phe Val Ala
                    85                  90                  95

Ala Arg Leu Gly Ala Glu Leu Arg Asn Ala Ser Leu Arg Met Phe Gly
                100                 105                 110

Leu Arg Val Glu Asp Glu Gly Asn Tyr Thr Cys Leu Phe Val Thr Phe
            115                 120                 125

Pro Gln Gly Ser Arg Ser Val Asp Ile Trp Leu Arg Val Leu Ala Lys
        130                 135                 140

Pro Gln Asn Thr Ala Glu Val Gln Lys Val Gln Leu Thr Gly Glu Pro
145                 150                 155                 160

Val Pro Met Ala Arg Cys Val Ser Thr Gly Gly Arg Pro Pro Ala Gln
                    165                 170                 175

Ile Thr Trp His Ser Asp Leu Gly Gly Met Pro Asn Thr Ser Gln Val
                180                 185                 190

Pro Gly Phe Leu Ser Gly Thr Val Thr Val Thr Ser Leu Trp Ile Leu
            195                 200                 205

Val Pro Ser Ser Gln Val Asp Gly Lys Asn Val Thr Cys Lys Val Glu
        210                 215                 220

His Glu Ser Phe Glu Lys Pro Gln Leu Leu Thr Val Asn Leu Thr Val
225                 230                 235                 240

Tyr Tyr Pro Pro Glu Val Ser Ile Ser Gly Tyr Asp Asn Asn Trp Tyr
                    245                 250                 255

Leu Gly Gln Asn Glu Ala Thr Leu Thr Cys Asp Ala Arg Ser Asn Pro
                260                 265                 270

Glu Pro Thr Gly Tyr Asn Trp Ser Thr Thr Met Gly Pro Leu Pro Pro
            275                 280                 285

Phe Ala Val Ala Gln Gly Ala Gln Leu Leu Ile Arg Pro Val Asp Lys
        290                 295                 300

Pro Ile Asn Thr Thr Leu Ile Cys Asn Val Thr Asn Ala Leu Gly Ala
305                 310                 315                 320

Arg Gln Ala Glu Leu Thr Val Gln Val Lys Glu Gly Pro Pro Ser Glu
                    325                 330                 335

His Ser Gly Met Ser Arg Asn Ala Ile Ile Phe Leu Val Leu Gly Ile
                340                 345                 350

Leu Val Phe Leu Ile Leu Leu Gly Ile Gly Ile Tyr Phe Tyr Trp Ser
            355                 360                 365

Lys Cys Ser Arg Glu Val Leu Trp His Cys His Leu Cys Pro Ser Ser
        370                 375                 380

Thr Glu His Ala Ser Ala Ser Ala Asn Gly His Val Ser Tyr Ser Ala
385                 390                 395                 400

Val Ser Arg Glu Asn Ser Ser Ser Gln Asp Pro Gln Thr Glu Gly Thr
                    405                 410                 415
```

Arg

<210> SEQ ID NO 2
<211> LENGTH: 517
<212> TYPE: PRT
<213> ORGANISM: Homo sapiens

<400> SEQUENCE: 2

```
Met Ala Arg Met Gly Leu Ala Gly Ala Ala Gly Arg Trp Trp Gly Leu
1               5                   10                  15

Ala Leu Gly Leu Thr Ala Phe Phe Leu Pro Gly Val His Ser Gln Val
            20                  25                  30

Val Gln Val Asn Asp Ser Met Tyr Gly Phe Ile Gly Thr Asp Val Val
        35                  40                  45

Leu His Cys Ser Phe Ala Asn Pro Leu Pro Ser Val Lys Ile Thr Gln
50                  55                  60

Val Thr Trp Gln Lys Ser Thr Asn Gly Ser Lys Gln Asn Val Ala Ile
65                  70                  75                  80

Tyr Asn Pro Ser Met Gly Val Ser Val Leu Ala Pro Tyr Arg Glu Arg
                85                  90                  95

Val Glu Phe Leu Arg Pro Ser Phe Thr Asp Gly Thr Ile Arg Leu Ser
            100                 105                 110

Arg Leu Glu Leu Glu Asp Glu Gly Val Tyr Ile Cys Glu Phe Ala Thr
        115                 120                 125

Phe Pro Thr Gly Asn Arg Glu Ser Gln Leu Asn Leu Thr Val Met Ala
130                 135                 140

Lys Pro Thr Asn Trp Ile Glu Gly Thr Gln Ala Val Leu Arg Ala Lys
145                 150                 155                 160

Lys Gly Gln Asp Asp Lys Val Leu Val Ala Thr Cys Thr Ser Ala Asn
                165                 170                 175

Gly Lys Pro Pro Ser Val Val Ser Trp Glu Thr Arg Leu Lys Gly Glu
            180                 185                 190

Ala Glu Tyr Gln Glu Ile Arg Asn Pro Asn Gly Thr Val Thr Val Ile
        195                 200                 205

Ser Arg Tyr Arg Leu Val Pro Ser Arg Glu Ala His Gln Gln Ser Leu
210                 215                 220

Ala Cys Ile Val Asn Tyr His Met Asp Arg Phe Lys Glu Ser Leu Thr
225                 230                 235                 240

Leu Asn Val Gln Tyr Glu Pro Glu Val Thr Ile Glu Gly Phe Asp Gly
                245                 250                 255

Asn Trp Tyr Leu Gln Arg Met Asp Val Lys Leu Thr Cys Lys Ala Asp
            260                 265                 270

Ala Asn Pro Pro Ala Thr Glu Tyr His Trp Thr Thr Leu Asn Gly Ser
        275                 280                 285

Leu Pro Lys Gly Val Glu Ala Gln Asn Arg Thr Leu Phe Phe Lys Gly
290                 295                 300

Pro Ile Asn Tyr Ser Leu Ala Gly Thr Tyr Ile Cys Glu Ala Thr Asn
305                 310                 315                 320

Pro Ile Gly Thr Arg Ser Gly Gln Val Glu Val Asn Ile Thr Glu Phe
                325                 330                 335

Pro Tyr Thr Pro Ser Pro Pro Glu His Gly Arg Arg Ala Gly Pro Val
            340                 345                 350

Pro Thr Ala Ile Ile Gly Gly Val Ala Gly Ser Ile Leu Leu Val Leu
        355                 360                 365
```

```
Ile Val Val Gly Gly Ile Val Ala Leu Arg Arg Arg His Thr
    370             375             380

Phe Lys Gly Asp Tyr Ser Thr Lys Lys His Val Tyr Gly Asn Gly Tyr
385             390             395             400

Ser Lys Ala Gly Ile Pro Gln His His Pro Pro Met Ala Gln Asn Leu
                405             410             415

Gln Tyr Pro Asp Asp Ser Asp Asp Glu Lys Lys Ala Gly Pro Leu Gly
            420             425             430

Gly Ser Ser Tyr Glu Glu Glu Glu Glu Glu Gly Gly Gly Gly
        435             440             445

Gly Glu Arg Lys Val Gly Pro His Pro Lys Tyr Asp Glu Asp Ala
    450             455             460

Lys Arg Pro Tyr Phe Thr Val Asp Glu Ala Glu Ala Arg Gln Asp Gly
465             470             475             480

Tyr Gly Asp Arg Thr Leu Gly Tyr Gln Tyr Asp Pro Glu Gln Leu Asp
            485             490             495

Leu Ala Glu Asn Met Val Ser Gln Asn Asp Gly Ser Phe Ile Ser Lys
                500             505             510

Lys Glu Trp Tyr Val
            515

<210> SEQ ID NO 3
<211> LENGTH: 538
<212> TYPE: PRT
<213> ORGANISM: Homo sapiens

<400> SEQUENCE: 3

Met Ala Arg Ala Ala Ala Leu Leu Pro Ser Arg Ser Pro Pro Thr Pro
1               5                   10                  15

Leu Leu Trp Pro Leu Leu Leu Leu Leu Leu Glu Thr Gly Ala Gln
            20                  25                  30

Asp Val Arg Val Gln Val Leu Pro Glu Val Arg Gly Gln Leu Gly Gly
            35                  40                  45

Thr Val Glu Leu Pro Cys His Leu Leu Pro Pro Val Pro Gly Leu Tyr
    50                  55                  60

Ile Ser Leu Val Thr Trp Gln Arg Pro Asp Ala Pro Ala Asn His Gln
65                  70                  75                  80

Asn Val Ala Ala Phe His Pro Lys Met Gly Pro Ser Phe Pro Ser Pro
                85                  90                  95

Lys Pro Gly Ser Glu Arg Leu Ser Phe Val Ser Ala Lys Gln Ser Thr
            100                 105                 110

Gly Gln Asp Thr Glu Ala Glu Leu Gln Asp Ala Thr Leu Ala Leu His
            115                 120                 125

Gly Leu Thr Val Glu Asp Glu Gly Asn Tyr Thr Cys Glu Phe Ala Thr
    130                 135                 140

Phe Pro Lys Gly Ser Val Arg Gly Met Thr Trp Leu Arg Val Ile Ala
145                 150                 155                 160

Lys Pro Lys Asn Gln Ala Glu Ala Gln Lys Val Thr Phe Ser Gln Asp
                165                 170                 175

Pro Thr Thr Val Ala Leu Cys Ile Ser Lys Glu Gly Arg Pro Pro Ala
            180                 185                 190

Arg Ile Ser Trp Leu Ser Ser Leu Asp Trp Glu Ala Lys Glu Thr Gln
        195                 200                 205

Val Ser Gly Thr Leu Ala Gly Thr Val Thr Val Thr Ser Arg Phe Thr
```

```
Leu Val Pro Ser Gly Arg Ala Asp Gly Val Thr Val Thr Cys Lys Val
225                 230                 235                 240

Glu His Glu Ser Phe Glu Pro Ala Leu Ile Pro Val Thr Leu Ser
                245                 250                 255

Val Arg Tyr Pro Pro Glu Val Ser Ile Ser Gly Tyr Asp Asp Asn Trp
            260                 265                 270

Tyr Leu Gly Arg Thr Asp Ala Thr Leu Ser Cys Asp Val Arg Ser Asn
            275                 280                 285

Pro Glu Pro Thr Gly Tyr Asp Trp Ser Thr Thr Ser Gly Thr Phe Pro
        290                 295                 300

Thr Ser Ala Val Ala Gln Gly Ser Gln Leu Val Ile His Ala Val Asp
305                 310                 315                 320

Ser Leu Phe Asn Thr Thr Phe Val Cys Thr Val Thr Asn Ala Val Gly
                325                 330                 335

Met Gly Arg Ala Glu Gln Val Ile Phe Val Arg Glu Thr Pro Asn Thr
            340                 345                 350

Ala Gly Ala Gly Ala Thr Gly Gly Ile Ile Gly Gly Ile Ile Ala Ala
            355                 360                 365

Ile Ile Ala Thr Ala Val Ala Ala Thr Gly Ile Leu Ile Cys Arg Gln
        370                 375                 380

Gln Arg Lys Glu Gln Thr Leu Gln Gly Ala Glu Glu Asp Glu Asp Leu
385                 390                 395                 400

Glu Gly Pro Pro Ser Tyr Lys Pro Pro Thr Pro Lys Ala Lys Leu Glu
                405                 410                 415

Ala Gln Glu Met Pro Ser Gln Leu Phe Thr Leu Gly Ala Ser Glu His
            420                 425                 430

Ser Pro Leu Lys Thr Pro Tyr Phe Asp Ala Gly Ala Ser Cys Thr Glu
            435                 440                 445

Gln Glu Met Pro Arg Tyr His Glu Leu Pro Thr Leu Glu Glu Arg Ser
        450                 455                 460

Gly Pro Leu His Pro Gly Ala Thr Ser Leu Gly Ser Pro Ile Pro Val
465                 470                 475                 480

Pro Pro Gly Pro Pro Ala Val Glu Asp Val Ser Leu Asp Leu Glu Asp
                485                 490                 495

Glu Glu Gly Glu Glu Glu Glu Tyr Leu Asp Lys Ile Asn Pro Ile
            500                 505                 510

Tyr Asp Ala Leu Ser Tyr Ser Ser Pro Ser Asp Ser Tyr Gln Gly Lys
            515                 520                 525

Gly Phe Val Met Ser Arg Ala Met Tyr Val
        530                 535

<210> SEQ ID NO 4
<211> LENGTH: 549
<212> TYPE: PRT
<213> ORGANISM: Homo sapiens

<400> SEQUENCE: 4

Met Ala Arg Thr Leu Arg Pro Ser Pro Leu Cys Pro Gly Gly Gly Lys
1               5                   10                  15

Ala Gln Leu Ser Ser Ala Ser Leu Leu Gly Ala Gly Leu Leu Leu Gln
                20                  25                  30

Pro Pro Thr Pro Pro Pro Leu Leu Leu Leu Leu Phe Pro Leu Leu Leu
            35                  40                  45
```

```
Phe Ser Arg Leu Cys Gly Ala Leu Ala Gly Pro Ile Ile Val Glu Pro
 50                  55                  60
His Val Thr Ala Val Trp Gly Lys Asn Val Ser Leu Lys Cys Leu Ile
 65                  70                  75                  80
Glu Val Asn Glu Thr Ile Thr Gln Ile Ser Trp Glu Lys Ile His Gly
                 85                  90                  95
Lys Ser Ser Gln Thr Val Ala Val His His Pro Gln Tyr Gly Phe Ser
            100                 105                 110
Val Gln Gly Glu Tyr Gln Gly Arg Val Leu Phe Lys Asn Tyr Ser Leu
        115                 120                 125
Asn Asp Ala Thr Ile Thr Leu His Asn Ile Gly Phe Ser Asp Ser Gly
130                 135                 140
Lys Tyr Ile Cys Lys Ala Val Thr Phe Pro Leu Gly Asn Ala Gln Ser
145                 150                 155                 160
Ser Thr Thr Val Thr Val Leu Val Glu Pro Thr Val Ser Leu Ile Lys
                165                 170                 175
Gly Pro Asp Ser Leu Ile Asp Gly Gly Asn Glu Thr Val Ala Ala Ile
            180                 185                 190
Cys Ile Ala Ala Thr Gly Lys Pro Val Ala His Ile Asp Trp Glu Gly
        195                 200                 205
Asp Leu Gly Glu Met Glu Ser Thr Thr Thr Ser Phe Pro Asn Glu Thr
210                 215                 220
Ala Thr Ile Ile Ser Gln Tyr Lys Leu Phe Pro Thr Arg Phe Ala Arg
225                 230                 235                 240
Gly Arg Arg Ile Thr Cys Val Val Lys His Pro Ala Leu Glu Lys Asp
                245                 250                 255
Ile Arg Tyr Ser Phe Ile Leu Asp Ile Gln Tyr Ala Pro Glu Val Ser
            260                 265                 270
Val Thr Gly Tyr Asp Gly Asn Trp Phe Val Gly Arg Lys Gly Val Asn
        275                 280                 285
Leu Lys Cys Asn Ala Asp Ala Asn Pro Pro Pro Phe Lys Ser Val Trp
290                 295                 300
Ser Arg Leu Asp Gly Gln Trp Pro Asp Gly Leu Leu Ala Ser Asp Asn
305                 310                 315                 320
Thr Leu His Phe Val His Pro Leu Thr Phe Asn Tyr Ser Gly Val Tyr
                325                 330                 335
Ile Cys Lys Val Thr Asn Ser Leu Gly Gln Arg Ser Asp Gln Lys Val
            340                 345                 350
Ile Tyr Ile Ser Asp Pro Pro Thr Thr Thr Leu Gln Pro Thr Ile
        355                 360                 365
Gln Trp His Pro Ser Thr Ala Asp Ile Glu Asp Leu Ala Thr Glu Pro
370                 375                 380
Lys Lys Leu Pro Phe Pro Leu Ser Thr Leu Ala Thr Ile Lys Asp Asp
385                 390                 395                 400
Thr Ile Ala Thr Ile Ala Ser Val Val Gly Gly Ala Leu Phe Ile
                405                 410                 415
Val Leu Val Ser Val Leu Ala Gly Ile Phe Cys Tyr Arg Arg Arg
            420                 425                 430
Thr Phe Arg Gly Asp Tyr Phe Ala Lys Asn Tyr Ile Pro Pro Ser Asp
        435                 440                 445
Met Gln Lys Glu Ser Gln Ile Asp Val Leu Gln Asp Glu Leu Asp
450                 455                 460
Ser Tyr Pro Asp Ser Val Lys Lys Glu Asn Lys Asn Pro Val Asn Asn
```

```
                465                 470                 475                 480
Leu Ile Arg Lys Asp Tyr Leu Glu Glu Pro Glu Lys Thr Gln Trp Asn
                    485                 490                 495

Asn Val Glu Asn Leu Asn Arg Phe Glu Arg Pro Met Asp Tyr Tyr Glu
                500                 505                 510

Asp Leu Lys Met Gly Met Lys Phe Val Ser Asp Glu His Tyr Asp Glu
            515                 520                 525

Asn Glu Asp Asp Leu Val Ser His Val Asp Gly Ser Val Ile Ser Arg
530                 535                 540

Arg Glu Trp Tyr Val
545

<210> SEQ ID NO 5
<211> LENGTH: 510
<212> TYPE: PRT
<213> ORGANISM: Homo sapiens

<400> SEQUENCE: 5

Met Pro Leu Ser Leu Gly Ala Glu Met Trp Gly Pro Glu Ala Trp Leu
1               5                   10                  15

Leu Leu Leu Leu Leu Leu Ala Ser Phe Thr Gly Arg Cys Pro Ala Gly
                20                  25                  30

Glu Leu Glu Thr Ser Asp Val Val Thr Val Val Leu Gly Gln Asp Ala
            35                  40                  45

Lys Leu Pro Cys Phe Tyr Arg Gly Asp Ser Gly Glu Gln Val Gly Gln
    50                  55                  60

Val Ala Trp Ala Arg Val Asp Ala Gly Glu Gly Ala Gln Glu Leu Ala
65                  70                  75                  80

Leu Leu His Ser Lys Tyr Gly Leu His Val Ser Pro Ala Tyr Glu Gly
                85                  90                  95

Arg Val Glu Gln Pro Pro Pro Arg Asn Pro Leu Asp Gly Ser Val
            100                 105                 110

Leu Leu Arg Asn Ala Val Gln Ala Asp Glu Gly Glu Tyr Glu Cys Arg
        115                 120                 125

Val Ser Thr Phe Pro Ala Gly Ser Phe Gln Ala Arg Leu Arg Leu Arg
    130                 135                 140

Val Leu Val Pro Pro Leu Pro Ser Leu Asn Pro Gly Pro Ala Leu Glu
145                 150                 155                 160

Glu Gly Gln Gly Leu Thr Leu Ala Ala Ser Cys Thr Ala Glu Gly Ser
                165                 170                 175

Pro Ala Pro Ser Val Thr Trp Asp Thr Glu Val Lys Gly Thr Thr Ser
            180                 185                 190

Ser Arg Ser Phe Lys His Ser Arg Ser Ala Ala Val Thr Ser Glu Phe
        195                 200                 205

His Leu Val Pro Ser Arg Ser Met Asn Gly Gln Pro Leu Thr Cys Val
    210                 215                 220

Val Ser His Pro Gly Leu Leu Gln Asp Gln Arg Ile Thr His Ile Leu
225                 230                 235                 240

His Val Ser Phe Leu Ala Glu Ala Ser Val Arg Gly Leu Glu Asp Gln
                245                 250                 255

Asn Leu Trp His Ile Gly Arg Glu Gly Ala Met Leu Lys Cys Leu Ser
            260                 265                 270

Glu Gly Gln Pro Pro Pro Ser Tyr Asn Trp Thr Arg Leu Asp Gly Pro
        275                 280                 285
```

Leu Pro Ser Gly Val Arg Val Asp Gly Asp Thr Leu Gly Phe Pro Pro
290                 295                 300

Leu Thr Thr Glu His Ser Gly Ile Tyr Val Cys His Val Ser Asn Glu
305                 310                 315                 320

Phe Ser Ser Arg Asp Ser Gln Val Thr Val Asp Val Leu Asp Pro Gln
            325                 330                 335

Glu Asp Ser Gly Lys Gln Val Asp Leu Val Ser Ala Ser Val Val Val
            340                 345                 350

Val Gly Val Ile Ala Ala Leu Leu Phe Cys Leu Leu Val Val Val Val
            355                 360                 365

Val Leu Met Ser Arg Tyr His Arg Arg Lys Ala Gln Gln Met Thr Gln
370                 375                 380

Lys Tyr Glu Glu Glu Leu Thr Leu Thr Arg Glu Asn Ser Ile Arg Arg
385                 390                 395                 400

Leu His Ser His His Thr Asp Pro Arg Ser Gln Pro Glu Glu Ser Val
            405                 410                 415

Gly Leu Arg Ala Glu Gly His Pro Asp Ser Leu Lys Asp Asn Ser Ser
            420                 425                 430

Cys Ser Val Met Ser Glu Glu Pro Glu Gly Arg Ser Tyr Ser Thr Leu
            435                 440                 445

Thr Thr Val Arg Glu Ile Glu Thr Gln Thr Glu Leu Leu Ser Pro Gly
450                 455                 460

Ser Gly Arg Ala Glu Glu Glu Asp Gln Asp Glu Gly Ile Lys Gln
465                 470                 475                 480

Ala Met Asn His Phe Val Gln Glu Asn Gly Thr Leu Arg Ala Lys Pro
            485                 490                 495

Thr Gly Asn Gly Ile Tyr Ile Asn Gly Arg Gly His Leu Val
            500                 505                 510

<210> SEQ ID NO 6
<211> LENGTH: 244
<212> TYPE: PRT
<213> ORGANISM: Homo sapiens

<400> SEQUENCE: 6

Met Arg Trp Cys Leu Leu Leu Ile Trp Ala Gln Gly Leu Arg Gln Ala
1               5                   10                  15

Pro Leu Ala Ser Gly Met Met Thr Gly Thr Ile Glu Thr Thr Gly Asn
            20                  25                  30

Ile Ser Ala Glu Lys Gly Gly Ser Ile Ile Leu Gln Cys His Leu Ser
            35                  40                  45

Ser Thr Thr Ala Gln Val Thr Gln Val Asn Trp Glu Gln Gln Asp Gln
50                  55                  60

Leu Leu Ala Ile Cys Asn Ala Asp Leu Gly Trp His Ile Ser Pro Ser
65                  70                  75                  80

Phe Lys Asp Arg Val Ala Pro Gly Pro Gly Leu Gly Leu Thr Leu Gln
            85                  90                  95

Ser Leu Thr Val Asn Asp Thr Gly Glu Tyr Phe Cys Ile Tyr His Thr
            100                 105                 110

Tyr Pro Asp Gly Thr Tyr Thr Gly Arg Ile Phe Leu Glu Val Leu Glu
            115                 120                 125

Ser Ser Val Ala Glu His Gly Ala Arg Phe Gln Ile Pro Leu Leu Gly
            130                 135                 140

Ala Met Ala Ala Thr Leu Val Val Ile Cys Thr Ala Val Ile Val Val
145                 150                 155                 160

```
Val Ala Leu Thr Arg Lys Lys Ala Leu Arg Ile His Ser Val Glu
            165                 170                 175

Gly Asp Leu Arg Arg Lys Ser Ala Gly Gln Glu Glu Trp Ser Pro Ser
        180                 185                 190

Ala Pro Ser Pro Pro Gly Ser Cys Val Gln Ala Glu Ala Ala Pro Ala
    195                 200                 205

Gly Leu Cys Gly Glu Gln Arg Gly Glu Asp Cys Ala Glu Leu His Asp
210                 215                 220

Tyr Phe Asn Val Leu Ser Tyr Arg Ser Leu Gly Asn Cys Ser Phe Phe
225                 230                 235                 240

Thr Glu Thr Gly

<210> SEQ ID NO 7
<211> LENGTH: 585
<212> TYPE: PRT
<213> ORGANISM: Homo sapiens

<400> SEQUENCE: 7

Met Glu Lys Lys Trp Lys Tyr Cys Ala Val Tyr Tyr Ile Ile Gln Ile
1               5                   10                  15

His Phe Val Lys Gly Val Trp Glu Lys Thr Val Asn Thr Glu Glu Asn
            20                  25                  30

Val Tyr Ala Thr Leu Gly Ser Asp Val Asn Leu Thr Cys Gln Thr Gln
        35                  40                  45

Thr Val Gly Phe Phe Val Gln Met Gln Trp Ser Lys Val Thr Asn Lys
    50                  55                  60

Ile Asp Leu Ile Ala Val Tyr His Pro Gln Tyr Gly Phe Tyr Cys Ala
65                  70                  75                  80

Tyr Gly Arg Pro Cys Glu Ser Leu Val Thr Phe Thr Glu Thr Pro Glu
                85                  90                  95

Asn Gly Ser Lys Trp Thr Leu His Leu Arg Asn Met Ser Cys Ser Val
            100                 105                 110

Ser Gly Arg Tyr Glu Cys Met Leu Val Leu Tyr Pro Glu Gly Ile Gln
        115                 120                 125

Thr Lys Ile Tyr Asn Leu Leu Ile Gln Thr His Val Thr Ala Asp Glu
    130                 135                 140

Trp Asn Ser Asn His Thr Ile Glu Ile Glu Ile Asn Gln Thr Leu Glu
145                 150                 155                 160

Ile Pro Cys Phe Gln Asn Ser Ser Ser Lys Ile Ser Ser Glu Phe Thr
                165                 170                 175

Tyr Ala Trp Ser Val Glu Asn Ser Ser Thr Asp Ser Trp Val Leu Leu
            180                 185                 190

Ser Lys Gly Ile Lys Glu Asp Asn Gly Thr Gln Glu Thr Leu Ile Ser
        195                 200                 205

Gln Asn His Leu Ile Ser Asn Ser Thr Leu Leu Lys Asp Arg Val Lys
    210                 215                 220

Leu Gly Thr Asp Tyr Arg Leu His Leu Ser Pro Val Gln Ile Phe Asp
225                 230                 235                 240

Asp Gly Arg Lys Phe Ser Cys His Ile Arg Val Gly Pro Asn Lys Ile
                245                 250                 255

Leu Arg Ser Ser Thr Thr Val Lys Val Phe Ala Lys Pro Glu Ile Pro
            260                 265                 270

Val Ile Val Glu Asn Asn Ser Thr Asp Val Leu Val Glu Arg Arg Phe
        275                 280                 285
```

```
Thr Cys Leu Leu Lys Asn Val Phe Pro Lys Ala Asn Ile Thr Trp Phe
    290                 295                 300
Ile Asp Gly Ser Phe Leu His Asp Glu Lys Glu Gly Ile Tyr Ile Thr
305                 310                 315                 320
Asn Glu Glu Arg Lys Gly Lys Asp Gly Phe Leu Glu Leu Lys Ser Val
                325                 330                 335
Leu Thr Arg Val His Ser Asn Lys Pro Ala Gln Ser Asp Asn Leu Thr
            340                 345                 350
Ile Trp Cys Met Ala Leu Ser Pro Val Pro Gly Asn Lys Val Trp Asn
        355                 360                 365
Ile Ser Ser Glu Lys Ile Thr Phe Leu Leu Gly Ser Glu Ile Ser Ser
    370                 375                 380
Thr Asp Pro Pro Leu Ser Val Thr Glu Ser Thr Leu Asp Thr Gln Pro
385                 390                 395                 400
Ser Pro Ala Ser Ser Val Ser Pro Ala Arg Tyr Pro Ala Thr Ser Ser
                405                 410                 415
Val Thr Leu Val Asp Val Ser Ala Leu Arg Pro Asn Thr Thr Pro Gln
            420                 425                 430
Pro Ser Asn Ser Ser Met Thr Thr Arg Gly Phe Asn Tyr Pro Trp Thr
        435                 440                 445
Ser Ser Gly Thr Asp Thr Lys Lys Ser Val Ser Arg Ile Pro Ser Glu
    450                 455                 460
Thr Tyr Ser Ser Ser Pro Ser Gly Ala Gly Ser Thr Leu His Asp Asn
465                 470                 475                 480
Val Phe Thr Ser Thr Ala Arg Ala Phe Ser Glu Val Pro Thr Thr Ala
                485                 490                 495
Asn Gly Ser Thr Lys Thr Asn His Val His Ile Thr Gly Ile Val Val
            500                 505                 510
Asn Lys Pro Lys Asp Gly Met Ser Trp Pro Val Ile Val Ala Ala Leu
        515                 520                 525
Leu Phe Cys Cys Met Ile Leu Phe Gly Leu Gly Val Arg Lys Trp Cys
    530                 535                 540
Gln Tyr Gln Lys Glu Ile Met Glu Arg Pro Pro Pro Phe Lys Pro Pro
545                 550                 555                 560
Pro Pro Pro Ile Lys Tyr Thr Cys Ile Gln Glu Pro Asn Glu Ser Asp
                565                 570                 575
Leu Pro Tyr His Glu Met Glu Thr Leu
            580                 585

<210> SEQ ID NO 8
<211> LENGTH: 336
<212> TYPE: PRT
<213> ORGANISM: Homo sapiens

<400> SEQUENCE: 8

Met Asp Tyr Pro Thr Leu Leu Leu Ala Leu Leu His Val Tyr Arg Ala
1               5                   10                  15

Leu Cys Glu Glu Val Leu Trp His Thr Ser Val Pro Phe Ala Glu Asn
            20                  25                  30

Met Ser Leu Glu Cys Val Tyr Pro Ser Met Gly Ile Leu Thr Gln Val
        35                  40                  45

Glu Trp Phe Lys Ile Gly Thr Gln Gln Asp Ser Ile Ala Ile Phe Ser
    50                  55                  60

Pro Thr His Gly Met Val Ile Arg Lys Pro Tyr Ala Glu Arg Val Tyr
```

```
                65                  70                  75                  80
        Phe Leu Asn Ser Thr Met Ala Ser Asn Asn Met Thr Leu Phe Phe Arg
                        85                  90                  95

Asn Ala Ser Glu Asp Asp Val Gly Tyr Tyr Ser Cys Ser Leu Tyr Thr
                        100                 105                 110

Tyr Pro Gln Gly Thr Trp Gln Lys Val Ile Gln Val Gln Ser Asp
                        115                 120                 125

Ser Phe Glu Ala Ala Val Pro Ser Asn Ser His Ile Val Ser Glu Pro
                130                 135                 140

Gly Lys Asn Val Thr Leu Thr Cys Gln Pro Gln Met Thr Trp Pro Val
        145                 150                 155                 160

Gln Ala Val Arg Trp Glu Lys Ile Gln Pro Arg Gln Ile Asp Leu Leu
                        165                 170                 175

Thr Tyr Cys Asn Leu Val His Gly Arg Asn Phe Thr Ser Lys Phe Pro
                        180                 185                 190

Arg Gln Ile Val Ser Asn Cys Ser His Gly Arg Trp Ser Val Ile Val
                        195                 200                 205

Ile Pro Asp Val Thr Val Ser Asp Ser Gly Leu Tyr Arg Cys Tyr Leu
                210                 215                 220

Gln Ala Ser Ala Gly Glu Asn Glu Thr Phe Val Met Arg Leu Thr Val
        225                 230                 235                 240

Ala Glu Gly Lys Thr Asp Asn Gln Tyr Thr Leu Phe Val Ala Gly Gly
                        245                 250                 255

Thr Val Leu Leu Leu Leu Phe Val Ile Ser Ile Thr Thr Ile Ile Val
                        260                 265                 270

Ile Phe Leu Asn Arg Arg Arg Arg Glu Arg Arg Asp Leu Phe Thr
                        275                 280                 285

Glu Ser Trp Asp Thr Gln Lys Ala Pro Asn Asn Tyr Arg Ser Pro Ile
                        290                 295                 300

Ser Thr Ser Gln Pro Thr Asn Gln Ser Met Asp Asp Thr Arg Glu Asp
        305                 310                 315                 320

Ile Tyr Val Asn Tyr Pro Thr Phe Ser Arg Arg Pro Lys Thr Arg Val
                        325                 330                 335

<210> SEQ ID NO 9
<211> LENGTH: 316
<212> TYPE: PRT
<213> ORGANISM: Homo sapiens

<400> SEQUENCE: 9

Asp Val Val Val Gln Ala Pro Thr Gln Val Pro Gly Phe Leu Gly Asp
        1               5                   10                  15

Ser Val Thr Leu Pro Cys Tyr Leu Gln Val Pro Asn Met Glu Val Thr
                        20                  25                  30

His Val Ser Gln Leu Thr Trp Ala Arg His Gly Glu Ser Gly Ser Met
                        35                  40                  45

Ala Val Phe His Gln Thr Gln Gly Pro Ser Tyr Ser Glu Ser Lys Arg
                50                  55                  60

Leu Glu Phe Val Ala Ala Arg Leu Gly Ala Glu Leu Arg Asn Ala Ser
        65                  70                  75                  80

Leu Arg Met Phe Gly Leu Arg Val Glu Asp Glu Gly Asn Tyr Thr Cys
                        85                  90                  95

Leu Phe Val Thr Phe Pro Gln Gly Ser Arg Ser Val Asp Ile Trp Leu
                        100                 105                 110
```

Arg Val Leu Ala Lys Pro Gln Asn Thr Ala Glu Val Gln Lys Val Gln
            115                 120                 125

Leu Thr Gly Glu Pro Val Pro Met Ala Arg Cys Val Ser Thr Gly Gly
    130                 135                 140

Arg Pro Pro Ala Gln Ile Thr Trp His Ser Asp Leu Gly Gly Met Pro
145                 150                 155                 160

Asn Thr Ser Gln Val Pro Gly Phe Leu Ser Gly Thr Val Thr Val Thr
                165                 170                 175

Ser Leu Trp Ile Leu Val Pro Ser Ser Gln Val Asp Gly Lys Asn Val
                180                 185                 190

Thr Cys Lys Val Glu His Glu Ser Phe Glu Lys Pro Gln Leu Leu Thr
    195                 200                 205

Val Asn Leu Thr Val Tyr Tyr Pro Pro Glu Val Ser Ile Ser Gly Tyr
    210                 215                 220

Asp Asn Asn Trp Tyr Leu Gly Gln Asn Glu Ala Thr Leu Thr Cys Asp
225                 230                 235                 240

Ala Arg Ser Asn Pro Glu Pro Thr Gly Tyr Asn Trp Ser Thr Thr Met
                245                 250                 255

Gly Pro Leu Pro Pro Phe Ala Val Ala Gln Gly Ala Gln Leu Leu Ile
                260                 265                 270

Arg Pro Val Asp Lys Pro Ile Asn Thr Thr Leu Ile Cys Asn Val Thr
    275                 280                 285

Asn Ala Leu Gly Ala Arg Gln Ala Glu Leu Thr Val Gln Val Lys Glu
    290                 295                 300

Gly Pro Pro Ser Glu His Ser Gly Met Ser Arg Asn
305                 310                 315

<210> SEQ ID NO 10
<211> LENGTH: 325
<212> TYPE: PRT
<213> ORGANISM: Homo sapiens

<400> SEQUENCE: 10

Gln Val Val Gln Val Asn Asp Ser Met Tyr Gly Phe Ile Gly Thr Asp
1               5                   10                  15

Val Val Leu His Cys Ser Phe Ala Asn Pro Leu Pro Ser Val Lys Ile
                20                  25                  30

Thr Gln Val Thr Trp Gln Lys Ser Thr Asn Gly Ser Lys Gln Asn Val
            35                  40                  45

Ala Ile Tyr Asn Pro Ser Met Gly Val Ser Val Leu Ala Pro Tyr Arg
    50                  55                  60

Glu Arg Val Glu Phe Leu Arg Pro Ser Phe Thr Asp Gly Thr Ile Arg
65                  70                  75                  80

Leu Ser Arg Leu Glu Leu Glu Asp Glu Gly Val Tyr Ile Cys Glu Phe
                85                  90                  95

Ala Thr Phe Pro Thr Gly Asn Arg Glu Ser Gln Leu Asn Leu Thr Val
                100                 105                 110

Met Ala Lys Pro Thr Asn Trp Ile Glu Gly Thr Gln Ala Val Leu Arg
            115                 120                 125

Ala Lys Lys Gly Gln Asp Asp Lys Val Leu Val Ala Thr Cys Thr Ser
    130                 135                 140

Ala Asn Gly Lys Pro Pro Ser Val Val Ser Trp Glu Thr Arg Leu Lys
145                 150                 155                 160

Gly Glu Ala Glu Tyr Gln Glu Ile Arg Asn Pro Asn Gly Thr Val Thr
                165                 170                 175

Val Ile Ser Arg Tyr Arg Leu Val Pro Ser Arg Glu Ala His Gln Gln
            180                 185                 190

Ser Leu Ala Cys Ile Val Asn Tyr His Met Asp Arg Phe Lys Glu Ser
            195                 200                 205

Leu Thr Leu Asn Val Gln Tyr Glu Pro Glu Val Thr Ile Glu Gly Phe
        210                 215                 220

Asp Gly Asn Trp Tyr Leu Gln Arg Met Asp Val Lys Leu Thr Cys Lys
225                 230                 235                 240

Ala Asp Ala Asn Pro Pro Ala Thr Glu Tyr His Trp Thr Thr Leu Asn
                245                 250                 255

Gly Ser Leu Pro Lys Gly Val Glu Ala Gln Asn Arg Thr Leu Phe Phe
            260                 265                 270

Lys Gly Pro Ile Asn Tyr Ser Leu Ala Gly Thr Tyr Ile Cys Glu Ala
            275                 280                 285

Thr Asn Pro Ile Gly Thr Arg Ser Gly Gln Val Glu Val Asn Ile Thr
        290                 295                 300

Glu Phe Pro Tyr Thr Pro Ser Pro Pro Glu His Gly Arg Arg Ala Gly
305                 310                 315                 320

Pro Val Pro Thr Ala
                325

<210> SEQ ID NO 11
<211> LENGTH: 329
<212> TYPE: PRT
<213> ORGANISM: Homo sapiens

<400> SEQUENCE: 11

Gln Asp Val Arg Val Gln Val Leu Pro Glu Val Arg Gly Gln Leu Gly
1               5                   10                  15

Gly Thr Val Glu Leu Pro Cys His Leu Leu Pro Pro Val Pro Gly Leu
            20                  25                  30

Tyr Ile Ser Leu Val Thr Trp Gln Arg Pro Asp Ala Pro Ala Asn His
        35                  40                  45

Gln Asn Val Ala Ala Phe His Pro Lys Met Gly Pro Ser Phe Pro Ser
    50                  55                  60

Pro Lys Pro Gly Ser Glu Arg Leu Ser Phe Val Ser Ala Lys Gln Ser
65                  70                  75                  80

Thr Gly Gln Asp Thr Glu Ala Glu Leu Gln Asp Ala Thr Leu Ala Leu
                85                  90                  95

His Gly Leu Thr Val Glu Asp Glu Gly Asn Tyr Thr Cys Glu Phe Ala
            100                 105                 110

Thr Phe Pro Lys Gly Ser Val Arg Gly Met Thr Trp Leu Arg Val Ile
        115                 120                 125

Ala Lys Pro Lys Asn Gln Ala Glu Ala Gln Lys Val Thr Phe Ser Gln
    130                 135                 140

Asp Pro Thr Thr Val Ala Leu Cys Ile Ser Lys Glu Gly Arg Pro Pro
145                 150                 155                 160

Ala Arg Ile Ser Trp Leu Ser Ser Leu Asp Trp Glu Ala Lys Glu Thr
                165                 170                 175

Gln Val Ser Gly Thr Leu Ala Gly Thr Val Thr Val Thr Ser Arg Phe
            180                 185                 190

Thr Leu Val Pro Ser Gly Arg Ala Asp Gly Val Thr Val Thr Cys Lys
        195                 200                 205

Val Glu His Glu Ser Phe Glu Glu Pro Ala Leu Ile Pro Val Thr Leu

```
                 210                 215                 220
Ser Val Arg Tyr Pro Glu Val Ser Ile Ser Gly Tyr Asp Asp Asn
225                 230                 235                 240

Trp Tyr Leu Gly Arg Thr Asp Ala Thr Leu Ser Cys Asp Val Arg Ser
                245                 250                 255

Asn Pro Glu Pro Thr Gly Tyr Asp Trp Ser Thr Ser Gly Thr Phe
                260                 265                 270

Pro Thr Ser Ala Val Ala Gln Gly Ser Gln Leu Val Ile His Ala Val
                275                 280                 285

Asp Ser Leu Phe Asn Thr Thr Phe Val Cys Thr Val Thr Asn Ala Val
                290                 295                 300

Gly Met Gly Arg Ala Glu Gln Val Ile Phe Val Arg Glu Thr Pro Asn
305                 310                 315                 320

Thr Ala Gly Ala Gly Ala Thr Gly Gly
                325

<210> SEQ ID NO 12
<211> LENGTH: 347
<212> TYPE: PRT
<213> ORGANISM: Homo sapiens

<400> SEQUENCE: 12

Gly Pro Ile Ile Val Glu Pro His Val Thr Ala Val Trp Gly Lys Asn
1               5                   10                  15

Val Ser Leu Lys Cys Leu Ile Glu Val Asn Glu Thr Ile Thr Gln Ile
                20                  25                  30

Ser Trp Glu Lys Ile His Gly Lys Ser Ser Gln Thr Val Ala Val His
            35                  40                  45

His Pro Gln Tyr Gly Phe Ser Val Gln Gly Glu Tyr Gln Gly Arg Val
        50                  55                  60

Leu Phe Lys Asn Tyr Ser Leu Asn Asp Ala Thr Ile Thr Leu His Asn
65                  70                  75                  80

Ile Gly Phe Ser Asp Ser Gly Lys Tyr Ile Cys Lys Ala Val Thr Phe
                85                  90                  95

Pro Leu Gly Asn Ala Gln Ser Ser Thr Thr Val Thr Val Leu Val Glu
                100                 105                 110

Pro Thr Val Ser Leu Ile Lys Gly Pro Asp Ser Leu Ile Asp Gly Gly
                115                 120                 125

Asn Glu Thr Val Ala Ala Ile Cys Ile Ala Thr Gly Lys Pro Val
                130                 135                 140

Ala His Ile Asp Trp Glu Gly Asp Leu Gly Glu Met Glu Ser Thr Thr
145                 150                 155                 160

Thr Ser Phe Pro Asn Glu Thr Ala Thr Ile Ile Ser Gln Tyr Lys Leu
                165                 170                 175

Phe Pro Thr Arg Phe Ala Arg Gly Arg Arg Ile Thr Cys Val Val Lys
                180                 185                 190

His Pro Ala Leu Glu Lys Asp Ile Arg Tyr Ser Phe Ile Leu Asp Ile
                195                 200                 205

Gln Tyr Ala Pro Glu Val Ser Val Thr Gly Tyr Asp Gly Asn Trp Phe
            210                 215                 220

Val Gly Arg Lys Gly Val Asn Leu Lys Cys Asn Ala Asp Ala Asn Pro
225                 230                 235                 240

Pro Pro Phe Lys Ser Val Trp Ser Arg Leu Asp Gly Gln Trp Pro Asp
                245                 250                 255
```

```
Gly Leu Leu Ala Ser Asp Asn Thr Leu His Phe Val His Pro Leu Thr
            260                 265                 270

Phe Asn Tyr Ser Gly Val Tyr Ile Cys Lys Val Thr Asn Ser Leu Gly
        275                 280                 285

Gln Arg Ser Asp Gln Lys Val Ile Tyr Ile Ser Asp Pro Pro Thr Thr
    290                 295                 300

Thr Thr Leu Gln Pro Thr Ile Gln Trp His Pro Ser Thr Ala Asp Ile
305                 310                 315                 320

Glu Asp Leu Ala Thr Glu Pro Lys Lys Leu Pro Phe Pro Leu Ser Thr
                325                 330                 335

Leu Ala Thr Ile Lys Asp Asp Thr Ile Ala Thr
            340                 345

<210> SEQ ID NO 13
<211> LENGTH: 318
<212> TYPE: PRT
<213> ORGANISM: Homo sapiens

<400> SEQUENCE: 13

Gly Glu Leu Glu Thr Ser Asp Val Val Thr Val Leu Gly Gln Asp
1               5                   10                  15

Ala Lys Leu Pro Cys Phe Tyr Arg Gly Asp Ser Gly Glu Gln Val Gly
            20                  25                  30

Gln Val Ala Trp Ala Arg Val Asp Ala Gly Glu Gly Ala Gln Glu Leu
        35                  40                  45

Ala Leu Leu His Ser Lys Tyr Gly Leu His Val Ser Pro Ala Tyr Glu
    50                  55                  60

Gly Arg Val Glu Gln Pro Pro Pro Arg Asn Pro Leu Asp Gly Ser
65                  70                  75                  80

Val Leu Leu Arg Asn Ala Val Gln Ala Asp Glu Gly Glu Tyr Glu Cys
                85                  90                  95

Arg Val Ser Thr Phe Pro Ala Gly Ser Phe Gln Ala Arg Leu Arg Leu
            100                 105                 110

Arg Val Leu Val Pro Pro Leu Pro Ser Leu Asn Pro Gly Pro Ala Leu
        115                 120                 125

Glu Glu Gly Gln Gly Leu Thr Leu Ala Ala Ser Cys Thr Ala Glu Gly
    130                 135                 140

Ser Pro Ala Pro Ser Val Thr Trp Asp Thr Glu Val Lys Gly Thr Thr
145                 150                 155                 160

Ser Ser Arg Ser Phe Lys His Ser Arg Ser Ala Ala Val Thr Ser Glu
                165                 170                 175

Phe His Leu Val Pro Ser Arg Ser Met Asn Gly Gln Pro Leu Thr Cys
            180                 185                 190

Val Val Ser His Pro Gly Leu Leu Gln Asp Gln Arg Ile Thr His Ile
        195                 200                 205

Leu His Val Ser Phe Leu Ala Glu Ala Ser Val Arg Gly Leu Glu Asp
    210                 215                 220

Gln Asn Leu Trp His Ile Gly Arg Glu Gly Ala Met Leu Lys Cys Leu
225                 230                 235                 240

Ser Glu Gly Gln Pro Pro Pro Ser Tyr Asn Trp Thr Arg Leu Asp Gly
                245                 250                 255

Pro Leu Pro Ser Gly Val Arg Val Asp Gly Asp Thr Leu Gly Phe Pro
            260                 265                 270

Pro Leu Thr Thr Glu His Ser Gly Ile Tyr Val Cys His Val Ser Asn
        275                 280                 285
```

Glu Phe Ser Ser Arg Asp Ser Gln Val Thr Val Asp Val Leu Asp Pro
    290                 295                 300

Gln Glu Asp Ser Gly Lys Gln Val Asp Leu Val Ser Ala Ser
305                 310                 315

<210> SEQ ID NO 14
<211> LENGTH: 141
<212> TYPE: PRT
<213> ORGANISM: Homo sapiens

<400> SEQUENCE: 14

Met Met Thr Gly Thr Ile Glu Thr Thr Gly Asn Ile Ser Ala Glu Lys
1               5                   10                  15

Gly Gly Ser Ile Ile Leu Gln Cys His Leu Ser Ser Thr Thr Ala Gln
                20                  25                  30

Val Thr Gln Val Asn Trp Glu Gln Gln Asp Gln Leu Leu Ala Ile Cys
            35                  40                  45

Asn Ala Asp Leu Gly Trp His Ile Ser Pro Ser Phe Lys Asp Arg Val
        50                  55                  60

Ala Pro Gly Pro Gly Leu Gly Leu Thr Leu Gln Ser Leu Thr Val Asn
65                  70                  75                  80

Asp Thr Gly Glu Tyr Phe Cys Ile Tyr His Thr Tyr Pro Asp Gly Thr
                85                  90                  95

Tyr Thr Gly Arg Ile Phe Leu Glu Val Leu Glu Ser Ser Val Ala Glu
                100                 105                 110

His Gly Ala Arg Phe Gln Ile Pro Leu Leu Gly Ala Met Ala Ala Thr
            115                 120                 125

Leu Val Val Ile Cys Thr Ala Val Ile Val Val Val Ala
        130                 135                 140

<210> SEQ ID NO 15
<211> LENGTH: 496
<212> TYPE: PRT
<213> ORGANISM: Homo sapiens

<400> SEQUENCE: 15

Lys Thr Val Asn Thr Glu Glu Asn Val Tyr Ala Thr Leu Gly Ser Asp
1               5                   10                  15

Val Asn Leu Thr Cys Gln Thr Gln Thr Val Gly Phe Phe Val Gln Met
                20                  25                  30

Gln Trp Ser Lys Val Thr Asn Lys Ile Asp Leu Ile Ala Val Tyr His
            35                  40                  45

Pro Gln Tyr Gly Phe Tyr Cys Ala Tyr Gly Arg Pro Cys Glu Ser Leu
        50                  55                  60

Val Thr Phe Thr Glu Thr Pro Glu Asn Gly Ser Lys Trp Thr Leu His
65                  70                  75                  80

Leu Arg Asn Met Ser Cys Ser Val Ser Gly Arg Tyr Glu Cys Met Leu
                85                  90                  95

Val Leu Tyr Pro Glu Gly Ile Gln Thr Lys Ile Tyr Asn Leu Leu Ile
                100                 105                 110

Gln Thr His Val Thr Ala Asp Glu Trp Asn Ser Asn His Thr Ile Glu
            115                 120                 125

Ile Glu Ile Asn Gln Thr Leu Glu Ile Pro Cys Phe Gln Asn Ser Ser
        130                 135                 140

Ser Lys Ile Ser Ser Glu Phe Thr Tyr Ala Trp Ser Val Glu Asn Ser
145                 150                 155                 160

```
Ser Thr Asp Ser Trp Val Leu Leu Ser Lys Gly Ile Lys Glu Asp Asn
            165                 170                 175

Gly Thr Gln Glu Thr Leu Ile Ser Gln Asn His Leu Ile Ser Asn Ser
        180                 185                 190

Thr Leu Leu Lys Asp Arg Val Lys Leu Gly Thr Asp Tyr Arg Leu His
        195                 200                 205

Leu Ser Pro Val Gln Ile Phe Asp Asp Gly Arg Lys Phe Ser Cys His
        210                 215                 220

Ile Arg Val Gly Pro Asn Lys Ile Leu Arg Ser Ser Thr Val Lys
225                 230                 235                 240

Val Phe Ala Lys Pro Glu Ile Pro Val Ile Val Glu Asn Asn Ser Thr
                245                 250                 255

Asp Val Leu Val Glu Arg Arg Phe Thr Cys Leu Leu Lys Asn Val Phe
                260                 265                 270

Pro Lys Ala Asn Ile Thr Trp Phe Ile Asp Gly Ser Phe Leu His Asp
            275                 280                 285

Glu Lys Glu Gly Ile Tyr Ile Thr Asn Glu Glu Arg Lys Gly Lys Asp
        290                 295                 300

Gly Phe Leu Glu Leu Lys Ser Val Leu Thr Arg Val His Ser Asn Lys
305                 310                 315                 320

Pro Ala Gln Ser Asp Asn Leu Thr Ile Trp Cys Met Ala Leu Ser Pro
                325                 330                 335

Val Pro Gly Asn Lys Val Trp Asn Ile Ser Ser Glu Lys Ile Thr Phe
            340                 345                 350

Leu Leu Gly Ser Glu Ile Ser Ser Thr Asp Pro Pro Leu Ser Val Thr
        355                 360                 365

Glu Ser Thr Leu Asp Thr Gln Pro Ser Pro Ala Ser Ser Val Ser Pro
        370                 375                 380

Ala Arg Tyr Pro Ala Thr Ser Ser Val Thr Leu Val Asp Val Ser Ala
385                 390                 395                 400

Leu Arg Pro Asn Thr Thr Pro Gln Pro Ser Asn Ser Ser Met Thr Thr
                405                 410                 415

Arg Gly Phe Asn Tyr Pro Trp Thr Ser Ser Gly Thr Asp Thr Lys Lys
            420                 425                 430

Ser Val Ser Arg Ile Pro Ser Glu Thr Tyr Ser Ser Ser Pro Ser Gly
        435                 440                 445

Ala Gly Ser Thr Leu His Asp Asn Val Phe Thr Ser Thr Ala Arg Ala
        450                 455                 460

Phe Ser Glu Val Pro Thr Thr Ala Asn Gly Ser Thr Lys Thr Asn His
465                 470                 475                 480

Val His Ile Thr Gly Ile Val Val Asn Lys Pro Lys Asp Gly Met Ser
                485                 490                 495

<210> SEQ ID NO 16
<211> LENGTH: 236
<212> TYPE: PRT
<213> ORGANISM: Homo sapiens

<400> SEQUENCE: 16

Glu Glu Val Leu Trp His Thr Ser Val Pro Phe Ala Glu Asn Met Ser
1               5                   10                  15

Leu Glu Cys Val Tyr Pro Ser Met Gly Ile Leu Thr Gln Val Glu Trp
            20                  25                  30

Phe Lys Ile Gly Thr Gln Gln Asp Ser Ile Ala Ile Phe Ser Pro Thr
```

```
                35                  40                  45
His Gly Met Val Ile Arg Lys Pro Tyr Ala Glu Arg Val Tyr Phe Leu
 50                  55                  60

Asn Ser Thr Met Ala Ser Asn Asn Met Thr Leu Phe Phe Arg Asn Ala
 65                  70                  75                  80

Ser Glu Asp Asp Val Gly Tyr Tyr Ser Cys Ser Leu Tyr Thr Tyr Pro
                 85                  90                  95

Gln Gly Thr Trp Gln Lys Val Ile Gln Val Val Gln Ser Asp Ser Phe
                100                 105                 110

Glu Ala Ala Val Pro Ser Asn Ser His Ile Val Ser Glu Pro Gly Lys
            115                 120                 125

Asn Val Thr Leu Thr Cys Gln Pro Gln Met Thr Trp Pro Val Gln Ala
130                 135                 140

Val Arg Trp Glu Lys Ile Gln Pro Arg Gln Ile Asp Leu Leu Thr Tyr
145                 150                 155                 160

Cys Asn Leu Val His Gly Arg Asn Phe Thr Ser Lys Phe Pro Arg Gln
                165                 170                 175

Ile Val Ser Asn Cys Ser His Gly Arg Trp Ser Val Ile Val Ile Pro
                180                 185                 190

Asp Val Thr Val Ser Asp Ser Gly Leu Tyr Arg Cys Tyr Leu Gln Ala
            195                 200                 205

Ser Ala Gly Glu Asn Glu Thr Phe Val Met Arg Leu Thr Val Ala Glu
210                 215                 220

Gly Lys Thr Asp Asn Gln Tyr Thr Leu Phe Val Ala
225                 230                 235

<210> SEQ ID NO 17
<211> LENGTH: 116
<212> TYPE: PRT
<213> ORGANISM: Homo sapiens

<400> SEQUENCE: 17

Asp Val Val Val Gln Ala Pro Thr Gln Val Pro Gly Phe Leu Gly Asp
  1               5                  10                  15

Ser Val Thr Leu Pro Cys Tyr Leu Gln Val Pro Asn Met Glu Val Thr
                 20                  25                  30

His Val Ser Gln Leu Thr Trp Ala Arg His Gly Glu Ser Gly Ser Met
             35                  40                  45

Ala Val Phe His Gln Thr Gln Gly Pro Ser Tyr Ser Glu Ser Lys Arg
 50                  55                  60

Leu Glu Phe Val Ala Ala Arg Leu Gly Ala Glu Leu Arg Asn Ala Ser
 65                  70                  75                  80

Leu Arg Met Phe Gly Leu Arg Val Glu Asp Glu Gly Asn Tyr Thr Cys
                 85                  90                  95

Leu Phe Val Thr Phe Pro Gln Gly Ser Arg Ser Val Asp Ile Trp Leu
                100                 105                 110

Arg Val Leu Ala
            115

<210> SEQ ID NO 18
<211> LENGTH: 112
<212> TYPE: PRT
<213> ORGANISM: Artificial Sequence
<220> FEATURE:
<223> OTHER INFORMATION: Variant 1 Human PVR - N-terminal IgV domain
<220> FEATURE:
<221> NAME/KEY: MISC_FEATURE
```

```
<222> LOCATION: (38)..(38)
<223> OTHER INFORMATION: x can be any amino acid
<220> FEATURE:
<221> NAME/KEY: misc_feature
<222> LOCATION: (40)..(40)
<223> OTHER INFORMATION: Xaa can be any naturally occurring amino acid
<220> FEATURE:
<221> NAME/KEY: MISC_FEATURE
<222> LOCATION: (45)..(47)
<223> OTHER INFORMATION: x can be any amino acid
<220> FEATURE:
<221> NAME/KEY: MISC_FEATURE
<222> LOCATION: (54)..(55)
<223> OTHER INFORMATION: x can be any amino acid
<220> FEATURE:
<221> NAME/KEY: MISC_FEATURE
<222> LOCATION: (57)..(58)
<223> OTHER INFORMATION: x can be any amino acid

<400> SEQUENCE: 18

Asp Val Val Val Gln Ala Pro Thr Gln Val Pro Gly Phe Leu Gly Asp
 1               5                  10                  15

Ser Val Thr Leu Pro Cys Tyr Leu Gln Val Pro Asn Met Glu Val Thr
            20                  25                  30

His Val Ser Gln Leu Xaa Trp Xaa Arg His Gly Glu Xaa Xaa Xaa Met
        35                  40                  45

Ala Val Phe His Gln Xaa Xaa Gly Xaa Xaa Tyr Ser Glu Ser Lys Arg
    50                  55                  60

Leu Glu Phe Val Ala Ala Arg Leu Gly Ala Glu Leu Arg Asn Ala Ser
65                  70                  75                  80

Leu Arg Met Phe Gly Leu Arg Val Glu Asp Glu Gly Asn Tyr Thr Cys
                85                  90                  95

Leu Phe Val Thr Phe Pro Gln Gly Ser Arg Ser Val Asp Ile Trp Leu
            100                 105                 110

<210> SEQ ID NO 19
<211> LENGTH: 112
<212> TYPE: PRT
<213> ORGANISM: Artificial Sequence
<220> FEATURE:
<223> OTHER INFORMATION: Variant 2 Human PVR - N-terminal IgV domain

<400> SEQUENCE: 19

Asp Val Val Val Gln Ala Pro Thr Gln Val Pro Gly Phe Leu Gly Asp
 1               5                  10                  15

Ser Val Thr Leu Pro Cys Tyr Leu Gln Val Pro Asn Met Glu Val Thr
            20                  25                  30

His Val Ser Gln Leu Thr Trp Ala Arg His Gly Glu Asn Gly Ser Met
        35                  40                  45

Ala Val Phe His Gln Thr Gln Gly Pro Ser Tyr Ser Glu Ser Lys Arg
    50                  55                  60

Leu Glu Phe Val Ala Ala Arg Leu Gly Ala Glu Leu Arg Asn Ala Ser
65                  70                  75                  80

Leu Arg Met Phe Gly Leu Arg Val Glu Asp Glu Gly Asn Tyr Thr Cys
                85                  90                  95

Leu Phe Val Thr Phe Pro Gln Gly Ser Arg Ser Val Asp Ile Trp Leu
            100                 105                 110

<210> SEQ ID NO 20
<211> LENGTH: 112
<212> TYPE: PRT
<213> ORGANISM: Artificial Sequence
<220> FEATURE:
```

<223> OTHER INFORMATION: Variant 3 Human PVR - N-terminal IgV domain

<400> SEQUENCE: 20

```
Asp Val Val Gln Ala Pro Thr Gln Val Pro Gly Phe Leu Gly Asp
1               5                   10                  15

Ser Val Thr Leu Pro Cys Tyr Leu Gln Val Pro Asn Met Glu Val Thr
            20                  25                  30

His Val Ser Gln Leu Thr Trp Ala Arg His Gly Glu Ser Gly Ser Met
        35                  40                  45

Ala Val Phe His Gln Thr Lys Gly Pro Ser Tyr Ser Glu Ser Lys Arg
    50                  55                  60

Leu Glu Phe Val Ala Ala Arg Leu Gly Ala Glu Leu Arg Asn Ala Ser
65                  70                  75                  80

Leu Arg Met Phe Gly Leu Arg Val Glu Asp Glu Gly Asn Tyr Thr Cys
                85                  90                  95

Leu Phe Val Thr Phe Pro Gln Gly Ser Arg Ser Val Asp Ile Trp Leu
            100                 105                 110
```

<210> SEQ ID NO 21
<211> LENGTH: 112
<212> TYPE: PRT
<213> ORGANISM: Artificial Sequence
<220> FEATURE:
<223> OTHER INFORMATION: Variant 4 Human PVR - N-terminal IgV domain

<400> SEQUENCE: 21

```
Asp Val Val Gln Ala Pro Thr Gln Val Pro Gly Phe Leu Gly Asp
1               5                   10                  15

Ser Val Thr Leu Pro Cys Tyr Leu Gln Val Pro Asn Met Glu Val Thr
            20                  25                  30

His Val Ser Gln Leu Thr Trp Ala Arg His Gly Glu Asn Gly Ser Met
        35                  40                  45

Ala Val Phe His Gln Thr Lys Gly Pro Ser Tyr Ser Glu Ser Lys Arg
    50                  55                  60

Leu Glu Phe Val Ala Ala Arg Leu Gly Ala Glu Leu Arg Asn Ala Ser
65                  70                  75                  80

Leu Arg Met Phe Gly Leu Arg Val Glu Asp Glu Gly Asn Tyr Thr Cys
                85                  90                  95

Leu Phe Val Thr Phe Pro Gln Gly Ser Arg Ser Val Asp Ile Trp Leu
            100                 105                 110
```

<210> SEQ ID NO 22
<211> LENGTH: 114
<212> TYPE: PRT
<213> ORGANISM: Homo sapiens

<400> SEQUENCE: 22

```
Gln Val Val Gln Val Asn Asp Ser Met Tyr Gly Phe Ile Gly Thr Asp
1               5                   10                  15

Val Val Leu His Cys Ser Phe Ala Asn Pro Leu Pro Ser Val Lys Ile
            20                  25                  30

Thr Gln Val Thr Trp Gln Lys Ser Thr Asn Gly Ser Lys Gln Asn Val
        35                  40                  45

Ala Ile Tyr Asn Pro Ser Met Gly Val Ser Val Leu Ala Pro Tyr Arg
    50                  55                  60

Glu Arg Val Glu Phe Leu Arg Pro Ser Phe Thr Asp Gly Thr Ile Arg
65                  70                  75                  80
```

```
Leu Ser Arg Leu Glu Leu Glu Asp Glu Gly Val Tyr Ile Cys Glu Phe
            85                  90                  95

Ala Thr Phe Pro Thr Gly Asn Arg Glu Ser Gln Leu Asn Leu Thr Val
            100                 105                 110

Met Ala

<210> SEQ ID NO 23
<211> LENGTH: 128
<212> TYPE: PRT
<213> ORGANISM: Homo sapiens

<400> SEQUENCE: 23

Asp Val Arg Val Gln Val Leu Pro Glu Val Arg Gly Gln Leu Gly Gly
1               5                   10                  15

Thr Val Glu Leu Pro Cys His Leu Leu Pro Pro Val Pro Gly Leu Tyr
            20                  25                  30

Ile Ser Leu Val Thr Trp Gln Arg Pro Asp Ala Pro Ala Asn His Gln
            35                  40                  45

Asn Val Ala Ala Phe His Pro Lys Met Gly Pro Ser Phe Pro Ser Pro
        50                  55                  60

Lys Pro Gly Ser Glu Arg Leu Ser Phe Val Ser Ala Lys Gln Ser Thr
65                  70                  75                  80

Gly Gln Asp Thr Glu Ala Glu Leu Gln Asp Ala Thr Leu Ala Leu His
                85                  90                  95

Gly Leu Thr Val Glu Asp Glu Gly Asn Tyr Thr Cys Glu Phe Ala Thr
            100                 105                 110

Phe Pro Lys Gly Ser Val Arg Gly Met Thr Trp Leu Arg Val Ile Ala
            115                 120                 125

<210> SEQ ID NO 24
<211> LENGTH: 111
<212> TYPE: PRT
<213> ORGANISM: Homo sapiens

<400> SEQUENCE: 24

Gly Pro Ile Ile Val Glu Pro His Val Thr Ala Val Trp Gly Lys Asn
1               5                   10                  15

Val Ser Leu Lys Cys Leu Ile Glu Val Asn Glu Thr Ile Thr Gln Ile
            20                  25                  30

Ser Trp Glu Lys Ile His Gly Lys Ser Ser Gln Thr Val Ala Val His
            35                  40                  45

His Pro Gln Tyr Gly Phe Ser Val Gln Gly Glu Tyr Gln Gly Arg Val
        50                  55                  60

Leu Phe Lys Asn Tyr Ser Leu Asn Asp Ala Thr Ile Thr Leu His Asn
65                  70                  75                  80

Ile Gly Phe Ser Asp Ser Gly Lys Tyr Ile Cys Lys Ala Val Thr Phe
                85                  90                  95

Pro Leu Gly Asn Ala Gln Ser Ser Thr Thr Val Thr Val Leu Val
            100                 105                 110

<210> SEQ ID NO 25
<211> LENGTH: 120
<212> TYPE: PRT
<213> ORGANISM: Homo sapiens

<400> SEQUENCE: 25

Gly Glu Leu Glu Thr Ser Asp Val Val Thr Val Val Leu Gly Gln Asp
1               5                   10                  15
```

Ala Lys Leu Pro Cys Phe Tyr Arg Gly Asp Ser Gly Glu Gln Val Gly
            20                  25                  30

Gln Val Ala Trp Ala Arg Val Asp Ala Gly Glu Gly Ala Gln Glu Leu
        35                  40                  45

Ala Leu Leu His Ser Lys Tyr Gly Leu His Val Ser Pro Ala Tyr Glu
    50                  55                  60

Gly Arg Val Glu Gln Pro Pro Pro Arg Asn Pro Leu Asp Gly Ser
65                  70                  75                  80

Val Leu Leu Arg Asn Ala Val Gln Ala Asp Glu Gly Glu Tyr Glu Cys
                85                  90                  95

Arg Val Ser Thr Phe Pro Ala Gly Ser Phe Gln Ala Arg Leu Arg Leu
            100                 105                 110

Arg Val Leu Val Pro Pro Leu Pro
        115                 120

<210> SEQ ID NO 26
<211> LENGTH: 227
<212> TYPE: PRT
<213> ORGANISM: Homo sapiens

<400> SEQUENCE: 26

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 27
<211> LENGTH: 230
<212> TYPE: PRT

<213> ORGANISM: Homo sapiens

<400> SEQUENCE: 27

Lys Ser Ser Asp Lys Thr His Thr Cys Pro Pro Cys Pro Ala Pro Glu
1               5                   10                  15

Leu Leu Gly Gly Pro Ser Val Phe Leu Phe Pro Pro Lys Pro Lys Asp
            20                  25                  30

Thr Leu Met Ile Ser Arg Thr Pro Glu Val Thr Cys Val Val Val Asp
        35                  40                  45

Val Ser His Glu Asp Pro Glu Val Lys Phe Asn Trp Tyr Val Asp Gly
    50                  55                  60

Val Glu Val His Asn Ala Lys Thr Lys Pro Arg Glu Glu Gln Tyr Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Ala Leu Pro
            100                 105                 110

Ala Pro Ile Glu Lys Thr Ile Ser Lys Ala Lys Gly Gln Pro Arg Glu
        115                 120                 125

Pro Gln Val Tyr Thr Leu Pro Pro Ser Arg Asp Glu Leu Thr Lys Asn
130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Lys
            180                 185                 190

Leu Thr Val Asp Lys Ser Arg Trp Gln Gln Gly Asn Val Phe Ser Cys
        195                 200                 205

Ser Val Met His Glu Ala Leu His Asn His Tyr Thr Gln Lys Ser Leu
    210                 215                 220

Ser Leu Ser Pro Gly Lys
225                 230

<210> SEQ ID NO 28
<211> LENGTH: 232
<212> TYPE: PRT
<213> ORGANISM: Homo sapiens

<400> SEQUENCE: 28

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro

```
                    115                 120                 125
Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 29
<211> LENGTH: 224
<212> TYPE: PRT
<213> ORGANISM: Homo sapiens

<400> SEQUENCE: 29

Cys Val Glu Cys Pro Pro Cys Pro Ala Pro Pro Val Ala Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
        35                  40                  45

Glu Val Gln Phe Asn Trp Tyr Val Asp Gly Val Glu Val His Asn Ala
    50                  55                  60

Lys Thr Lys Pro Arg Glu Glu Gln Phe Asn Ser Thr Phe Arg Val Val
65                  70                  75                  80

Ser Val Leu Thr Val Val His Gln Asp Trp Leu Asn Gly Lys Glu Tyr
                85                  90                  95

Lys Cys Lys Val Ser Asn Lys Gly Leu Pro Ala Pro Ile Glu Lys Thr
            100                 105                 110

Ile Ser Lys Thr Lys Gly Gln Pro Arg Glu Pro Gln Val Tyr Thr Leu
        115                 120                 125

Pro Pro Ser Arg Glu Glu Met Thr Lys Asn Gln Val Ser Leu Thr Cys
    130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Met Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Gly Lys
    210                 215                 220

<210> SEQ ID NO 30
<211> LENGTH: 224
<212> TYPE: PRT
<213> ORGANISM: Homo sapiens
```

<400> SEQUENCE: 30

```
Cys Val Glu Cys Pro Pro Cys Pro Ala Pro Val Ala Gly Pro Ser
  1               5                  10                  15
Val Phe Leu Phe Pro Pro Lys Pro Lys Asp Thr Leu Met Ile Ser Arg
             20                  25                  30
Thr Pro Glu Val Thr Cys Val Val Asp Val Ser His Glu Asp Pro
             35                  40                  45
Glu Val Gln Phe Asn Trp Tyr Val Asp Gly Val Glu Val His Asn Ala
         50                  55                  60
Lys Thr Lys Pro Arg Glu Glu Gln Phe Asn Ser Thr Phe Arg Val Val
 65                  70                  75                  80
Ser Val Leu Thr Val Val His Gln Asp Trp Leu Asn Gly Lys Glu Tyr
                 85                  90                  95
Lys Cys Lys Val Ser Asn Lys Gly Leu Pro Ala Pro Ile Glu Lys Thr
                100                 105                 110
Ile Ser Lys Thr Lys Gly Gln Pro Arg Glu Pro Gln Val Tyr Thr Leu
            115                 120                 125
Pro Pro Ser Arg Glu Glu Met Thr Lys Asn Gln Val Ser Leu Thr Cys
        130                 135                 140
Leu Val Glu Gly Phe Tyr Pro Ser Asp Ile Ala Val Glu Trp Glu Ser
145                 150                 155                 160
Asn Gly Gln Pro Glu Asn Asn Tyr Lys Thr Thr Pro Pro Met Leu Asp
                165                 170                 175
Ser Asp Gly Ser Phe Phe Leu Tyr Ser Glu Leu Thr Val Asp Lys Ser
            180                 185                 190
Arg Trp Gln Gln Gly Asn Val Phe Ser Cys Ser Val Met His Glu Ala
        195                 200                 205
Leu His Asn His Tyr Thr Gln Lys Ser Leu Ser Leu Ser Pro Gly Lys
    210                 215                 220
```

<210> SEQ ID NO 31
<211> LENGTH: 224
<212> TYPE: PRT
<213> ORGANISM: Homo sapiens

<400> SEQUENCE: 31

```
Cys Val Glu Cys Pro Pro Cys Pro Ala Pro Val Ala Gly Pro Ser
  1               5                  10                  15
Val Phe Leu Phe Pro Pro Lys Pro Lys Asp Thr Leu Met Ile Ser Arg
             20                  25                  30
Thr Pro Glu Val Thr Cys Val Val Asp Val Ser His Glu Asp Pro
             35                  40                  45
Glu Val Gln Phe Asn Trp Tyr Val Asp Gly Val Glu Val His Asn Ala
         50                  55                  60
Lys Thr Lys Pro Arg Glu Glu Gln Phe Asn Ser Thr Phe Arg Val Val
 65                  70                  75                  80
Ser Val Leu Thr Val Val His Gln Asp Trp Leu Asn Gly Lys Glu Tyr
                 85                  90                  95
Lys Cys Lys Val Ser Asn Lys Gly Leu Pro Ala Pro Ile Glu Lys Thr
                100                 105                 110
Ile Ser Lys Thr Lys Gly Gln Pro Arg Glu Pro Gln Val Tyr Thr Leu
            115                 120                 125
Pro Pro Ser Arg Glu Lys Met Thr Lys Asn Gln Val Ser Leu Thr Cys
        130                 135                 140
```

```
Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Met Leu Lys
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Gly Lys
    210                 215                 220

<210> SEQ ID NO 32
<211> LENGTH: 8
<212> TYPE: PRT
<213> ORGANISM: Artificial Sequence
<220> FEATURE:
<223> OTHER INFORMATION: FLAG Tag

<400> SEQUENCE: 32

Asp Tyr Lys Asp Asp Asp Asp Lys
1               5

<210> SEQ ID NO 33
<211> LENGTH: 8
<212> TYPE: PRT
<213> ORGANISM: Artificial Sequence
<220> FEATURE:
<223> OTHER INFORMATION: Linker

<400> SEQUENCE: 33

Glu Ser Gly Gly Gly Gly Val Thr
1               5

<210> SEQ ID NO 34
<211> LENGTH: 9
<212> TYPE: PRT
<213> ORGANISM: Artificial Sequence
<220> FEATURE:
<223> OTHER INFORMATION: Linker

<400> SEQUENCE: 34

Leu Glu Ser Gly Gly Gly Gly Val Thr
1               5

<210> SEQ ID NO 35
<211> LENGTH: 6
<212> TYPE: PRT
<213> ORGANISM: Artificial Sequence
<220> FEATURE:
<223> OTHER INFORMATION: Linker

<400> SEQUENCE: 35

Gly Arg Ala Gln Val Thr
1               5

<210> SEQ ID NO 36
<211> LENGTH: 6
<212> TYPE: PRT
<213> ORGANISM: Artificial Sequence
<220> FEATURE:
<223> OTHER INFORMATION: Linker

<400> SEQUENCE: 36

Trp Arg Ala Gln Val Thr
1               5
```

<210> SEQ ID NO 37
<211> LENGTH: 8
<212> TYPE: PRT
<213> ORGANISM: Artificial Sequence
<220> FEATURE:
<223> OTHER INFORMATION: Linker

<400> SEQUENCE: 37

Ala Arg Gly Arg Ala Gln Val Thr
1               5

<210> SEQ ID NO 38
<211> LENGTH: 128
<212> TYPE: PRT
<213> ORGANISM: Artificial Sequence
<220> FEATURE:
<223> OTHER INFORMATION: Variant human PVRL2 - N-terminal IgV domain
<220> FEATURE:
<221> NAME/KEY: MISC_FEATURE
<222> LOCATION: (37)..(37)
<223> OTHER INFORMATION: x can be any amino acid
<220> FEATURE:
<221> NAME/KEY: MISC_FEATURE
<222> LOCATION: (39)..(39)
<223> OTHER INFORMATION: x can be any amino acid
<220> FEATURE:
<221> NAME/KEY: MISC_FEATURE
<222> LOCATION: (47)..(49)
<223> OTHER INFORMATION: x can be any amino acid
<220> FEATURE:
<221> NAME/KEY: MISC_FEATURE
<222> LOCATION: (56)..(57)
<223> OTHER INFORMATION: x can be any amino acid
<220> FEATURE:
<221> NAME/KEY: MISC_FEATURE
<222> LOCATION: (59)..(60)
<223> OTHER INFORMATION: x can be any amino acid

<400> SEQUENCE: 38

Asp Val Arg Val Gln Val Leu Pro Glu Val Arg Gly Gln Leu Gly Gly
1               5                   10                  15

Thr Val Glu Leu Pro Cys His Leu Leu Pro Pro Val Pro Gly Leu Tyr
            20                  25                  30

Ile Ser Leu Val Xaa Trp Xaa Arg Pro Asp Ala Pro Ala Asn Xaa Xaa
        35                  40                  45

Xaa Val Ala Ala Phe His Pro Xaa Xaa Gly Xaa Xaa Phe Pro Ser Pro
    50                  55                  60

Lys Pro Gly Ser Glu Arg Leu Ser Phe Val Ser Ala Lys Gln Ser Thr
65                  70                  75                  80

Gly Gln Asp Thr Glu Ala Glu Leu Gln Asp Ala Thr Leu Ala Leu His
                85                  90                  95

Gly Leu Thr Val Glu Asp Glu Gly Asn Tyr Thr Cys Glu Phe Ala Thr
            100                 105                 110

Phe Pro Lys Gly Ser Val Arg Gly Met Thr Trp Leu Arg Val Ile Ala
        115                 120                 125

<210> SEQ ID NO 39
<211> LENGTH: 330
<212> TYPE: PRT
<213> ORGANISM: Homo sapiens

<400> SEQUENCE: 39

Ala Ser Thr Lys Gly Pro Ser Val Phe Pro Leu Ala Pro Ser Ser Lys
1               5                   10                  15

```
Ser Thr Ser Gly Gly Thr Ala Ala Leu Gly Cys Leu Val Lys Asp Tyr
         20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 40
<211> LENGTH: 326
<212> TYPE: PRT
<213> ORGANISM: Homo sapiens

<400> SEQUENCE: 40

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
         20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
         50                  55                  60
```

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
                180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 41
<211> LENGTH: 377
<212> TYPE: PRT
<213> ORGANISM: Homo sapiens

<400> SEQUENCE: 41

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro

```
            100                 105                 110
Arg Cys Pro Glu Pro Lys Ser Cys Asp Thr Pro Pro Cys Pro Arg
        115                 120                 125

Cys Pro Glu Pro Lys Ser Cys Asp Thr Pro Pro Cys Pro Arg Cys
        130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
        210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
        290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
        370                 375

<210> SEQ ID NO 42
<211> LENGTH: 327
<212> TYPE: PRT
<213> ORGANISM: Homo sapiens

<400> SEQUENCE: 42

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95
```

```
Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 43
<211> LENGTH: 235
<212> TYPE: PRT
<213> ORGANISM: Homo sapiens

<400> SEQUENCE: 43

Thr Lys Val Asp Lys Thr Val Glu Arg Lys Cys Cys Val Glu Cys Pro
1               5                   10                  15

Pro Cys Pro Ala Pro Pro Val Ala Gly Pro Ser Val Phe Leu Phe Pro
            20                  25                  30

Pro Lys Pro Lys Asp Thr Leu Met Ile Ser Arg Thr Pro Glu Val Thr
        35                  40                  45

Cys Val Val Val Asp Val Ser His Glu Asp Pro Glu Val Gln Phe Asn
    50                  55                  60

Trp Tyr Val Asp Gly Val Glu Val His Asn Ala Lys Thr Lys Pro Arg
65                  70                  75                  80

Glu Glu Gln Phe Asn Ser Thr Phe Arg Val Val Ser Val Leu Thr Val
                85                  90                  95

Val His Gln Asp Trp Leu Asn Gly Lys Glu Tyr Lys Cys Lys Val Ser
            100                 105                 110

Asn Lys Gly Leu Pro Ala Pro Ile Glu Lys Thr Ile Ser Lys Thr Lys
        115                 120                 125

Gly Gln Pro Arg Glu Pro Gln Val Tyr Thr Leu Pro Pro Ser Arg Glu
    130                 135                 140
```

Glu Met Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Met Leu Asp Ser Asp Gly Ser Phe
            180                 185                 190

Phe Leu Tyr Ser Lys Leu Thr Val Asp Lys Ser Arg Trp Gln Gln Gly
        195                 200                 205

Asn Val Phe Ser Cys Ser Val Met His Glu Ala Leu His Asn His Tyr
    210                 215                 220

Thr Gln Lys Ser Leu Ser Leu Ser Pro Gly Lys
225                 230                 235

<210> SEQ ID NO 44
<211> LENGTH: 235
<212> TYPE: PRT
<213> ORGANISM: Homo sapiens

<400> SEQUENCE: 44

Thr Lys Val Asp Lys Thr Val Glu Arg Lys Ser Cys Val Glu Cys Pro
1               5                   10                  15

Pro Cys Pro Ala Pro Pro Val Ala Gly Pro Ser Val Phe Leu Phe Pro
                20                  25                  30

Pro Lys Pro Lys Asp Thr Leu Met Ile Ser Arg Thr Pro Glu Val Thr
            35                  40                  45

Cys Val Val Val Asp Val Ser His Glu Asp Pro Glu Val Gln Phe Asn
    50                  55                  60

Trp Tyr Val Asp Gly Val Glu Val His Asn Ala Lys Thr Lys Pro Arg
65                  70                  75                  80

Glu Glu Gln Phe Asn Ser Thr Phe Arg Val Val Ser Val Leu Thr Val
                85                  90                  95

Val His Gln Asp Trp Leu Asn Gly Lys Glu Tyr Lys Cys Lys Val Ser
            100                 105                 110

Asn Lys Gly Leu Pro Ala Pro Ile Glu Lys Thr Ile Ser Lys Thr Lys
        115                 120                 125

Gly Gln Pro Arg Glu Pro Gln Val Tyr Thr Leu Pro Pro Ser Arg Glu
    130                 135                 140

Glu Met Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Met Leu Asp Ser Asp Gly Ser Phe
            180                 185                 190

Phe Leu Tyr Ser Lys Leu Thr Val Asp Lys Ser Arg Trp Gln Gln Gly
        195                 200                 205

Asn Val Phe Ser Cys Ser Val Met His Glu Ala Leu His Asn His Tyr
    210                 215                 220

Thr Gln Lys Ser Leu Ser Leu Ser Pro Gly Lys
225                 230                 235

<210> SEQ ID NO 45
<211> LENGTH: 235
<212> TYPE: PRT
<213> ORGANISM: Homo sapiens

<400> SEQUENCE: 45

Thr Lys Val Asp Lys Thr Val Glu Arg Lys Cys Val Glu Cys Pro
1               5                  10                 15

Pro Cys Pro Ala Pro Val Ala Gly Pro Ser Val Phe Leu Phe Pro
                20                  25                 30

Pro Lys Pro Lys Asp Thr Leu Met Ile Ser Arg Thr Pro Glu Val Thr
                35                  40                 45

Cys Val Val Val Asp Val Ser His Glu Asp Pro Glu Val Gln Phe Asn
        50                  55                  60

Trp Tyr Val Asp Gly Val Glu Val His Asn Ala Lys Thr Lys Pro Arg
65                      70                  75                  80

Glu Glu Gln Phe Asn Ser Thr Phe Arg Val Val Ser Val Leu Thr Val
                    85                  90                  95

Val His Gln Asp Trp Leu Asn Gly Lys Glu Tyr Lys Cys Lys Val Ser
                100                 105                 110

Asn Lys Gly Leu Pro Ala Pro Ile Glu Lys Thr Ile Ser Lys Thr Lys
                115                 120                 125

Gly Gln Pro Arg Glu Pro Gln Val Tyr Thr Leu Pro Pro Ser Arg Glu
                130                 135                 140

Lys Met Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Met Leu Lys Ser Asp Gly Ser Phe
                180                 185                 190

Phe Leu Tyr Ser Lys Leu Thr Val Asp Lys Ser Arg Trp Gln Gln Gly
                195                 200                 205

Asn Val Phe Ser Cys Ser Val Met His Glu Ala Leu His Asn His Tyr
                210                 215                 220

Thr Gln Lys Ser Leu Ser Leu Ser Pro Gly Lys
225                 230                 235

<210> SEQ ID NO 46
<211> LENGTH: 235
<212> TYPE: PRT
<213> ORGANISM: Homo sapiens

<400> SEQUENCE: 46

Thr Lys Val Asp Lys Thr Val Glu Arg Lys Ser Val Glu Cys Pro
1               5                  10                 15

Pro Cys Pro Ala Pro Val Ala Gly Pro Ser Val Phe Leu Phe Pro
                20                  25                 30

Pro Lys Pro Lys Asp Thr Leu Met Ile Ser Arg Thr Pro Glu Val Thr
                35                  40                 45

Cys Val Val Val Asp Val Ser His Glu Asp Pro Glu Val Gln Phe Asn
        50                  55                  60

Trp Tyr Val Asp Gly Val Glu Val His Asn Ala Lys Thr Lys Pro Arg
65                      70                  75                  80

Glu Glu Gln Phe Asn Ser Thr Phe Arg Val Val Ser Val Leu Thr Val
                    85                  90                  95

Val His Gln Asp Trp Leu Asn Gly Lys Glu Tyr Lys Cys Lys Val Ser
                100                 105                 110

Asn Lys Gly Leu Pro Ala Pro Ile Glu Lys Thr Ile Ser Lys Thr Lys
                115                 120                 125

Gly Gln Pro Arg Glu Pro Gln Val Tyr Thr Leu Pro Pro Ser Arg Glu

```
              130                 135                 140
Lys Met Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Met Leu Lys Ser Asp Gly Ser Phe
                180                 185                 190

Phe Leu Tyr Ser Lys Leu Thr Val Asp Lys Ser Arg Trp Gln Gln Gly
                195                 200                 205

Asn Val Phe Ser Cys Ser Val Met His Glu Ala Leu His Asn His Tyr
                210                 215                 220

Thr Gln Lys Ser Leu Ser Leu Ser Pro Gly Lys
225                 230                 235

<210> SEQ ID NO 47
<211> LENGTH: 235
<212> TYPE: PRT
<213> ORGANISM: Homo sapiens

<400> SEQUENCE: 47

Thr Lys Val Asp Lys Thr Val Glu Arg Lys Cys Cys Val Glu Cys Pro
1               5                   10                  15

Pro Cys Pro Ala Pro Pro Val Ala Gly Pro Ser Val Phe Leu Phe Pro
                20                  25                  30

Pro Lys Pro Lys Asp Thr Leu Met Ile Ser Arg Thr Pro Glu Val Thr
                35                  40                  45

Cys Val Val Val Asp Val Ser His Glu Asp Pro Glu Val Gln Phe Asn
50                  55                  60

Trp Tyr Val Asp Gly Val Glu Val His Asn Ala Lys Thr Lys Pro Arg
65                  70                  75                  80

Glu Glu Gln Phe Asn Ser Thr Phe Arg Val Val Ser Val Leu Thr Val
                85                  90                  95

Val His Gln Asp Trp Leu Asn Gly Lys Glu Tyr Lys Cys Lys Val Ser
                100                 105                 110

Asn Lys Gly Leu Pro Ala Pro Ile Glu Lys Thr Ile Ser Lys Thr Lys
                115                 120                 125

Gly Gln Pro Arg Glu Pro Gln Val Tyr Thr Leu Pro Pro Ser Arg Glu
130                 135                 140

Glu Met Thr Lys Asn Gln Val Ser Leu Thr Cys Leu Val Glu Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Met Leu Asp Ser Asp Gly Ser Phe
                180                 185                 190

Phe Leu Tyr Ser Glu Leu Thr Val Asp Lys Ser Arg Trp Gln Gln Gly
                195                 200                 205

Asn Val Phe Ser Cys Ser Val Met His Glu Ala Leu His Asn His Tyr
                210                 215                 220

Thr Gln Lys Ser Leu Ser Leu Ser Pro Gly Lys
225                 230                 235

<210> SEQ ID NO 48
<211> LENGTH: 235
<212> TYPE: PRT
<213> ORGANISM: Homo sapiens
```

```
<400> SEQUENCE: 48

Thr Lys Val Asp Lys Thr Val Glu Arg Lys Ser Cys Val Cys Pro
1               5                   10                  15

Pro Cys Pro Ala Pro Val Ala Gly Pro Ser Val Phe Leu Phe Pro
                20                  25                  30

Pro Lys Pro Lys Asp Thr Leu Met Ile Ser Arg Thr Pro Glu Val Thr
        35                  40                  45

Cys Val Val Val Asp Val Ser His Glu Asp Pro Glu Val Gln Phe Asn
    50                  55                  60

Trp Tyr Val Asp Gly Val Glu Val His Asn Ala Lys Thr Lys Pro Arg
65              70                  75                  80

Glu Glu Gln Phe Asn Ser Thr Phe Arg Val Val Ser Val Leu Thr Val
                    85                  90                  95

Val His Gln Asp Trp Leu Asn Gly Lys Glu Tyr Lys Cys Lys Val Ser
                100                 105                 110

Asn Lys Gly Leu Pro Ala Pro Ile Glu Lys Thr Ile Ser Lys Thr Lys
            115                 120                 125

Gly Gln Pro Arg Glu Pro Gln Val Tyr Thr Leu Pro Pro Ser Arg Glu
        130                 135                 140

Glu Met Thr Lys Asn Gln Val Ser Leu Thr Cys Leu Val Glu Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Met Leu Asp Ser Asp Gly Ser Phe
            180                 185                 190

Phe Leu Tyr Ser Glu Leu Thr Val Asp Lys Ser Arg Trp Gln Gln Gly
        195                 200                 205

Asn Val Phe Ser Cys Ser Val Met His Glu Ala Leu His Asn His Tyr
    210                 215                 220

Thr Gln Lys Ser Leu Ser Leu Ser Pro Gly Lys
225                 230                 235

<210> SEQ ID NO 49
<211> LENGTH: 119
<212> TYPE: PRT
<213> ORGANISM: Mus musculus

<400> SEQUENCE: 49

Asp Val Arg Val Arg Val Leu Pro Glu Val Arg Gly Arg Leu Gly Gly
1               5                   10                  15

Thr Val Glu Leu Pro Cys His Leu Leu Pro Pro Thr Thr Glu Arg Val
                20                  25                  30

Ser Gln Val Thr Trp Gln Arg Leu Asp Gly Thr Val Val Ala Ala Phe
            35                  40                  45

His Pro Ser Phe Gly Val Asp Phe Pro Asn Ser Gln Phe Ser Lys Asp
    50                  55                  60

Arg Leu Ser Phe Val Arg Ala Arg Pro Glu Thr Asn Ala Asp Leu Arg
65              70                  75                  80

Asp Ala Thr Leu Ala Phe Arg Gly Leu Arg Val Glu Asp Glu Gly Asn
                85                  90                  95

Tyr Thr Cys Glu Phe Ala Thr Phe Pro Asn Gly Thr Arg Arg Gly Val
                100                 105                 110

Thr Trp Leu Arg Val Ile Ala
            115
```

<210> SEQ ID NO 50
<211> LENGTH: 115
<212> TYPE: PRT
<213> ORGANISM: Mus musculus

<400> SEQUENCE: 50

Asp Ile Arg Val Leu Val Pro Tyr Asn Ser Thr Gly Val Leu Gly Gly
1               5                   10                  15

Ser Thr Thr Leu His Cys Ser Leu Thr Ser Asn Glu Asn Val Thr Ile
            20                  25                  30

Thr Gln Ile Thr Trp Met Lys Lys Asp Ser Gly Gly Ser His Ala Leu
        35                  40                  45

Val Ala Val Phe His Pro Lys Lys Gly Pro Asn Ile Lys Glu Pro Glu
    50                  55                  60

Arg Val Lys Phe Leu Ala Ala Gln Gln Asp Leu Arg Asn Ala Ser Leu
65                  70                  75                  80

Ala Ile Ser Asn Leu Ser Val Glu Asp Glu Gly Ile Tyr Glu Cys Gln
                85                  90                  95

Ile Ala Thr Phe Pro Arg Gly Ser Arg Ser Thr Asn Ala Trp Leu Lys
            100                 105                 110

Val Gln Ala
        115

<210> SEQ ID NO 51
<211> LENGTH: 115
<212> TYPE: PRT
<213> ORGANISM: Homo sapiens

<400> SEQUENCE: 51

Ser Gln Val Val Gln Val Asn Asp Ser Met Tyr Gly Phe Ile Gly Thr
1               5                   10                  15

Asp Val Val Leu His Cys Ser Phe Ala Asn Pro Leu Pro Ser Val Lys
            20                  25                  30

Ile Thr Gln Val Thr Trp Gln Lys Ser Thr Asn Gly Ser Lys Gln Asn
        35                  40                  45

Val Ala Ile Tyr Asn Pro Ser Met Gly Val Ser Val Leu Ala Pro Tyr
    50                  55                  60

Arg Glu Arg Val Glu Phe Leu Arg Pro Ser Phe Thr Asp Gly Thr Ile
65                  70                  75                  80

Arg Leu Ser Arg Leu Glu Leu Glu Asp Glu Gly Val Tyr Ile Cys Glu
                85                  90                  95

Phe Ala Thr Phe Pro Thr Gly Asn Arg Glu Ser Gln Leu Asn Leu Thr
            100                 105                 110

Val Met Ala
        115

<210> SEQ ID NO 52
<211> LENGTH: 115
<212> TYPE: PRT
<213> ORGANISM: Mus musculus

<400> SEQUENCE: 52

Thr Gln Val Val Gln Val Asn Asp Ser Met Tyr Gly Phe Ile Gly Thr
1               5                   10                  15

Asp Val Val Leu His Cys Ser Phe Ala Asn Pro Leu Pro Ser Val Lys
            20                  25                  30

Ile Thr Gln Val Thr Trp Gln Lys Ala Ser Asn Gly Ser Lys Gln Asn

```
            35                  40                  45
Met Ala Ile Tyr Asn Pro Thr Met Gly Val Ser Val Leu Pro Pro Tyr
 50                  55                  60
Glu Lys Arg Val Glu Phe Leu Arg Pro Ser Phe Ile Asp Gly Thr Ile
65                  70                  75                  80
Arg Leu Ser Gly Leu Glu Leu Glu Asp Glu Gly Met Tyr Ile Cys Glu
                85                  90                  95
Phe Ala Thr Phe Pro Thr Gly Asn Arg Glu Ser Gln Leu Asn Leu Thr
            100                 105                 110
Val Met Ala
        115

<210> SEQ ID NO 53
<211> LENGTH: 114
<212> TYPE: PRT
<213> ORGANISM: Homo sapiens

<400> SEQUENCE: 53

Ala Leu Ala Gly Pro Ile Ile Val Glu Pro His Val Thr Ala Val Trp
1               5                   10                  15
Gly Lys Asn Val Ser Leu Lys Cys Leu Ile Glu Val Asn Glu Thr Ile
                20                  25                  30
Thr Gln Ile Ser Trp Glu Lys Ile His Gly Lys Ser Ser Gln Thr Val
            35                  40                  45
Ala Val His His Pro Gln Tyr Gly Phe Ser Val Gln Gly Glu Tyr Gln
        50                  55                  60
Gly Arg Val Leu Phe Lys Asn Tyr Ser Leu Asn Asp Ala Thr Ile Thr
65                  70                  75                  80
Leu His Asn Ile Gly Phe Ser Asp Ser Gly Lys Tyr Ile Cys Lys Ala
                85                  90                  95
Val Thr Phe Pro Leu Gly Asn Ala Gln Ser Ser Thr Thr Val Thr Val
            100                 105                 110
Leu Val

<210> SEQ ID NO 54
<211> LENGTH: 114
<212> TYPE: PRT
<213> ORGANISM: Mus musculus

<400> SEQUENCE: 54

Ala Leu Ala Gly Ser Ile Ile Val Glu Pro His Val Thr Ala Val Trp
1               5                   10                  15
Gly Lys Asn Val Ser Leu Lys Cys Leu Ile Glu Val Asn Glu Thr Ile
                20                  25                  30
Thr Gln Ile Ser Trp Glu Lys Ile His Gly Lys Ser Ser Gln Thr Val
            35                  40                  45
Ala Val His His Pro Gln Tyr Gly Phe Ser Val Gln Gly Asp Tyr Gln
        50                  55                  60
Gly Arg Val Leu Phe Lys Asn Tyr Ser Leu Asn Asp Ala Thr Ile Thr
65                  70                  75                  80
Leu His Asn Ile Gly Phe Ser Asp Ser Gly Lys Tyr Ile Cys Lys Ala
                85                  90                  95
Val Thr Phe Pro Leu Gly Asn Ala Gln Ser Ser Thr Thr Val Thr Val
            100                 105                 110
Leu Val
```

<210> SEQ ID NO 55
<211> LENGTH: 117
<212> TYPE: PRT
<213> ORGANISM: Homo sapiens

<400> SEQUENCE: 55

Ala Gly Glu Leu Glu Thr Ser Asp Val Val Thr Val Val Leu Gly Gln
1               5                   10                  15

Asp Ala Lys Leu Pro Cys Phe Tyr Arg Gly Asp Ser Gly Glu Gln Val
            20                  25                  30

Gly Gln Val Ala Trp Ala Arg Val Asp Ala Gly Glu Gly Ala Gln Glu
        35                  40                  45

Leu Ala Leu Leu His Ser Lys Tyr Gly Leu His Val Ser Pro Ala Tyr
    50                  55                  60

Glu Gly Arg Val Glu Gln Pro Pro Pro Arg Asn Pro Leu Asp Gly
65                  70                  75                  80

Ser Val Leu Leu Arg Asn Ala Val Gln Ala Asp Glu Gly Glu Tyr Glu
                85                  90                  95

Cys Arg Val Ser Thr Phe Pro Ala Gly Ser Phe Gln Ala Arg Leu Arg
            100                 105                 110

Leu Arg Val Leu Val
        115

<210> SEQ ID NO 56
<211> LENGTH: 117
<212> TYPE: PRT
<213> ORGANISM: Mus musculus

<400> SEQUENCE: 56

Ala Gly Glu Leu Glu Thr Ser Asp Val Val Thr Val Val Leu Gly Gln
1               5                   10                  15

Asp Ala Lys Leu Pro Cys Phe Tyr Arg Gly Asp Pro Asp Glu Gln Val
            20                  25                  30

Gly Gln Val Ala Trp Ala Arg Val Asp Pro Asn Glu Gly Ile Arg Glu
        35                  40                  45

Leu Ala Leu Leu His Ser Lys Tyr Gly Leu His Val Asn Pro Ala Tyr
    50                  55                  60

Glu Asp Arg Val Glu Gln Pro Pro Pro Arg Asp Pro Leu Asp Gly
65                  70                  75                  80

Ser Val Leu Leu Arg Asn Ala Val Gln Ala Asp Glu Gly Glu Tyr Glu
                85                  90                  95

Cys Arg Val Ser Thr Phe Pro Ala Gly Ser Phe Gln Ala Arg Met Arg
            100                 105                 110

Leu Arg Val Leu Val
        115

<210> SEQ ID NO 57
<211> LENGTH: 105
<212> TYPE: PRT
<213> ORGANISM: Homo sapiens

<400> SEQUENCE: 57

Met Thr Gly Thr Ile Glu Thr Thr Gly Asn Ile Ser Ala Glu Lys Gly
1               5                   10                  15

Gly Ser Ile Leu Leu Gln Cys His Leu Ser Ser Thr Thr Ala Gln Val
            20                  25                  30

Thr Gln Val Asn Trp Glu Gln Gln Asp Gln Leu Leu Ala Ile Cys Asn

```
                35                  40                  45
Ala Asp Leu Gly Trp His Ile Ser Pro Ser Phe Lys Asp Arg Val Ala
 50                  55                  60

Pro Gly Pro Gly Leu Gly Leu Thr Leu Gln Ser Leu Thr Val Asn Asp
 65                  70                  75                  80

Thr Gly Glu Tyr Phe Cys Ile Tyr His Thr Tyr Pro Asp Gly Thr Tyr
                 85                  90                  95

Thr Gly Arg Ile Phe Leu Glu Val Leu
                100                 105

<210> SEQ ID NO 58
<211> LENGTH: 105
<212> TYPE: PRT
<213> ORGANISM: Mus musculus

<400> SEQUENCE: 58

Thr Ala Gly Thr Ile Asp Thr Lys Arg Asn Ile Ser Ala Glu Glu Gly
 1               5                  10                  15

Gly Ser Val Ile Leu Gln Cys His Phe Ser Ser Asp Thr Ala Glu Val
                20                  25                  30

Thr Gln Val Asp Trp Lys Gln Gln Asp Gln Leu Leu Ala Ile Tyr Ser
                35                  40                  45

Val Asp Leu Gly Trp His Val Ala Ser Val Phe Ser Asp Arg Val Val
 50                  55                  60

Pro Gly Pro Ser Leu Gly Leu Thr Phe Gln Ser Leu Thr Met Asn Asp
 65                  70                  75                  80

Thr Gly Glu Tyr Phe Cys Thr Tyr His Thr Tyr Pro Gly Gly Ile Tyr
                 85                  90                  95

Lys Gly Arg Ile Phe Leu Lys Val Gln
                100                 105

<210> SEQ ID NO 59
<211> LENGTH: 113
<212> TYPE: PRT
<213> ORGANISM: Homo sapiens

<400> SEQUENCE: 59

Arg Ala Leu Cys Glu Glu Val Leu Trp His Thr Ser Val Pro Phe Ala
 1               5                  10                  15

Glu Asn Met Ser Leu Glu Cys Val Tyr Pro Ser Met Gly Ile Leu Thr
                20                  25                  30

Gln Val Glu Trp Phe Lys Ile Gly Thr Gln Gln Asp Ser Ile Ala Ile
                35                  40                  45

Phe Ser Pro Thr His Gly Met Val Ile Arg Lys Pro Tyr Ala Glu Arg
 50                  55                  60

Val Tyr Phe Leu Asn Ser Thr Met Ala Ser Asn Asn Met Thr Leu Phe
 65                  70                  75                  80

Phe Arg Asn Ala Ser Glu Asp Asp Val Gly Tyr Tyr Ser Cys Ser Leu
                 85                  90                  95

Tyr Thr Tyr Pro Gln Gly Thr Trp Gln Lys Val Ile Gln Val Val Gln
                100                 105                 110

Ser

<210> SEQ ID NO 60
<211> LENGTH: 114
<212> TYPE: PRT
<213> ORGANISM: Mus musculus
```

```
<400> SEQUENCE: 60

Lys Ala Leu Cys Glu Glu Thr Leu Trp Asp Thr Thr Val Arg Leu Ser
1               5                   10                  15

Glu Thr Met Thr Leu Glu Cys Val Tyr Pro Leu Thr His Asn Leu Thr
            20                  25                  30

Gln Val Glu Trp Thr Lys Asn Thr Gly Thr Lys Thr Val Ser Ile Ala
        35                  40                  45

Val Tyr Asn Pro Asn His Asn Met His Ile Glu Ser Asn Tyr Leu His
    50                  55                  60

Arg Val His Phe Leu Asn Ser Thr Val Gly Phe Arg Asn Met Ser Leu
65                  70                  75                  80

Ser Phe Tyr Asn Ala Ser Glu Ala Asp Ile Gly Ile Tyr Ser Cys Leu
                85                  90                  95

Phe His Ala Phe Pro Asn Gly Pro Trp Glu Lys Lys Ile Lys Val Val
            100                 105                 110

Trp Ser

<210> SEQ ID NO 61
<211> LENGTH: 123
<212> TYPE: PRT
<213> ORGANISM: Homo sapiens

<400> SEQUENCE: 61

Gln Ile His Phe Val Lys Gly Val Trp Glu Lys Thr Val Asn Thr Glu
1               5                   10                  15

Glu Asn Val Tyr Ala Thr Leu Gly Ser Asp Val Asn Leu Thr Cys Gln
            20                  25                  30

Thr Gln Thr Val Gly Phe Phe Val Gln Met Gln Trp Ser Lys Val Thr
        35                  40                  45

Asn Lys Ile Asp Leu Ile Ala Val Tyr His Pro Gln Tyr Gly Phe Tyr
    50                  55                  60

Cys Ala Tyr Gly Arg Pro Cys Glu Ser Leu Val Thr Phe Thr Glu Thr
65                  70                  75                  80

Pro Glu Asn Gly Ser Lys Trp Thr Leu His Leu Arg Asn Met Ser Cys
                85                  90                  95

Ser Val Ser Gly Arg Tyr Glu Cys Met Leu Val Leu Tyr Pro Glu Gly
            100                 105                 110

Ile Gln Thr Lys Ile Tyr Asn Leu Leu Ile Gln
            115                 120

<210> SEQ ID NO 62
<211> LENGTH: 123
<212> TYPE: PRT
<213> ORGANISM: Mus musculus

<400> SEQUENCE: 62

Gln Ile Gln Phe Phe Arg Gly Val Trp Glu Glu Leu Phe Asn Val Gly
1               5                   10                  15

Asp Asp Val Tyr Ala Leu Pro Gly Ser Asp Ile Asn Leu Thr Cys Gln
            20                  25                  30

Thr Lys Glu Lys Asn Phe Leu Val Gln Met Gln Trp Ser Lys Val Thr
        35                  40                  45

Asp Lys Asn Asp Met Ile Ala Leu Tyr His Pro Gln Tyr Gly Leu Tyr
    50                  55                  60

Cys Gly Gln Glu His Ala Cys Glu Ser Gln Val Ala Ala Thr Glu Thr
65                  70                  75                  80
```

-continued

```
Glu Lys Gly Val Thr Asn Trp Thr Leu Tyr Leu Arg Asn Ile Ser Ser
                85                  90                  95

Ala Leu Gly Gly Lys Tyr Glu Cys Ile Phe Thr Leu Tyr Pro Glu Gly
            100                 105                 110

Ile Lys Thr Thr Val Tyr Asn Leu Ile Val Glu
        115                 120
```